US008765117B2

(12) United States Patent
Chien et al.

(10) Patent No.: US 8,765,117 B2
(45) Date of Patent: Jul. 1, 2014

(54) GENERATION OF VASCULARIZED HUMAN HEART TISSUE AND USES THEREOF

(75) Inventors: Kenneth R. Chien, Cambridge, MA (US); Lei Bu, Malden, MA (US); Xin Jiang, Chestnut Hill, MA (US); Kathy Oi Lan Lui, Boston, MA (US); Jolanta Chmielowiec, Houston, TX (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/375,402

(22) PCT Filed: Jun. 10, 2010

(86) PCT No.: PCT/US2010/038134
§ 371 (c)(1),
(2), (4) Date: Feb. 14, 2012

(87) PCT Pub. No.: WO2010/144678
PCT Pub. Date: Dec. 16, 2010

(65) Prior Publication Data
US 2012/0135051 A1    May 31, 2012

Related U.S. Application Data

(60) Provisional application No. 61/185,752, filed on Jun. 10, 2009, provisional application No. 61/256,960, filed on Oct. 31, 2009.

(51) Int. Cl.
*A01N 63/00* (2006.01)
*G01N 33/53* (2006.01)

(52) U.S. Cl.
USPC .................................. 424/93.21; 435/7.1

(58) Field of Classification Search
USPC .......................................... 424/93.1; 435/7.1
See application file for complete search history.

(56) References Cited

U.S. PATENT DOCUMENTS

| 2008/0213230 A1* | 9/2008 | Phillips et al. ............... 424/93.7 |
| 2008/0254003 A1 | 10/2008 | Passier et al. |
| 2010/0210713 A1 | 8/2010 | Chien et al. |

FOREIGN PATENT DOCUMENTS

| WO | 2008054819 A2 | 5/2008 |
| WO | 2010-011352 A2 | 1/2010 |
| WO | 2010011352 A2 | 1/2010 |

OTHER PUBLICATIONS

Theise et al Stem cell Reviews 2005; 1: 9-13).*
Djuric et al (Stem Cell Research & Therapy 2010, 1: 1-6).*
Serafini and Verfaillie (Semi Reprod Med 2006; 24: 379-88).*
Roberts et al (Cell Cycle 8:19, 3078-3081; Oct. 1, 2009; Landes Bioscience).*
Xu, et al. (Cell Research, 22(1): 142-54, 2012).*
Moretti et al (Cell, 127(6): 1151-1165, 2006).*
Yang Supplemental PDF, 2008, p. 1-8).*
Yang et al (Nature, 453(7194): 524-8, 2008).*
Cai, C. L. et al., "Isl1 Identifies a Cardiac Progenitor Population that Proliferates Prior to Differentiation and Contributes a Majority of Cells to the Heart" Dev Cell 5, 877-889 (2003).
Chien, K. R., et al. "Cardiogenesis and the Complex Biology of Regenerative Cardiovascular Medicine" Science 322, 1494-1497 (2008).
Ema, M. et al. "Primitive erythropoiesis from mesodermal precursors expressing VE-cadherin, PECAM-1, Tie2, endoglin, and CD34 in the mouse embryo" Blood 108, 4018-4024 (2006).
James, et al. "Expansion and maintenance of human embryonic stem cell-derived endothelial cells by TGFβ inhibition is Id1 dependent" Nature Biotech, 28, 161-166, (2010).
Kwon, C. et al. "Canonical Wnt signaling is a positive regulator of mammalian cardiac progenitors" Proc Natl Acad Sci U S A 104, 10894-10899 (2007).
Laugwitz, K. L. et al. "Postnatal isl1+ cardioblasts enter fully differentiated cardiomyocyte lineages" Nature 433, 647-53 (2005).
Moretti, A. et al. "Multipotent Embryonic Isl1+ Progenitor Cells Lead to Cardiac, Smooth Muscle, and Endothelial Cell Diversification" Cell 127, 1151-1165 (2006).
Qyang, Y. et al. "The Renewal and Differentiation of Isl1+ Cardiovascular Progenitors Are Controlled by a Wnt/β-Catenin Pathway" Cell Stem Cell 1, 165-179 (2007).
Tzahor, E. Wnt/β-Catenin Signaling and Cardiogenesis: Timing Does Matter. Dev Cell 13, 10-13 (2007).

(Continued)

*Primary Examiner* — Marcia S Noble
*Assistant Examiner* — Magdalene Sgagias
(74) *Attorney, Agent, or Firm* — Nixon Peabody LLP

(57) ABSTRACT

The present invention relates to the generation of vascularized human heart tissue from human primordial Islet1-positive (ISL1+) progenitors, and more particularly the generation of vascularized human heart tissue from human primordial Islet1+ cardiovascular stem cells which are positive for markers ISL1+/NKX2.5−/KDR−. One aspect of the invention relates to isolation of human ISL1+ primordial cells from human pluripotent cells, such as human ES cells or other human pluripotent stem cell sources, wherein the human ISL1+ primordial cells can differentiate into three different lineages; cardiomyocyte lineages, endothelial lineages and smooth muscle lineages. Another aspect relates to use and implantation of the human primordial ISL1+ progenitors into an animal model to generate human vascularized heart tissue, and more particularly, the production of an in vivo humanized model of vascular disease. One embodiment relates to the use of an in vivo humanized model of vascular disease as an assay, for example to assess drug toxicity and/or identify agents which increase and decrease coronary blood flow to the human vascularized heart tissue. Another embodiment relates to the therapeutic use of human primordial ISL1+ progenitors, for example, in one embodiment the invention provides methods for the treatment cardiovascular disorders and/or congenital heart disease in a subject comprising transplanting into subjects vascularized human heart tissue generated from human ISL1+ progenitors.

10 Claims, 24 Drawing Sheets

(56) References Cited

OTHER PUBLICATIONS

Yang, L. et al. "Human cardiovascular progenitor cells develop from a KDR+ embryonic-stem-cell-derived population" Nature 453, 524-528 (2008).
Zhou, B. et al. "Epicardial progenitors contribute to the cardiomyocyte lineage in the developing heart" Nature 454, 109-113 (2008).
Zhou, B., et al. "Nkx2-5- and Isl1-expressing cardiac progenitors contribute to proepicardium" Biochem Biophys Res Commun 375, 450-453 (2008).
Laugwitz et al., "Islet1 cardiovascular progenitors: a single source for heart lineages?" Development 135, 193 (2008).
Kattman et al., "Multipotent flk-1+ cardiovascular progenitor cells give rise to the cardiomyocyte, endothelial, and vascular smooth muscle lineages" Dev Cell 11, 723-32 (2006).
Sun et al. "Islet 1 is expressed in distinct cardiovascular lineages, including pacemaker and coronary vascular cells" Dev Biol 304, 286-96 (2007).
Motoike et al., "Evidence for novel fate of Flk1+ progenitor: contribution to muscle lineage" Genesis 35, 153-9 (2003).
Chien, "Regenerative medicine and human models of human disease" Nature. 453, 302-5 (2008).

* cited by examiner

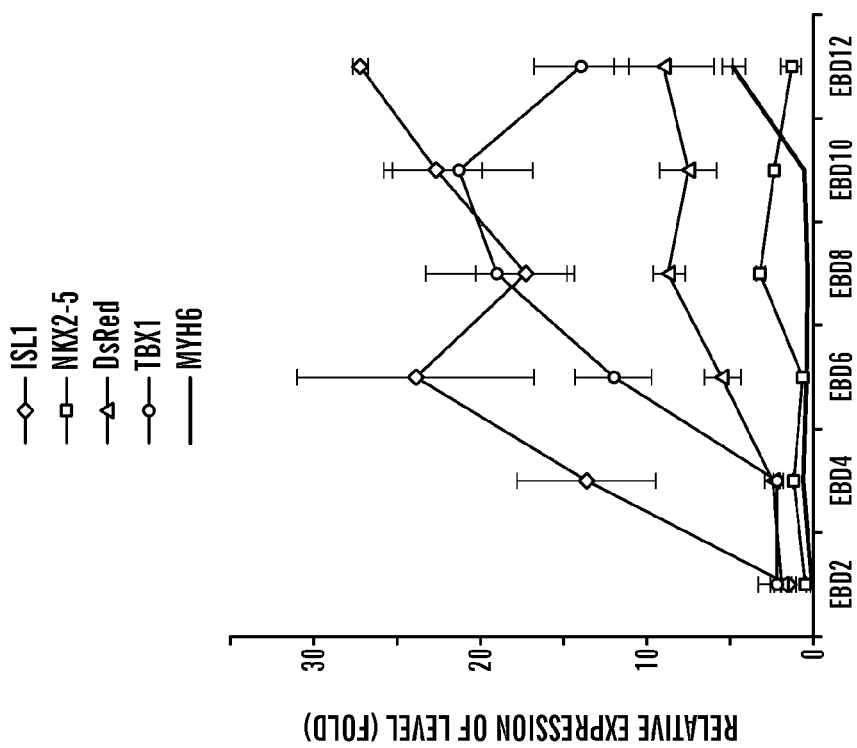
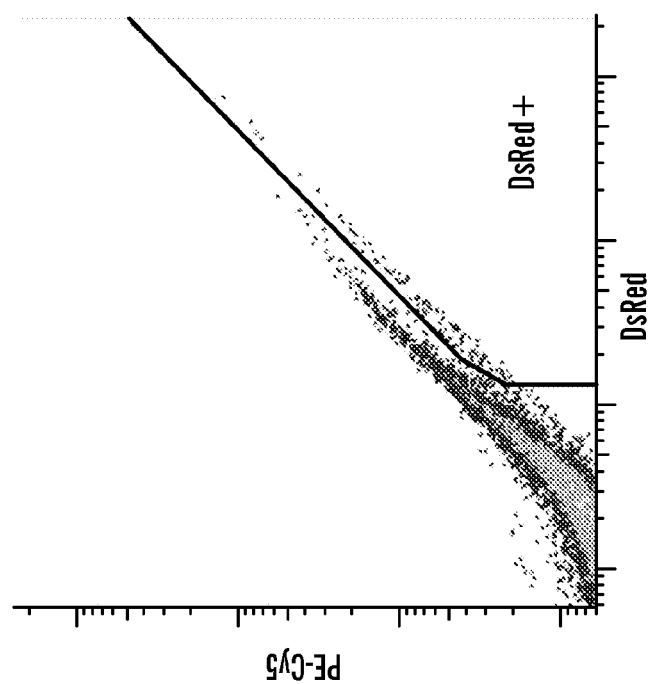
FIG. 3A
FIG. 3B

| | %GFP+CD31- | %GFP-CD31+ | %GFP+CD31+ |
|---|---|---|---|
| VEGF-D | 9.8 | 3.9 | 0.1 |
| Wnt3a+VEGF-D | 8.1 | 2.5 | 0.2 |
| VEGF-D+ALK5i | 1.3 | 33.3 | 0.8 |
| Wnt3a+VEGF-D+ALK5i | 2.1 | 30 | 0.6 |
| VEGF-D+ENDOCAN | 6.1 | 3 | 0.3 |
| --- | 5.7 | 1.4 | 0.2 |

FIG. 16C

GENERATION OF VASCULARIZED HUMAN HEART TISSUE AND USES THEREOF

CROSS REFERENCE TO RELATED APPLICATION

This Application is a 35 U.S.C. §371 National Phase Entry Application of International Application No. PCT/US2010/038134 filed Jun. 10, 2010, which designates the U.S., and which claims benefit under 35 U.S.C. §119(e) to U.S. Provisional Application 61/185,752, filed, Jun. 10, 2009 and U.S. Provisional Application 61/256,960, filed, Oct. 31, 2009, the entire contents of each are incorporated herein by reference.

FIELD OF THE INVENTION

The present invention relates to the field of tissue, organ and cell transplantation. Methods and compositions of production of human vascularized cardiac tissue are provided as well as an in vivo model of human cardiovascular disease and an in vivo assay for monitoring cardiac development, as well as identifying agents affecting human cardiovascular function.

BACKGROUND OF THE INVENTION

Cardiovascular disease is the leading cause of death in the U.S., and will be the primary cause of mortality in developing countries by 2010, as estimated by the WHO. Nevertheless, the demand for transplantation exceeds the availability of donor hearts. In this regard, cardiac regeneration has recently become an active area of research. Over the past few years, numerous reports demonstrate cardiac progenitors from diverse fetal and adult tissues outside the cardiovascular system, including adipose tissues, amniotic fluid, bone marrow, placenta, skeletal muscle, and testes (Franco et al., 2007). However, their low frequency of cardiac differentiation (Murry et al., 2004) and lack of long-term benefits fail to achieve cardiac cell regeneration (Fazel et al., 2006, 2008). Bone marrow cells, for instance, may improve the function of the infarcted heart mainly by promoting angiogenesis or cell survival without cardiac muscle regeneration (Fazel et al., 2006, 2007). A recently discovered cardiac progenitor population marked by the expression of the LIM homeodomain transcription factor isl1 (Laugwitz et al., 2005; Moretti et al., 2006; Qyang et al., 2007) is an attractive target to study cardiac regeneration. A multipotent islet 1 (isl1+) cardiovascular progenitor (MICP) is able to give rise to the major three cell types of the heart: cardiomyocytes, smooth muscles and endothelial cells, and has clonogenic and self-renewing ability (Laugwitz et al., 2005; Moretti et al., 2006). In Isl1 knockout mice, histological analysis of mutant hearts between embryonic day (ED) 9.0 and ED9.5 showed a misshapen single heart ventricle as the cause of death (Cai et al., 2003). Lineage tracing studies in mice document that isl1+ progenitors give rise to over two thirds of the cells in the heart, mostly on the right side, including most of the conduction system: the sinoatrial (SA) node, the atrioventricular (AV) node, Hisbundle, and Purkinje fiber complex (Cai et al, 2003; Laugwitz et al., 2005; Moretti et al., 2006; Sun et al., 2007). Disruption of development, differentiation or maturation of any of these components can lead to arrhythmias such as sinus arrest, AV block, ventricular tachycardia and sudden death (Bruneau et al., 2001).

The generation and expansion of diverse cardiovascular cell lineages is a critical step during human cardiogenesis with major implications for congenital heart disease. Unraveling the mechanisms for human heart cell lineage diversification has been hampered by the lack of genetic tools to purify early cardiac progenitors and define their developmental potential[1-4]. Recent studies in the mouse embryo have identified a multipotent cardiac progenitor (MICP), which contributes to all the major cell types in the murine heart[5-8]. In contrast to murine development, human cardiogenesis has a much longer onset of heart cell lineage diversification and expansion, suggesting divergent pathways.

Accordingly, improved methods for identifying human pluripotent progenitors which give rise to human multipotent cardiac progenitors (hMICP) for the development of human diverse cardiovascular cell lineages and the production of human cardiac tissue are needed.

SUMMARY OF THE INVENTION

The present invention relates to human ISL1+ primordial cardiovascular progenitors that give rise to the cardiomyocyte, smooth muscle, and endothelial cell lineages. Using two independent transgenic and gene-targeting approaches in human embryonic stem (hES) cell lines, the inventors demonstrate that purified ISL1+ primordial progenitors are capable of self-renewal and expansion prior to differentiation into the three major cell types in the heart. The inventors demonstrate that ES-derived human ISL1+ primordial progenitors are useful for the generation of human model systems for cardiovascular disease and novel approaches for human regenerative cardiovascular medicine.

One aspect of the present invention relates to method to differentiate human embryonic stem (ES) cells, or human induced pluripotent cells (iPSCs) into human primordial isl1+ progenitors, which can further differentiate in vivo, into cardiac, smooth, and endothelial lineages which integrate into the functional myocardium.

One aspect of the present invention relates to a method to increase the efficiency of differentiation of mbryonic stem (ES) cells, or human induced pluripotent cells (iPSCs) along vasculargenic lineages by contacting the ES cells or iPSCs with VEGF and/or an inhibitor of the TGFβ signaling pathway, such as an ALK5 inhibitor (ALK5i) or the like. Another aspect of the invention relates to increasing the yield of CD31+ cells differentiated from ES cells and/or iPSCs by culturing the cells in a media comprising VEGF or an analogue or functional homologue thereof, and/or an inhibitor of the TGFβ signaling pathway, such as an ALK5 inhibitor (ALK5i) or the like.

The inventors herein have demonstrated, by isolating the human primordial isl1+ multipotent cardiovascular progenitors and differentiating them into specified cardiac cells, that the human primordial isl1+ multipotent cardiovascular progenitors are able to differentiate and regenerate functional cardiac cells in the heart. In particular, using human primordial isl1+ progenitors, the inventors have demonstrated the ability to generate three-dimensional human vascularized cardiac tissue in vivo.

In particular, by implanting the human primordial isl1+ multipotent cardiovascular progenitors into a subject, the inventors have demonstrated production of vascularized human heart tissue. The inventors demonstrate that as the human primordial isl1+ progenitors differentiate vascularogeneis is coordinated with cardiac muscle growth so that vascularization of the muscle cells occurs in vivo.

Accordingly, one aspect of the present invention relates to the generation of vascularized human heart tissue from human primordial Islet1-positive (ISL1+) progenitors, and more particularly the generation of vascularized human heart tissue from human primordial Islet1+ cardiovascular stem cells which are positive for markers ISL1+, and negative for markers NKX2.5−/KDR−. The inventors demonstrate that these human ISL1+ primordial cardiovascular progenitors give rise to a family of multipotent intermediate progenitors, including multipotent Isl1+ cardiovascular progenitor cells (MICPs) which are Isl1+/Nkx2.5+/KDR+, as disclosed in International Patent WO 2008/054819 which is incorporated herein in its entirety by reference (see also FIG. 5 herein).

One aspect of the invention relates to isolation of human ISL1+ primordial cells from a population of human pluripotent cells, such as, for example human ES cells or other human pluripotent stem cell sources such as iPS cells or human ES cell lines. In some embodiments, the human ES cells are obtained without destroying a human embryo. In some embodiments, the human ISL1+ primordial cells can be induced to differentiate into three different lineages in vivo; cardiomyocyte lineages, endothelial lineages and smooth muscle lineages.

Another aspect relates to use and implantation of the human primordial ISL1+ progenitors into an animal model to generate human vascularized heart tissue, and more particularly, the production of an in vivo humanized model of vascular disease. One embodiment relates to the use of an in vivo humanized model of vascular disease as an assay, for example to assess drug toxicity and/or identify agents which increase and decrease coronary blood flow to the human vascularized heart tissue. Another embodiment relates to the therapeutic use of human primordial ISL1+ progenitors, for example, in one embodiment the invention provides methods for the treatment cardiovascular disorders and/or congenital heart disease in a subject comprising transplanting into subjects vascularized human heart tissue generated from human ISL1+ progenitors.

As disclosed herein, the inventors have discovered a human ISL1+ primordial cardiovascular stem cell that is capable of differentiating into multiple different lineages. In particular, one aspect of the invention relates to methods for isolating a human ISL1+ primordial cardiovascular stem cell from a population of cells, such as ES cells or pluripotent cells, involving identifying cells where are positive for Islet 1 expression (Isl1+) and negative for expression of Nkx2.5 and/or KDR expression, and isolating and collecting the cells which are positive for islet expression but not for Nkx2.5 or KDR expression (e.g. positive cells which are ISL1+/Nkx2.5−/KDR−) from those cells which are negative for Islet1 expression or express Nkx2.5 and/or KDR (e.g. negative cells which are ISL1−, or ISL+/Nkx2.5+ and/or KDR+). In some embodiments, the human ISL1+ primordial cardiovascular stem cell are SCA−, C-KIT− and CD31−.

Another aspect relates to methods for the differentiation of human primordial ISL1+ progenitors into human cardiovascular vascular progenitors and cardiovascular muscle progenitors. In one embodiment, the agents are reactive to nucleic acids and in another embodiment the agents are reactive to the expression products of the nucleic acids.

In another embodiment, the human Isl1+ progenitors (which are Isl1+/Nkx2.5−/KDR−) are differentiated along vascularogenic lineages, e.g., to cardiovascular progenitors, where the cells are differentiated into Isl1+/CD31+ cells by contacting the cells with at least one of the following; VEGF, VEGF homologue, a inhibitor of TGF-β signalling, an ALK5-inhibitor and the like. In some embodiments, the human Isl1+ progenitors are differentiated along vascularogenic lineages to differentiate into Isl1+/CD31+ cells by contacting the cells with at least one or more growth factor, selected from the group comprising; the following; vascular endothelial growth factor (VEGF, including, but not limited to VEGF-165), interleukins, fibroblast growth factors, for example, but not limited to, FGF-1 and FGF-2, hepatocyte growth factor, (HGF), endothelins (such as ET-1, ET-2, and ET-3), insulin-like growth factor (IGF-1), angiopoietins (such as Ang-1, Ang-2, Ang-3/4), angiopoietin-like proteins (such as ANGPTL1, ANGPTL-2, ANGPTL-3, and ANGPTL-4), platelet-derived growth factor (PDGF), including, but not limited to PDGF-AA, PDGF-BB and PDGF-AB, epidermal growth factor (EGF), endothelial cell growth factor (ECGF), including ECGS, platelet-derived endothelial cell growth factor (PD-ECGF), placenta growth factor (PLGF), and the like. In some embodiments, contacting a population of human Isl1+ progenitors with a VEGF, or a VEGF homologue, or a inhibitor of TGF-β signalling, an ALK5-inhibitor increases the efficiency to differentiate into Isl1+/CD31+ vasculargenic cells by about at least 1.5-fold, or at least about 2.0-fold, or at least about 3.0-fold, or at least about 4.0-fold, or at least about 5-fold or at least about 6.0-fold or more than 6.0-fold, as compared to in the absence of a VEGF, or a VEGF homologue, or a inhibitor of TGF-β signalling, an ALK5-inhibitor.

In one embodiment, a method of isolating human primordial ISL1+ progenitors from a population of cells is using lineage tracing, such as disclosed herein in the examples, where isolating the human primordial ISL1+ progenitors expressing ISL1, but not expressing NKX2.5 or KDR can be using conventional methods of using a marker gene operatively linked to the promoter of Isl1 and/or Nkx2.5 and/or KDR.

In some embodiments, a human primordial ISL1+ progenitor as disclosed herein and for use in the methods as disclosed herein can be derived from a pluripotent stem cell, for example but not limited to an embryoid body (EBs), an embryonic stem (ES) cell, an adult stem cell (ASCs), an induced pluripotent stem cell (iPS) or in some embodiments, from an induced pluripotent stem cell which can be reprogrammed further (e.g., a partial iPSC). Alternatively, in some embodiments, a human primordial ISL1+ progenitor as disclosed herein can also be derived from any tissue, including but not limited to embryonic tissue, pre-fetal and fetal tissue, postnatal tissue, and adult tissue.

One aspect of the present invention relates to the use of human primordial ISL1+ progenitors to generate functional vascularized human cardiac tissue in vivo. In one embodiment, the human primordial ISL1+ progenitors are implanted into a subject, where they spontaneously differentiate into human smooth muscle progenitors, epithelial progenitors and cardiomyocyte progenitors, which further differentiate into smooth muscle tissue, vascular tissue and cardiac muscle respectively. In some embodiments, where a population of human primordial ISL1+ progenitors are implanted into a subject, some cells within the population will differentiate along cardiomyocyte lineages, some will differentiate along endothelial lineages and some along smooth muscle lineages. Accordingly, one aspect of the present invention relates to the use of human primordial ISL1+ progenitors to generate a functional three-dimensional vascularized cardiac tissue in vivo, with out the need of scaffolds or matrices or other manipulations (e.g. addition of growth factors or angiogenic agents or other agents) for production of human vascularized cardiac tissue.

In some embodiments, when a population of human primordial ISL1+ progenitors are implanted into a subject, some primordial ISL1+ progenitors will self-replicate (e.g. proliferate or renew), and some will differentiate along cardiomyocyte lineages to produce a cardiomyocyte progenitor, or differentiate along an endothelial lineage to produce an endothelial progenitor, or differentiate along a smooth muscle lineage to produce a smooth muscle progenitor. In such instances, these human cardiomyocyte progenitors, human endothelial progenitors and human smooth muscle progenitors can self-replicate (e.g. proliferate) before terminally differentiating into cardiomyocytes, endothelial cells and smooth muscle cells respectively.

In some embodiments, the human ISL1+ progenitors are implanted into a subject, for example a human, for example for therapeutic purposes, or an animal subject. In some embodiment, human ISL1+ progenitors can be implanted into any suitable location in a subject, for example but not limited to, a kidney such as a kidney capsule, heart, ascites, peritoneal cavity, pericardium, epicardium, on the surface of the heart, in a pericardial space, and the like. In some embodiments, a population of human ISL1+ progenitors are encapsulated in a bioreactor bag, which can be implanted into a subject at a suitable location, for example on the surface of the heart, subcutaneously or the like In another embodiment, the three-dimensional human vascularized cardiac tissue as disclosed herein can be used for prophylactic and therapeutic treatment of a cardiovascular condition or disease. By way of an example only, in such an embodiment, a three-dimensional human vascularized cardiac tissue produced by the methods as disclosed herein can be administered to a subject, such as a human subject by way of transplantation or implantation, where the subject is in need of such treatment, for example, the subject has, or has an increased risk of developing a cardiovascular condition or disorder.

The compositions comprising three-dimensional human vascularized cardiac tissue as disclosed herein are distinguished from other engineered cardiac tissue by virtue of the human vascularized cardiac tissue disclosed herein is naturally vascularized. The human ISL1+ primordial progenitors undergo coordinated differentiation to form different cell types in the heart, e.g. cardiomyogenic progenitors cells, such as the ventricular myogenic progenitor cells, endothelial cells and smooth muscle cells, which are spatially and temporally coordinated such that they function together to form three-dimensional human vascularized cardiac tissue.

In particular, the inventors have demonstrated that after one month, implanted human ISL1+ primordial progenitors implanted into the kidney capsule of mice have undergone coordinated differentiation into different cardiac cell types to form distinct vascular type structures, with the lumen surface positive for CD31 (endothelial marker) expression, surrounded by a layer of cells positive for the smooth muscle marker SM-A, and peripheral to the layer of cells positive for SM-A are cells which express α-actinin, a marker for cardiomyocytes. Thus, the inventors have demonstrated the generation of human vascularized cardiac tissue in vivo from a population of ES-derived human ISL1+ primordial progenitors. Stated a different way, the inventors have demonstrated that human ISL1+ primordial progenitors differentiate in vivo to form an organized human cardiac tissue having a three-dimensional cellular organization of the cardiac tissue that is vascularized.

Each tissue type in the three-dimensional human vascularized cardiac tissue can be identified by cell specific markers, for example by detection by reacting with an agent which specifically binds to a protein and/or nucleic acid of such a marker expressed by the cell, e.g. ISL1+ primordial progenitor or any of its progeny. Detection can be accomplished using standard techniques such as electron, fluorescent and/or atomic force microscopy, as well as fluorescent cell sorting (FACS) and other cell sorting methodologies.

In some embodiments where human ISL1+ progenitors are implanted into an animal subject, the animal can be use as an in vivo humanized model of vascular disease. For example, an animal model which comprises functional vascularized human cardiac tissue, can be used to screen for agents which affect any one, or a combination of viability, functionality, contractibility, differentiation of the human cardiac tissue. As apposed to most in vitro assays or rodent or animal models, the use of the in vivo humanized model of vascular disease has a major advantage over existing assays using cardiac progenitor cells, is that it can be used to monitor or assess the effect of any drug or agent on human cardiac tissue in vivo.

Accordingly, one embodiment relates to the use of an in vivo humanized model of vascular disease as an assay, for example to assess drug toxicity (e.g. cardiotoxicity) on human heart tissue in vivo (e.g. to identify agents which increase apoptosis, decrease viability, modulate (e.g. increase or decrease by a statistically significantly amount) contractibility and/or conductivity of heart tissue). In some embodiments, the drugs and/or compounds can be existing drugs or compounds, and in other embodiments, the drugs or compounds can be new or modified drugs and compounds.

In another embodiment, an in vivo humanized model of vascular disease can be used as an assay for example to identify agents which increase and decrease coronary blood flow to human vascularized heart tissue in vivo. For example, in one embodiment, the human vascularized heart tissue could be given atherosclerosis, for example by implanting the human ISL1+ progenitors into a LDR −/− mouse and feeding the mouse a high fat diet.

Another aspect of the invention relates use of the in vivo humanized model of vascular disease as disclosed herein to screen for agents, for example molecules and genes involved in biological events. In such an embodiment, the biological event is an event that affects the differentiation of a human ISL1+ progenitor, or the function of the human vascularized cardiac tissues. The in vivo humanized model of vascular disease can be used to identify any agent which promotes the differentiation, proliferation, survival, regeneration, maintenance of the undifferentiated state of the ISL1+ progenitor, and/or inhibition or down-regulation of differentiation.

In another embodiment, the in vivo humanized model of vascular disease can be used to assess the effect of genetic variation (e.g. ethnicity, human mutations or gene variants or polymorphism) on cardiac function. For example, the effect of different environmental factors, such as, for example, obesity, high fat diet, lack of exercise, can be assessed in human vascularized cardiac tissue in vivo generated from ISL1+ progenitors from different genetic backgrounds. In an alternative embodiment, the effect (e.g. efficacy and/or safety profile) of different therapeutic agents and cardiac drugs can be assessed in human vascularized cardiac tissue in vivo generated from ISL1+ progenitors from different genetic backgrounds. Accordingly, in some embodiments, an in vivo humanized model of vascular disease is generated using human primordial ISL1+ progenitors which are a variant human primordial ISL1+ progenitor, for example but not limited to a genetic variant and/or a genetically modified human primordial ISL1+ progenitor.

In another embodiment, the in vivo humanized model of vascular disease as disclosed herein can be used as an assay for example to identify other cells which can be implanted in combination with the human ISL1+ cells, for example, addition of committed ventricular progenitors (CVP) as disclosed in International Patent Application PCT/US2009/060224, which is incorporated herein in its entirety by reference.

In another embodiment, the in vivo humanized model of vascular disease can be used in an assay for studying the differentiation pathways of human primordial ISL1+ progenitors into multiple lineages, for example but not limited to, human cardiac, human smooth muscle and human endothelial cell lineages. In some embodiments, the human primordial ISL1+ progenitors can be genetically engineered to comprise markers operatively linked to promoters that are expressed in one or more of the lineages being studied.

In some embodiments, the in vivo humanized model of vascular disease can be used in an assay for studying the differentiation pathway of human ISL1+ progenitors into subpopulations of human cardiomyocytes. In some embodiments, the human ISL1+ progenitors can be genetically engineered to comprise markers operatively linked to promoters that drive gene transcription in specific cardiomyocyte subpopulations, for example but not limited to, atial, ventricular, outflow tract and conduction systems. In other embodiments, the human ISL1+ progenitors can be used in an assay for studying the role of cardiac mesenchyme on cardiovascular stem cells.

In alternative embodiments, the human ISL1+ progenitors used to generate human vascularized tissue, and for the generation the in vivo humanized model of vascular disease can comprise a mutation and/or polymorphism that relates to the disease phenotype, and in other embodiments, the human ISL1+ progenitor been genetically engineered to carry a mutation and/or polymorphism.

Any suitable animal can be used for implanting a population of ISL1+ cells to generate an in vivo humanized model of vascular disease as disclosed herein, for example, rodents (such as mice, rats), monkeys, pigs and the like. In some embodiments, the subject animal is a transgenic or knockout animal, such as transgenic mice or knock out mice. In some embodiments, the subject animal is a humanized mouse, such as the SCID mouse.

The use of the in vivo humanized model of vascular disease for identifying agents for effect on human heart function as disclosed herein provides significant advantages over existing method to assess agents on cardiac tissue, because the in vivo humanized model of vascular disease comprises human vascularized cardiac tissue which is formed from ISL1+ primordial cells in vivo, and is properly vascularized and comprises all the desired cell types of heart tissue, including cells of cardiomyocyte phenotypes, endothelial cell phenotypes, smooth muscle phenotypes, as well as characteristics and properties of functional heart tissue. Thus the in vivo humanized model of vascular disease as disclosed herein provides a model of human heart tissue in vivo, which is significantly advantageous over existing cardiac function assays which either are assays using human heart tissue in vitro, or are in vivo models using non-human heart tissue.

Another embodiment relates to the therapeutic use of human primordial ISL1+ progenitors, for example, in one embodiment the invention provides methods for the treatment cardiovascular disorders and/or congenital heart disease in a subject comprising transplanting into subjects vascularized human heart tissue generated from human ISL1+ progenitors.

In another aspect of the invention, the methods provide use vascularized human cardiac tissue produced from the human ISL1+ progenitors by the methods as disclosed herein. In one embodiment, the vascularized human cardiac tissue can be used for the production of a pharmaceutical composition, for the use in transplantation into subjects in need of cardiac tissue transplantation, for example but not limited to subjects with congenital and/or acquired heart disease and/or subjects with vascular diseases. In one embodiment, human ISL1+ progenitors which are used to produce a vascularized human cardiac tissue can be genetically modified. In another aspect, the subject can have or be at risk of heart disease and/or vascular disease. In some embodiments, the human ISL1+ progenitors which are used to produce the vascularized human cardiac tissue can be autologous and/or allogenic. In some embodiments, the human ISL1+ progenitors used to produce a vascularized human cardiac tissue for transplanted are immunogenetically matched to the transplant receipt (e.g. blood type and HLA matched). In one embodiment, the allogenic ISL1+ primordial progenitors are cells are from an individual with similar tissue antigen, or otherwise immunologically compatible individuals.

In some embodiments, a subject in which human ISL1+ progenitors are transplanted, for therapeutic purposes is a mammal, and in other embodiments the mammal is a human.

In some embodiments, an agent useful in the methods as disclosed herein is reactive to a nucleic acid encoding human ISL1, NKX2.5 and KDR. Examples of such agents include, for example but are not limited to RNA; messenger RNA (mRNA); and genomic DNA, nucleic acid agents or proteins or fragment thereof. In some embodiments, a nucleic acid agent is comprises DNA; RNA; PNA; or pcPNA. In some embodiments, an agent is reactive to the expression products of the nucleic acids encoding human Islet 1, Nkx2.5 and KDR, for example an agent is a nucleic acid agent or protein or fragment thereof, such as, for example an antibody or antibody fragment. In some embodiments, an agent is a small molecule or aptamer.

In some embodiments, a reporter gene useful in the methods as disclosed herein encodes a protein having fluorescence activity and/or chromogenic activity, such as a fluorescent protein or fragment thereof. In some embodiments, a fluorescent protein can be detected by fluorescence cell sorting (FACS), fluorimetry, and/or microscope techniques. In some embodiments, the method encompasses separating the reactive positive Islet1+(ISL1+) cells from the Islet-negative cells (ISL−), and then assessing the ISL1+ cells for lack of expression of NKX2.5 and lack of expression of KDR fluorescence cell sorting (FAC). In some embodiments, a reporter gene useful in the methods as disclosed herein encodes an enzyme, for example but not limited to, β-galactosidase (β-gal); β-lactamase; dihydrofolate reductase (DHFR); luciferase; chloroamphenicol acetyl transferase, beta-glucosidase, beta-glucuronidase and modifications and fragments and variants thereof.

In some embodiments, where the method relates to isolating a population of human primordial ISL1+ progenitors from a population of cells, such as ES cells or ES cell line, one of ordinary skill in the art can introduce a reporter gene operatively linked to the regulatory sequence of the Islet1 gene, as disclosed herein, and optionally also a different reporter gene operatively linked to one or more other genes, such as Nkx2.5 and/or KDR genes, and separating ISL1+ reactive positive cells from the ISL1-negative cells, and then separating the ISL1+ cells from those also not expressing NKX2.5 and not expressing KDR to achieve a substantially pure population of isolated human primordial ISL1+ progenitors. In some embodiments, a regulatory sequence can be a promoter sequence or part of a promoter sequence thereof sufficient to direct transcription. In some embodiments, a reporter gene can be a resistance gene.

Another aspect of the present invention relates to a composition comprising a substantially pure isolated population of human primordial ISL1+ progenitors which are Islet1$^+$, Nkx2.5− and KDR− cardiovascular stem cells. In some embodiments, the composition comprises human primordial ISL1+ progenitors that have been genetically modified, such as genetically modified human ES cells.

In some instances, reports of ES cell-derived cardiac grafts do not survive longer than three months when in vivo. In some embodiments, the human ISL1+ primordial progenitors are genetically modified to promote survival in response to the stretch stress from contraction. For example, in some embodiments, the human ISL1+ primordial are genetically modified to prolong the survival of humanized vascularized cardiac graft tissue by inhibiting apoptosis, promoting survival pathways, and minimizing immune rejection of the isl1+ progenitors and their differentiated cardiac cells. In some embodiments, the ISL1+ progenitors are genetically modified to express truncated Creb3L2, as disclosed in U.S. Patent Application 61/145,208, filed on Jan. 16, 2009, and U.S. patent application Ser. No. 12/687,590, filed Jan. 14, 2010 which are both incorporated herein in their entirety by reference.

One aspect of the present invention relates to a method for generating human three-dimensional vascular cardiac tissue, the method comprising implanting a population of human ISL1+ primordial cardiovascular progenitors into a subject, wherein the human ISL1+ primordial cardiovascular progenitors undergo coordinated differentiation into cardiomyocytes, endothelial cells, and smooth muscle cells to generate human three-dimensional vascularized cardiac tissue. In some embodiments, the human ISL1+ progenitors are negative for the expression of Nkx2.5 and/or KDR, and can be derived from any one of human ES cells, human ES cell lines or from iPS cells. In some embodiments, the human ISL1+ progenitors are genetically modified human ISL1+ progenitors. In some embodiments, the population of human ISL1+ progenitors are implanted into the kidney capsule of the subject, or in other locations, such as, for example, kidney capsule, peritoneal cavity, liver, ascites, pericardium, epicardium, pericardial space, heart, on the surface of the heart, subcutaneous space. In some embodiments, a population of human ISl1+ progenitors is implanted into a subject in a bioreactor or capsule. In some embodiments, a population of human ISl1+ progenitors comprises at least one additional cell type, such as for example, committed ventricular progenitors (CVPs), wherein the CVP express at least two of the following markers; Mef2c, Nkx2.5, Tbx20, Isl1, GATA4, GATA6, Tropinin T, Tropinin C.

In some embodiments, a population of ISL1+ primordial progenitors is implanted into a subject that is a mammalian subject, such as a human subject or an animal, such as, but not limited to a rodent, monkey or pig.

Another aspect of the present invention relates to a composition comprising a substantially pure population of human ISL1+ primordial cardiovascular progenitor cells. Another aspect of the present invention relates to a composition comprising human vascularized cardiac tissue produced by the methods as disclosed herein. In some embodiments such a composition can be used for the treatment of cardiovascular disease or disorder in a subject, wherein the composition is administered to the subject in need of treatment.

Another aspect of the present invention relates to a container comprising the composition comprising a substantially pure population of human ISL1+ primordial cardiovascular progenitor cells and a suitable stem cell media. Another aspect of the present invention relates to a container comprising the composition comprising a human vascularized cardiac tissue and a suitable stem cell media.

Another aspect of the present invention relates to a method for treatment of cardiovascular disease in a subject, the method comprising administering to a subject a composition comprising human three-dimensional vascularized cardiac tissue, for example a the human three-dimensional vascularized cardiac tissue is produced by the methods as disclosed herein. In some embodiments, the human three-dimensional vascularized cardiac tissue is administered in a pharmaceutical acceptable carrier, such as a gel, matrix or like. In some embodiments, a human three-dimensional vascularized cardiac tissue further comprises a scaffold or matrices. In some embodiments, a human three-dimensional vascularized cardiac tissue is administered to the heart of the subject, such as attached on or within the surface of the heart of the subject, for example, the three-dimensional human vascularized cardiac tissue can be placed as a "patch" on the subjects heart at the location of injury, damage or malfunction of the heart.

Another aspect of the present invention relates to an in vivo assay of human cardiovascular disease, comprising an animal subject comprising a population of human ISL1+ primordial progenitors, wherein the human ISL1+ primordial cardiovascular progenitors have undergone coordinated differentiation into cardiomyocytes, endothelial cells, and smooth muscle cells to generate human three-dimensional vascularized cardiac tissue in the animal subject. In some embodiments, an animal subject is selected from the group of subjects; rodent, mice, monkey, pig, and includes, for example knock out or transgenic animals, such as the knockout mouse (LDR −/−). In some embodiments, the LDR knockout mouse (LDR −/−) is fed a high fat diet.

In some embodiments, an in vivo assay of human cardiovascular disease can be used to identify agents which increase or decrease the function of human three-dimensional vascularized cardiac tissue in the animal subject, for example to identify agents which increases or decreases by a statically significant amount at least one of the following properties selected from; contractile force, contractibility, cardiomyocyte atrophy, altered contraction, frequency of contraction, contraction duration, contraction stamina, vascularization of the human three-dimensional vascularized cardiac tissue as compared to the absence of the agent identified the agent which increases or decreases the function of human three-dimensional vascularized cardiac tissue.

In some embodiments, an in vivo assay of human cardiovascular disease can be used to identify an agent which is a cardiotoxic agent, or alternatively, can be used to identify an agent which increases or decreases blood flow in the human three-dimensional vascularized cardiac tissue.

Another aspect of the present invention relates to a method of screening agents which affect human cardiovascular function, the method comprising; (i) administering to an animal subject comprising human ISL1+ primordial progenitors at least one agent, wherein the human ISL1+ primordial cardiovascular progenitors have undergone coordinated differentiation into cardiomyocytes, endothelial cells, and smooth muscle cells to generate human three-dimensional vascularized cardiac tissue; (ii) monitoring the function of the human three-dimensional vascularized cardiac tissue in the presence of the agent as compared to in the absence of the agent; wherein an agent which has a statistically significant effect on the function of the human three-dimensional vascularized cardiac tissue as compared to in the absence of the agent identifies the agent as having an affect on human cardiovascular function.

In some embodiments, the method of screening measures a quantifiable parameter of the function of the human three-dimensional vascularized cardiac tissue in vivo, such as, for example, the measurement of at least one of; contractile force, contractibility, cardiomyocyte atrophy, altered contraction, frequency of contraction, contraction duration, contraction stamina, vascularization of the human three-dimensional vascularized cardiac tissue. In some embodiments, the method of screening measures the function of the human three-dimensional vascularized cardiac tissue, for example, measures at least one of; differentiation, survival and regeneration of the human three-dimensional vascularized cardiac tissue.

In some embodiments, administration of an agent to the animal which is the in vivo assay of human cardiovascular disease can be administered by any means commonly known to persons of ordinary skill in the art, and includes, for example, systemic administration, intravenous, transdermal, intrasynovial, intramuscular, oral administration, parenteral administration, intraarterial administration, intrathecal administration, intraventricular administration, intraparenchymal, intracranial, intracisternal, intrastriatal, and intranigral administration, and intracoronary administration.

BRIEF DESCRIPTION OF THE DRAWINGS

FIG. 1A shows immunostaining of sections from RA/SVC, and FIG. 1B shows immunostaining of the proximal OFT with indicated antibodies. ISL1+ cells are pointed out by white arrows and transient intermediates, ISL1+/cTNT+ and ISL1+/SMMHC+ are pointed out by yellow arrows. Scale bars: 50 µm in a right panels and b lower panels, 25 µm in the rest panels. Ao: aorta; PA: pulmonary artery; LA: left atrium; RV: right ventricle; LV: left ventricle; PV: pulmonary veins; pvl: pulmonary valve.

FIG. 2A shows X-gal staining and immunostaining showing LacZ and ISL1 co-stained in human ISL1-βgeo BAC transgenic cells from EB day 6 (left) and a βgeo+ colony was formed on CMC feeders in additional five days (right). Scale bars: 5 µm. FIG. 2B shows a diagram of the human ISL1-cre knock-in construct. FIG. 2C shows southern blotting and FIG. 2D shows a long range PCR confirming the homologous integration of the human ISL1-cre knock-in construct. Primer pair P1/P2, indicated in FIG. 2B was used for the long range PCR. FIG. 2E shows immunostaining showing the co-expression of DsRed and ACTN2 or cTNT (orange arrows) in the human ISL1-cre DsRed cells from day 16 beating EBs.

FIGS. 3A-3E show the isolation and characterization of hES cell-derived ISL1+ cardiac progenitors and their progeny. FIG. 3A shows the results of gene expression of the human ISL1-cre DsRed ES cells at different in vitro differentiation stages. FIG. 3B shows a FACS diagram to isolate DsRed+ cells from day 8 EBs of human ISL1-cre DsRed cells. FIG. 3C shows results from quantitative PCR (qPCR) showing gene expression of DsRed+ versus DsRed– cells isolated from day 8 human ISL1-cre DsRed EBs. FIG. 3D shows the gene expression profile of single DsRed+ cell-derived clones. FIG. 3E shows immunostaining showing single DsRed+ cell-derived clones gave rise to three cardiovascular lineages after additional 14 days of differentiation. The ± signs represent standard deviations (s.d.); n=3.

FIG. 4A shows FACS analyses showing DsRed+ populations of cells expanded on MEF feeders or Wnt3a-secreting feeders. FIG. 4B shows the gene expression profile of single DsRed+ cell-derived clones expanded with Wnt3a-conditioned medium. FIG. 4C shows immunostaining results showing Wnt3a-expanded DsRed+ cells gave rise to cardiomyocyte (cTNT+) and smooth muscle (SMMHC+) lineages after additional 14 days of differentiation.

FIG. 6A shows a diagram of the human ISL1-βgeo BAC transgenic construct. A βgeo cassette and an FRT-flanked antibiotics cassette are inserted into ISL1 endogenous translation start site.

FIGS. 7A-7B show the gene expression of the human ISL1-cre DsRed ES cells and KDR staining in the human fetal hearts. FIG. 7A shows FACS analysis on cells dissociated from day 8EBs of human ISL1-cre DsRed cells and stained with FITC-conjugated anti-KDR antibody. FIG. 7B shows RT-PCR showing gene expression of DsRed+ and DsRed– cells isolated from day 8 EBs of human ISL1-cre DsRed cells. RA; right atrium, LA, left atrium, RCA: right coronary artery, AVC: atrioventricular canal, RV: right ventricle, IAS: intra atrial septum.

FIG. 8A shows 101 colonies/clusters were formed from DsRed+ and eGFP+ cells and are summarized. FIG. 8B shows the number of colonies developed on MEF feeders showing an arithmetically linear relationship to the numbers of input cells. Bars represent mean±s.d.; n=3.

FIG. 9A show ISL1+ cells increased by BIO treatment. Day 6 EBs of human ISL1-βgeo BAC transgenic cells were dissociated and cultured on mouse CMC feeders for two days before treated with and without BIO for another five days. Colonies were stained with anti-ISL1 antibody and counted for ISL1+ ones. FIG. 9B shows qPCR showing the geneexpression of Wnt3a-expanded DsRed+ cells. Cells dissociated from day 7 EBs of human ISL1-cre DsRed cells were plated on Wnt3a-secreting feeders, cultured for five days and FACS isolated. Gene expression of DsRed+ cells was compared with DsRed– cells. Bars represent mean±s.d.; n=3.

FIG. 10A shows an outline of the protocol used for the differentiation of human ESCs to cardiac linage. FIG. 10B shows immunostaining analysis of the day 6 KDR$^{Low}$/c-kit$^{neg}$ derived population cultured in the presence of VEGF (10 ng/ml), DKK1 (150 ng/ml) and bFGF (10 ng/ml), showing CD31 and cTNT and SMHC immunostaining, demonstrating that human ESC-derived ISL1+ progenitors can differentiate into all three cardiovascular lineages in vitro. FIG. 10C is a light photomicrograph showing human specific anti-pecam (CD31) antibody staining visualized with DAB. Note: FIGS. 10A-10C is background and shows prior-art (see Yang et al., 2008, Nature; 453, 524-528) and not claimed in the invention.

FIG. 11 shows flow cytometric analysis of different aged embryoid bodies, demonstrating the development of three distinct populations; KDR$^{high}$c-kit$^+$ (III), KDR$^{Low}$/c-kit$^{neg}$ (I), and KDR$^{neg}$/c-kit$^+$ (II) defined by co-expression of KDR and C-KIT. Note: FIG. 12 is background and shows s prior-art (see Yang et al., 2008, Nature; 453, 524-528) and not claimed in the invention.

FIG. 12A shows the protocol for implantation of mouse embryonic progenitors (E9.5-10.5) derived from isl-1-crexrosa-YFP mouse into the kidney capule of mice. FIG. 12B shows generation of mouse vascularized cardiac tissue after implantation of mouse ISL1+ primordial cells into a mouse kidney capsule.

FIG. 13A shows low magnification of the implanted mouse ISL1+ primordial progenitors, which are enlarged in FIGS. 13B and 13C.

FIG. 14A shows the protocol for implantation of human EB (D8) derived from the H9 Isl1-Cre-REP ES cell line into the kidney capsule of mice. FIG. 14B shows the expression of cardiovascular differentiation markers of the human ISL1+ primordial progenitors prior to implantation. The values on the left are negative controls. The values on the right are from human ISL1+ primordial progenitors derived from ES cells prior to implantation showing expression of ISL1+, but no expression of NKX2.5, GATA4, cTNT, SM22, CD31 or KDR demonstrating the human ISL1+ primordial progenitors have not begun differentiation prior to implantation into the mouse kidney capsule.

FIGS. 15A and 15B are immunohistochemistry images showing human ISL1+ primordial progenitors (e.g. human dsRed+ sorted cells (hEBD8)) are successfully engrafted 2 weeks after implantation into the kidney capsule. FIGS. 15C and 15D are high magnification images of FIGS. 15A and 15B respectively, and show the human ISL1+ primordial progenitors (small cells) surrounded by the mouse kidney cells (large darker cells).

FIGS. 16A-16C show promotion of vasculargenic commitment of human ES cells into human Isl1+/CD31+ cells by contacting with VEGF, between Day 4 and Day 22 (D4-D22) or ALK5 inhibitor between day 7 and day 22 (D7-D22). When Isl1+ is expressed in this ES cell line, the cells co-express GFP. FIG. 16A shows FACs with anti-CD31 of control treated human ES cells. FIG. 16B shows FACs with anti-CD31 of human ES cells contacted with VEGF and ALK5 inhibitor SB431542. FIG. 16C shows a table of the % of cells which are Isl1+/CD31− (GFP+/CD31−), Isl1−/CD31− (GFP−/CD31−), or Isl1+/CD31+ (GFP+/CD31+). FIG. 16C demonstrates that VEGF and ALK5i promotes the vasculargenic commitment of human ES cells into human Isl1+/CD31+ cells, and also increases the proportion of Isl1−/CD31+ cells.

FIG. 17A shows one embodiments of a protocol to promote the vasculargenic commitment of mouse ES cells into mouse Isl1+/CD31+ cells by contacting with VEGF for about 2 weeks beginning by about D4. FIG. 17B shows another embodiments of a protocol to promote the vasculargenic commitment of mouse ES cells into mouse Isl1+/CD31+ cells by contacting with VEGF for about 2 weeks beginning by about D4 and continuing to D20.

DETAILED DESCRIPTION OF THE INVENTION

Figure 1A:
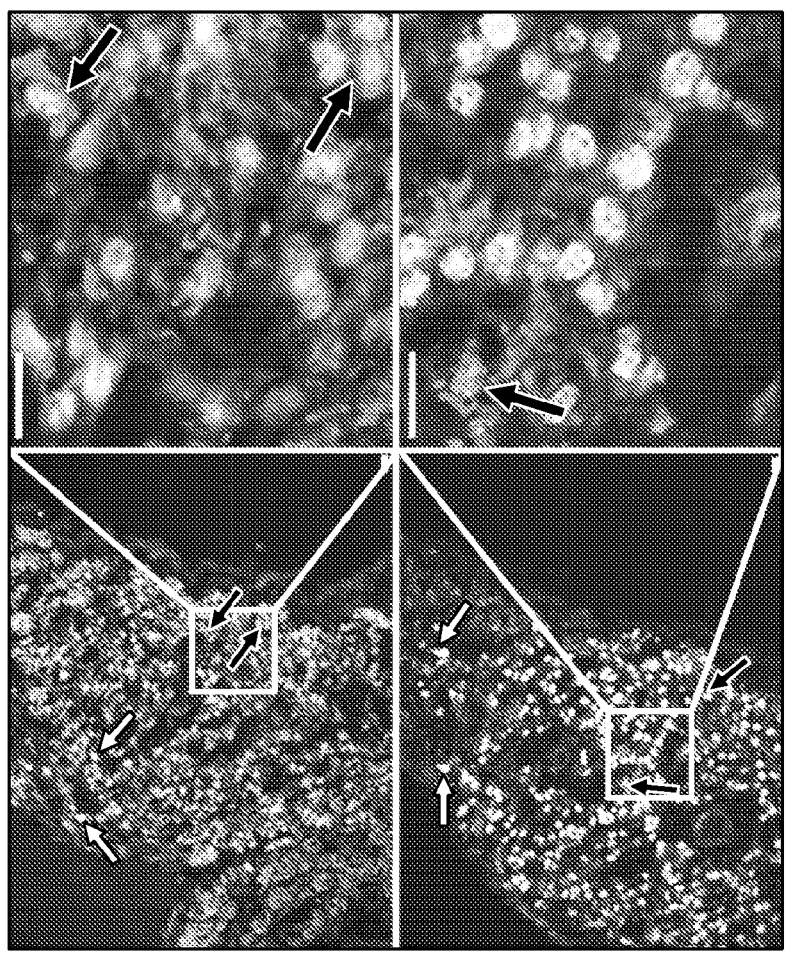
FIGS. 1A-1B show an analysis of the in vivo expression of ISL1 in SHF-derived structures of the human fetal heart. Frozen sections from a human fetal heart at 11 weeks of gestation were stained with indicated antibodies. A scheme shows the plane of the sections and anatomical labels.

The inventors have identified and isolated a human ISL1$^+$ primordial master cardiovascular progenitor cell, identified by the molecular signature of expression of ISL1$^+$, NKX2.5− and KDR− are multipotent cells which give rise to three cell cardiac lineages; smooth muscle cells, endothelial cells and cardiomyocytes.

One aspect of the present invention relates to methods for the differentiation of human primordial ISL1+ progenitors into human cardiovascular vascular progenitors and cardiovascular muscle progenitors. In one embodiment, the agents are reactive to nucleic acids and in another embodiment the agents are reactive to the expression products of the nucleic acids.

In another embodiment, the human Isl1+ progenitors are differentiated along vasculargenic lineages, e.g., to cardiovascular progenitors, where the cells are differentiated into Isl1+/CD31+ cells by contacting the cells with at least one or a combination of the following; VEGF, VEGF homologue, a inhibitor of TGF-β signalling, an ALK5-inhibitor and the like. In some embodiments, the human Isl1+ progenitors are differentiated along vasculargenic lineages to differentiate into Isl1+/CD31+ cells by contacting the cells with at least one or more growth factor, selected from the group comprising; the following; vascular endothelial growth factor (VEGF, including, but not limited to VEGF-165), interleukins, fibroblast growth factors, for example, but not limited to, FGF-1 and FGF-2, hepatocyte growth factor, (HGF), endothelins (such as ET-1, ET-2, and ET-3), insulin-like growth factor (IGF-1), angiopoietins (such as Ang-1, Ang-2, Ang-3/4), angiopoietin-like proteins (such as ANGPTL1, ANGPTL-2, ANGPTL-3, and ANGPTL-4), platelet-derived growth factor (PDGF), including, but not limited to PDGF-AA, PDGF-BB and PDGF-AB, epidermal growth factor (EGF), endothelial cell growth factor (ECGF), including ECGS, platelet-derived endothelial cell growth factor (PD-ECGF), placenta growth factor (PLGF), and the like. The inventors have discovered herein that contacting a population of human Isl1+ primordial progenitors with VEGF or homologues thereof, such as VEGF$_{165}$ increases the efficiency of differentiation along vasculargenic lineages by about at least 1.5-fold, or at least about 2-fold as compared to in the absence of a VEGF or homologues thereof, such as VEGF$_{165}$. The inventors have also discovered herein that contacting a population of human Isl1+ primordial progenitors with a TGFβ inhibitor, for example, a ALK5i increases the efficiency of differentiation along vasculargenic lineages by about at least about 2-fold, or at least about 3-fold, or at least about 4-fold, or at least about 5-fold or at least about 6-fold or more as compared to in the absence of a TGFβ inhibitor, for example, a ALK5i.

The inventors have previously discovered in mice, a multipotent ISL1+ (Islet 1 expressing) cardiovascular progenitor (MICPs) cell which is capable of contributing to all of the major cell types in the mouse heart. In mice, these multipotent embryonic ISL1+ cells were identified to express the three markers Isl1+, Nkx2.5+ and Flk+. Herein, the inventors have discovered a new diverse set of upstream progenitors which are human ISL1+ cardiovascular progenitors which are multipotent and are ISL1+, but in contrast to the multipotent ISL1+ progenitors (MICPs), these human Isl1+ cardiovascular progenitors express ISL1+ do not express either NKX2.5 or KDR (the human ortholog of Flk). The inventors demonstrate that these human ISL1+/NKX2.5−/KDR− cells (herein terms "Isl1+ primordial progenitors") can give rise to downstream MICPs that are Isl1+, Nkx2.5+ and Flk+. The inventors also demonstrate that in humans, these ISL1+/NKX2.5−/KDR− Isl1+ primordial progenitors are present in the right atrium and outflow tract of the developing human heart. Using transgenic and gene-targeting techniques applied to human embryonic stem cell lines, the inventors demonstrate methods to isolate and purify populations of these ISL1+ primordial progenitors, and these ISL1+ primordial progenitors are capable of self-renewal and expansion prior to differentiation into the three major cell types in the heart—the cardiomyocytes, smooth muscle and endothelia. The inventors discovery has relevance for the production of human models for cardiovascular disease and potentially for human cardiac regenerative medicine, as well as use in screening (e.g. drug screening) assays to identify agents with potentially cardiotoxic effects on human ISL1+ primordial progenitors and/or agents which modulate (e.g. increase or decrease) the differentiation of human ISL1+ primordial progenitors into the three different cell types in the heart (e.g. the cardiomyocytes, smooth muscle and endothelia) as well as agents which modulate (e.g. increase or decrease) contractibility of the ISL1+ primordial progenitors.

One aspect of the present invention relates to the use of human primordial ISL1+ progenitors to generate functional vascularized human cardiac tissue in vivo. In one embodiment, the human primordial ISL1+ progenitors are implanted into a subject, where they spontaneously differentiate into human smooth muscle progenitors, epithelial progenitors and cardiomyocyte progenitors, which further differentiate into smooth muscle tissue, vascular tissue and cardiac muscle respectively. In some embodiments, where a population of human primordial ISL1+ progenitors are implanted into a subject, some cells within the population will differentiate along cardiomyocyte lineages, some will differentiate along endothelial lineages and some along smooth muscle lineages. Accordingly, one aspect of the present invention relates to the use of human primordial ISL1+ progenitors to generate a functional three-dimensional vascularized cardiac tissue in vivo.

In some embodiments, the human ISL1+ progenitors are implanted into a subject, for example a human, for example for therapeutic purposes, or an animal subject. In some embodiment, human ISL1+ progenitors can be implanted into any suitable location in a subject, for example but not limited to, a kidney such as a kidney capsule, heart, ascites, peritoneal cavity, pericardium, epicardium, on the surface of the heart, in a pericardial space, and the like. In some embodiments, a population of human ISL1+ progenitors are encapsulated in a bioreactor bag, which can be implanted into a subject at a suitable location, for example on the surface of the heart, subcutaneously or the like. In some embodiments, a population of ISL1+ primordial progenitors are implanted into the subject, such as an animal subject (e.g. for the generation of an in vivo humanized model of vascular disease) at locations such as, for example but not limited to; kidney capsule, peritoneal cavity, liver, ascites, pericardium, epicardium, pericardial space, heart, on the surface of the heart, subcutaneous space.

In some embodiments where human ISL1+ progenitors are implanted into an animal subject, the animal can be use as an in vivo humanized model of vascular disease. For example, an animal model which comprises functional vascularized human cardiac tissue, can be used to screen for agents which affect any one, or a combination of viability, functionality, contractibility, differentiation of the human cardiac tissue.

Accordingly, one embodiment relates to the use of an in vivo humanized model of vascular disease as an assay, for example to assess drug toxicity (e.g. cardiotoxicity) on human heart tissue in vivo (e.g. to identify agents which increase apoptosis, decrease viability, modulate (e.g. increase or decrease by a statistically significantly amount) contractibility and/or conductivity of heart tissue). In some embodiments, the drugs and/or compounds can be existing drugs or compounds, and in other embodiments, the drugs or compounds can be new or modified drugs and compounds.

In another embodiments, an in vivo humanized model of vascular disease can be used as an assay for example to identify agents which increase and decrease coronary blood flow to human vascularized heart tissue in vivo. For example, in one embodiment, the human vascularized heart tissue could be given atherosclerosis, for example by implanting the human ISL1+ progenitors into a LDR −/− mouse and feeding the mouse a high fat diet.

Another aspect of the invention relates use of the in vivo humanized model of vascular disease as disclosed herein to screen for agents, for example molecules and genes involved in biological events. In such an embodiment, the biological event is an event that affects the differentiation of a human ISL1+ progenitor, or the function of the human vascularized cardiac tissues. The in vivo humanized model of vascular disease can be used to identify any agent which promotes the differentiation, proliferation, survival, regeneration, maintenance of the undifferentiated state of the ISL1+ progenitor, and/or inhibition or down-regulation of differentiation.

Another embodiment relates to the therapeutic use of human primordial ISL1+ progenitors, for example, in one embodiment the invention provides methods for the treatment cardiovascular disorders and/or congenital heart disease in a subject comprising transplanting into subjects vascularized human heart tissue generated in vivo from human primordial ISL1+ progenitors.

In another aspect of the invention, the methods provide use vascularized human cardiac tissue produced in vivo from the transplantation of human ISL1+ progenitors into a subject by the methods as disclosed herein. In one embodiment, the vascularized human cardiac tissue can be used for the production of a pharmaceutical composition, for the use in transplantation into subjects in need of cardiac tissue transplantation, for example but not limited to subjects with congenital and/or acquired heart disease and/or subjects with vascular diseases. In one embodiment, human ISL1+ progenitors used to produced the vascularized human cardiac tissue can be genetically modified. In another aspect, the subject can have or be at risk of heart disease and/or vascular disease. In some embodiments, the human ISL1+ progenitors used to produced the vascularized human cardiac tissue can be autologous and/or allogenic. In some embodiments, the human ISL1+ progenitors used to produced the vascularized human cardiac tissue for transplanted are immunogenetically matched to the transplant receipt (e.g. blood type and HLA matched).

DEFINITIONS

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein, the term "Isl1" refers to the nucleic acid encoding Islet 1 gene and homologues thereof, including conservative substitutions, additions, deletions therein not adversely affecting the structure of function. Isl1 is referred in the art as Islet 1, ISL LIM homeobox 1 or Isl-1. Human Isl1 is encoded by nucleic acid corresponding to GenBank Accession No: BC031213 or NM_002202 and the human Isl1 corresponds to protein sequence corresponding to RefSeq ID No: NP_002193.2.

As used herein, the term "Nkx2.5" refers to the nucleic acid encoding NK2 transcription factor related, locus 5 (Drosophila) gene and homologues thereof, including conservative substitutions, additions, deletions therein not adversely affecting the structure of function. Nkx2.5 is referred in the art as CSX, NKX2E CSX1, NKX2.5, NKX4-1. Human Nkx2.5 is encoded by nucleic acid corresponding to GenBank Accession No: AB021133 or NM_004387 and the human Nkx2.5 corresponds to protein sequence corresponding to RefSeq ID No: P52952.

As used herein, the term "flk1" refers to the nucleic acid encoding Vascular endothelial growth factor receptor 2 also known as the KDR kinase insert domain receptor (a type III receptor tyrosine kinase) gene and homologues thereof, including conservative substitutions, additions, deletions therein not adversely affecting the structure of function. Flk1 is referred in the art as FLK1, VEGFR, VEGFR2, CD309. Human flk1 is encoded by nucleic acid corresponding to GenBank Accession No: AF035121 or NM_002253 and the human KDR corresponds to protein sequence corresponding to RefSeq ID No: P35968.

The term "ISL1+ progenitor" or "primordial ISL1+ progenitor" or "ISL1+ primordial progenitor" are used interchangeably herein and refer to a pluripotent stem cell which is positive for Islet 1 expression (Isl1+) and negative for expression of Nkx2.5 and/or KDR expression In some embodiments, a primordial ISL1+ progenitor are negative for markers SCA−, C-KIT− and CD31−. As disclosed herein, a human primordial ISL1+ progenitor is the precursor cell (e.g. gives rise to) a secondary heart field (SHF) progenitors and first heart field (FHF) progenitors. In some embodiments, primordial ISL1+ progenitor give rise to SHF progenitors such as multipotent intermediate progenitors, including multipotent Isl1+ cardiovascular progenitor cells (MICPs) which are Isl1+/Nkx2.5+/KDR+, as disclosed in International Patent WO 2008/054819 which is incorporated herein in its entirety by reference. In some embodiments, primordial ISL1+ progenitor give rise to FHF progenitors, which are Islet1 negative and Nxk2.5 positive (e.g. Isl1−/Nkx2.5+ multipotent and bipotent progenitors)

The term "cardiovascular stem cell" and "cardiac stem cell" are used interchangeably herein, refers to a stem cell which is capable of proliferation and giving rise to more progenitor cells having the ability to generate a large number of mother cells that can in turn give rise to differentiated, or differentiable daughter cells which can eventually terminally differentiate into cardiac cells, cardiovascular cells and other cells of the cardio-vascular system.

As used herein, the term "stem cells" is used in a broad sense and includes traditional stem cells, progenitor cells, preprogenitor cells, reserve cells, and the like. The term "stem cell" or "progenitor" are used interchangeably herein, and refer to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one embodiment, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation".

Exemplary stem cells include embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. Descriptions of stem cells, including method for isolating and culturing them, may be found in, among other places, Embryonic Stem Cells, Methods and Protocols, Turksen, ed., Humana Press, 2002; Weisman et al., Annu. Rev. Cell. Dev. Biol. 17:387 403; Pittinger et al., Science, 284:143 47, 1999; Animal Cell Culture, Masters, ed., Oxford University Press, 2000; Jackson et al., PNAS 96(25):14482 86, 1999; Zuk et al., Tissue Engineering, 7:211 228, 2001 ("Zuk et al."); Atala et al., particularly Chapters 33 41; and U.S. Pat. Nos. 5,559,022, 5,672,346 and 5,827,735. Descriptions of stromal cells, including methods for isolating them, may be found in, among other places, Prockop, Science, 276:7174, 1997; Theise et al., Hepatology, 31:235 40, 2000; Current Protocols in Cell Biology, Bonifacino et al., eds., John Wiley & Sons, 2000 (including updates through March, 2002); and U.S. Pat. No. 4,963,489. The skilled artisan will understand that the stem cells and/or stromal cells selected for inclusion in a transplant with mixed SVF cells or SVF-matrix construct (e.g. for encapsulating a tissue or cell transplant according to the constructs and methods as disclosed herein) are typically appropriate for the intended use of that construct.

The term "progenitor cell" is used herein to refer to cells that have a cellular phenotype that is more primitive (e.g., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

As indicated above, there are different levels or classes of cells falling under the general definition of a "stem cell." These are "totipotent," "pluripotent" and "multipotent" stem cells. The term "totipotent" refers to a stem cell that can give rise to any tissue or cell type in the body. "Pluripotent" stem cells can give rise to any type of cell in the body except germ line cells. Stem cells that can give rise to a smaller or limited number of different cell types are generally termed "multipotent." Thus, totipotent cells differentiate into pluripotent cells that can give rise to most, but not all, of the tissues necessary for fetal development. Pluripotent cells undergo further differentiation into multipotent cells that are committed to give rise to cells that have a particular function. For example, multipotent hematopoietic stem cells give rise to the red blood cells, white blood cells and platelets in the blood.

The term "pluripotent" as used herein refers to a cell with the capacity, under different conditions, to differentiate to cell types characteristic of all three germ cell layers (endoderm, mesoderm and ectoderm). Pluripotent cells are characterized primarily by their ability to differentiate to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. In some embodiments, a pluripotent cell is an undifferentiated cell.

The term "pluripotency" or a "pluripotent state" as used herein refers to a cell with the ability to differentiate into all three embryonic germ layers: endoderm (gut tissue), mesoderm (including blood, muscle, and vessels), and ectoderm (such as skin and nerve), and typically has the potential to divide in vitro for a long period of time, e.g., greater than one year or more than 30 passages.

The term "multipotent" when used in reference to a "multipotent cell" refers to a cell that is able to differentiate into some but not all of the cells derived from all three germ layers. Thus, a multipotent cell is a partially differentiated cell. Multipotent cells are well known in the art, and examples of muiltipotent cells include adult stem cells, such as for example, hematopoietic stem cells and neural stem cells. Multipotent means a stem cell may form many types of cells in a given lineage, but not cells of other lineages. For example, a multipotent blood stem cell can form the many different types of blood cells (red, white, platelets, etc. . . . ), but it cannot form neurons.

The term "multipotency" refers to a cell with the degree of developmental versatility that is less than totipotent and pluripotent.

The term "totipotency" refers to a cell with the degree of differentiation describing a capacity to make all of the cells in the adult body as well as the extra-embryonic tissues including the placenta. The fertilized egg (zygote) is totipotent as are the early cleaved cells (blastomeres)

The term "embryonic stem cell" or "ES cell" or "ESC" are used interchangeably herein and refer to the pluripotent stem cells of the inner cell mass of the embryonic blastocyst (see U.S. Pat. Nos. 5,843,780, 6,200,806, which are incorporated herein by reference). Such cells can similarly be obtained from the inner cell mass of blastocysts derived from somatic cell nuclear transfer (see, for example, U.S. Pat. Nos. 5,945, 577, 5,994,619, 6,235,970, which are incorporated herein by reference). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like. In some embodiments, an ES cell can be obtained without destroying the embryo, for example, without destroying a human embryo.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. Exemplary adult stem cells include neural stem cells, neural crest stem cells, mesenchymal stem cells, hematopoietic stem cells, and pancreatic stem cells. As indicated above, stem cells have been found resident in virtually every tissue. Accordingly, the present invention appreciates that stem cell populations can be isolated from virtually any animal tissue.

As used herein, the terms "iPS cell" and "induced pluripotent stem cell" are used interchangeably and refers to a pluripotent cell artificially derived (e.g., induced by complete or partial reversal) from an undifferentiated cell (e.g. a non-pluripotent cell) or a somatic cell such as a differentiated somatic cell. iPS cells are capable of self-renewal and differentiation into cell fate-committed stem cells, including neural stem cells, as well as various types of mature cells.

The term "derived from" used in the context of a cell derived from another cell means that a cell has stemmed (e.g. changed from or produced by) a cell which is a different cell type. In some instances, for e.g. a cell derived from an iPS cell refers to a cell which has differentiated from an iPS cell. Alternatively, a cell can be converted from one cell type to a different cell type by a process referred to as transdifferention or direct reprogramming. Alternatively, in the terms of iPS cells, a cell (e.g. iPS cell) can be derived from a differentiated cell by a process referred to in the art as dedifferentiation or reprogramming. The term "derived from" also refers to cells which have been differentiated from a progenitor cell. By way of an example, MICPs (multipotent Isl1+ cardiovascular progenitors) are derived from their precursor cell which is an ISL1+ primordial progenitor cell.

By "conditioned medium" is meant, a medium that is altered as compared to a base medium. For example, the conditioning of a medium may cause molecules, such as nutrients and/or growth factors, e.g., VEGF or TGFβ inhibitors such as ALK5i, to be added to or depleted from the original levels found in the base medium. In some embodiments, a medium is conditioned by allowing cells of certain types to be grown or maintained in the medium under certain conditions for a certain period of time. For example, a medium can be conditioned by allowing Isl1+ primordial progenitors to be expanded, differentiated or maintained in a medium of defined composition at a defined temperature for a defined number of hours. As will be appreciated by those of skill in the art, numerous combinations of cells, media types, durations and environmental conditions can be used to produce nearly an infinite array of conditioned media.

When used in connection with cell cultures and/or cell populations, the term "portion" means any non-zero amount of the cell culture or cell population, which ranges from a single cell to the entirety of the cell culture or cells population. In some embodiments, the term "portion" means at least about 0.5% or at last about 1% or at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94% or at least 95% of the cell culture or cell population.

With respect to cells in cell cultures or in cell populations, the term "substantially free of" means that the specified cell type of which the cell culture or cell population is free, is present in an amount of less than about 10%, less than about 9%, less than about 8%, less than about 7%, less than about 6%, less than about 5%, less than about 4%, less than about 3%, less than about 2% or less than about 1% of the total number of cells present in the cell culture or cell population.

As used herein, "exogenously added," compounds such as growth factors, differentiation factors, and the like, in the context of cultures or conditioned media, refers to growth factors that are added to the cultures or media to supplement any compounds or growth factors that may already be present in the culture or media. For example, in some embodiments, of the present invention, cells cultures and or cell populations do not include an exogenously-added retinoid.

As used herein, "produced from hESCs," "derived from hESCs," "differentiated from hESCs" and equivalent expressions refer to the production of a differentiated cell type from hESCs in vitro rather than in vivo.

As used herein, Isl1+/CD31+ vasculargenic progenitors "produced from Isl1+ primordial progenitors" or "differentiated from Isl1+ primordial progenitors" and equivalent expressions refer to the production of a differentiated cell type from Isl1+ primordial progenitors either in vitro or in vivo.

The term "reprogramming" as used herein refers to a process that alters or reverses the differentiation state of a differentiated cell (e.g. a somatic cell). Stated another way, reprogramming refers to a process of driving the differentiation of a cell backwards to a more undifferentiated or more primitive type of cell. The cell to be reprogrammed can be either partially or terminally differentiated prior to reprogramming. In some embodiments, reprogramming encompasses complete reversion of the differentiation state of a differentiated cell (e.g. a somatic cell) to a pluripotent state. In some embodiments, reprogramming also encompasses partial reversion of the differentiation state of a differentiated cell (e.g. a somatic cell) to a multipotent state. In some embodiments, reprogramming encompasses complete or partial reversion of the differentiation state of a differentiated cell (e.g. a somatic cell) to an undifferentiated cell. Reprogramming also encompasses partial reversion of the differentiation state of a somatic cell to a state that renders the cell more susceptible to complete reprogramming to a pluripotent state when subjected to additional manipulations such as those described herein. Such contacting may result in expression of particular genes by the cells, which expression contributes to reprogramming. In certain embodiments of the invention, reprogramming of a differentiated cell (e.g. a somatic cell) causes the differentiated cell to assume an undifferentiated state (e.g. is an undifferentiated cell). In some embodiments, reprogramming of a differentiated cell (e.g. a somatic cell) causes the differentiated cell to assume a pluripotent-like state. The resulting cells are referred to herein as "reprogrammed cells", or "chemically induced reprogrammed cells" or "undifferentiated cells".

Reprogramming involves alteration, e.g., reversal, of at least some of the heritable patterns of nucleic acid modification (e.g., methylation), chromatin condensation, epigenetic changes, genomic imprinting, etc., that occur during cellular differentiation as a zygote develops into an adult. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent, although the compositions and methods of the invention may also be of use for such purposes. Certain of the compositions and methods of the present invention contribute to establishing the pluripotent state. The methods may be practiced on cells that fully differentiated and/or restricted to giving rise only to cells of that particular type, rather than on cells that are already multipotent or pluripotent.

The term "reprogrammed cell" as used herein refers to a cell which has been reprogrammed from a differentiated cell according to the methods as disclosed herein. In some embodiments, a reprogrammed cell is a cell which has undergone epigenetic reprogramming. The term "reprogrammed cell" encompasses an undifferentiated cell. The term "reprogrammed cell" also includes a partially reprogrammed cell except where it specifically indicates it does not include a partially reprogrammed cell.

The term "partially reprogrammed cell" as referred to herein refers to a cell which has been reprogrammed from a differentiated cell, by the methods as disclosed herein, wherein the partially reprogrammed cell has not been completely reprogrammed to pluripotent state but rather to a non-pluripotent stable intermediate state. A partially reprogrammed cell can differentiate into one or two of three germ layers, but cannot differentiate into all three of the germ layers. In some embodiments, a partially reprogrammed cell expresses at least one or at least two or at least three but not all of the following markers; alkaline phosphatase (AP), NANOG, OCT-4, SOX-2, SSEA4, TRA-1-60 or TRA-1-81. In some embodiments, a partially reprogrammed cell expresses markers from one or two germ cell layers, but not markers from all three embryonic germ layers (i.e. a partially reprogrammed cell does not express markers from all three layers of endoderm, mesoderm or ectoderm layers). Markers of endoderm cells include, Gata4, FoxA2, PDX1, Nodal, Sox7 and Sox17. Markers of mesoderm cells include, Brachycury, GSC, LEF1, Mox1 and Tie1. Markers of ectoderm cells include criptol, EN1, GFAP, Islet 1, LIM1 and Nestin. In some embodiments, a partially reprogrammed cell is an undifferentiated cell. In some embodiments, the methods as disclosed herein can be used to generate a partially reprogrammed cell (or population thereof) by contacting a differentiated cell with any compound selected from compounds of Formulas I-XI which replace one or two of the following reprogramming genes selected from the group of; Sox2, Oct3/4 or Klf4.

The term a "reprogramming gene", as used herein, refers to a gene whose expression, contributes to the reprogramming of a differentiated cell, e.g. a somatic cell to an undifferentiated cell, e.g. a cell of a pluripotent state or partially pluripotent state. A reprogramming gene can be, for example, genes encoding transcription factors Sox2, Oct3/4, Klf4, Nanog, Lin-38, c-myc and the like.

As used herein, the term "somatic cell" refers to any cell other than a germ cell, a cell present in or obtained from a pre-implantation embryo, or a cell resulting from proliferation of such a cell in vitro. Stated another way, a somatic cell refers to any cells forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro. Unless otherwise indicated the methods for reprogramming a differentiated cell can be performed both in vivo and in vitro (where in vivo is practiced when an differentiated cell is present within a subject, and where in vitro is practiced using isolated differentiated cell maintained in culture). In some embodiments, where a differentiated cell or population of differentiated cells are cultured in vitro, the differentiated cell can be cultured in an organotypic slice culture, such as described in, e.g., meneghel-Rozzo et al., (2004), Cell Tissue Res, 316(3); 295-303, which is incorporated herein in its entirety by reference.

As used herein, the term "adult cell" refers to a cell found throughout the body after embryonic development.

In the context of cell ontogeny, the adjective "differentiated", or "differentiating" is a relative term. A "differentiated cell" is a cell that has progressed further down the developmental pathway than the cell it is being compared with. Thus, stem cells can differentiate to lineage-restricted precursor cells (such as a mesodermal stem cell), which in turn can differentiate into other types of precursor cells further down the pathway (such as an cardiomyocyte precursor), and then to an end-stage differentiated cell, which plays a characteristic role in a certain tissue type, and may or may not retain the capacity to proliferate further.

The term "differentiation" in the present context means the formation of cells expressing markers known to be associated with cells that are more specialized and closer to becoming terminally differentiated cells incapable of further differentiation. The pathway along which cells progress from a less committed cell, to a cell that is increasingly committed to a particular cell type, and eventually to a terminally differentiated cell is referred to as progressive differentiation or progressive commitment. Cell which are more specialized (e.g., have begun to progress along a path of progressive differentiation) but not yet terminally differentiated are referred to as partially differentiated. Differentiation is a developmental process whereby cells assume a specialized phenotype, e.g., acquire one or more characteristics or functions distinct from other cell types. In some cases, the differentiated phenotype refers to a cell phenotype that is at the mature endpoint in some developmental pathway (a so called terminally differentiated cell). In many, but not all tissues, the process of differentiation is coupled with exit from the cell cycle. In these cases, the terminally differentiated cells lose or greatly restrict their capacity to proliferate. However, we note that in the context of this specification, the terms "differentiation" or "differentiated" refer to cells that are more specialized in their fate or function than at a previous point in their development, and includes both cells that are terminally differentiated and cells that, although not terminally differentiated, are more specialized than at a previous point in their development. The development of a cell from an uncommitted cell (for example, a stem cell), to a cell with an increasing degree of commitment to a particular differentiated cell type, and finally to a terminally differentiated cell is known as progressive differentiation or progressive commitment. A cell that is "differentiated" relative to a progenitor cell has one or more phenotypic differences relative to that progenitor cell. Phenotypic differences include, but are not limited to morphologic differences and differences in gene expression and biological activity, including not only the presence or absence of an expressed marker, but also differences in the amount of a marker and differences in the co-expression patterns of a set of markers.

The term "differentiation" as used herein refers to the cellular development of a cell from a primitive stage towards a more mature (i.e. less primitive) cell.

The term "directed differentiation" as used herein refers to forcing differentiation of a cell from an undifferentiated (e.g. more primitive cell) to a more mature cell type (i.e. less primitive cell) via genetic and/or environmental manipulation. In some embodiments, a reprogrammed cell as disclosed herein is subject to directed differentiation into specific cell types, such as neuronal cell types, muscle cell types and the like.

As used herein, "proliferating" and "proliferation" refers to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation.

The term "regeneration" means regrowth of a cell population, organ or tissue after disease or trauma.

The terms "enriching" or "enriched" are used interchangeably herein and mean that the yield (fraction) of cells of one type is increased by at least 10% over the fraction of cells of that type in the starting culture or preparation.

The terms "renewal" or "self-renewal" or "proliferation" are used interchangeably herein, and refers to a process of a cell making more copies of itself (e.g. duplication) of the cell. In some embodiments, reprogrammed cells are capable of renewal of themselves by dividing into the same undifferentiated cells (e.g. pluripotent or non-specialized cell type) over long periods, and/or many months to years. In some instances, proliferation refers to the expansion of reprogrammed cells by the repeated division of single cells into two identical daughter cells.

The term "lineages" as used herein refers to a term to describe cells with a common ancestry or cells with a common developmental fate, for example cells that are derived from the same ISL1+ primordial progenitor cell or progeny thereof.

As used herein, the term "clonal cell line" refers to a cell lineage that can be maintained in culture and has the potential to propagate indefinitely. A clonal cell line can be a stem cell line or be derived from a stem cell, and where the clonal cell line is used in the context of a clonal cell line comprising stem cells, the term refers to stem cells which have been cultured under in vitro conditions that allow proliferation without differentiation for months to years. Such clonal stem cell lines can have the potential to differentiate along several lineages of the cells from the original stem cell.

The term "media" as referred to herein is a medium for maintaining a tissue or cell population, or culturing a cell population (e.g. "culture media") containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art.

The term "phenotype" refers to one or a number of total biological characteristics that define the cell or organism under a particular set of environmental conditions and factors, regardless of the actual genotype.

A "marker" as used herein describes the characteristics and/or phenotype of a cell. Markers can be used for selection of cells comprising characteristics of interest. Markers will vary with specific cells. Markers are characteristics, whether morphological, functional or biochemical (enzymatic) characteristics particular to a cell type, or molecules expressed by the cell type. Preferably, such markers are proteins, and more preferably, possess an epitope for antibodies or other binding molecules available in the art. However, a marker may consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers may be detected by any method available to one of skill in the art.

The terms "mesenchymal cell" or "mesenchyme" are used interchangeably herein and refer in some instances to the fusiform or satellite cells found between the ectoderm and endoderm of young embryos; most mesenchymal cells are derived from established mesodermal layers, but in the cephalic region they also develop from neural crest or neural tube ectoderm. Mesenchymal cells have a pluripotent capacity, particularly embryonic mesenchymal cells in the embryonic body, developing at different locations into any of the types of connective or supporting tissues, to smooth muscle, to vascular endothelium, and to blood cells.

The term "isolated cell" as used herein refers to a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched from. In some embodiments, the isolated population is an isolated population of reprogrammed cells which is a substantially pure population of reprogrammed cells as compared to a heterogeneous population of cells comprising reprogrammed cells and cells from which the reprogrammed cells were derived.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a population of ISL1+ primordial progenitors, refers to a population of ISL1+ primordial progenitors that contain fewer than about 20%, more preferably fewer than about 15%, 10%, 8%, 7%, most preferably fewer than about 5%, 4%, 3%, 2%, 1%, or less than 1%, of cells that are not ISL1+ primordial progenitors or their progeny as defined by the terms herein. In some embodiments, the present invention encompasses methods to expand a population of ISL1+ primordial progenitors, wherein the expanded population of ISL1+ primordial progenitors is a substantially pure population of ISL1+ primordial progenitors.

The term "in vivo humanized model of vascular disease" refers to a subject, such as an animal which comprises a vascularized cardiac tissue as that term is defined herein. In some embodiments, an in vivo model of humanized vascular disease includes an animal, such as a rodent, monkey or pig, where a substantially pure population of human primordial ISL1+ progenitors has been implanted and differentiated to generate vascularized cardiac tissue. In some embodiments, an in vivo model of humanized vascular disease includes an animal, such as a rodent, monkey or pig, where a substantially pure population of human primordial ISL1+ progenitors, where the human primordial ISL1+ progenitors have been primed to differentiate into vasculargenic lineages, e.g., the Isl1+ progenitors have been contacted with one or more of a VEGF growth factor and/or ALK5i inhibitor prior to implanting into animal model. Stated another way, a in vivo humanized model is an animal comprising human vascularized heart tissue, wherein the human vascularized heart tissue is generated from the differentiation of a population if ISL1+ primordial progenitors along cardiac lineages including cardiomyocyte lineages, endothelial lineages and smooth muscle lineages to generate human vascularized heart tissue in vivo. In some embodiments, the ISL1+ primordial progenitors have been contacted with VEGF or VEGF homologues or ALK5i inhibitors as disclosed herein prior to, or concurrent with the implanting into the animal to increase the effiecncy of differentiation along vascular cardiac lineages.

The term "functional assay" as used herein is a test which assesses the properties of a cell, such as a cell's gene expression or developmental state by evaluating its growth or ability to live under certain circumstances. In some embodiments, a ISL1+ primordial progenitor can be identified by a functional assay to determine the ISL1+ primordial progenitor development and function in the presence of agents.

The term "disease model" as used herein refers to the use of laboratory cell culture or animal research to obtain new information about human disease or illness. In some embodiments, a population of ISL1+ primordial progenitor produced by the methods as disclosed herein can be used in disease modeling experiments.

The term "drug screening" as used herein refers to the use of cells and tissues in the laboratory to identify drugs with a specific function. In some embodiments, the present invention provides drug screening methods of differentiated cells to identify compounds or drugs which reprogram a differentiated cell to a reprogrammed cell (e.g. a reprogrammed cell which is in a pluripotent state or a reprogrammed cell which is a stable intermediate, partially reprogrammed cell, as disclosed herein). In some embodiments, the present invention provides drug screening methods of stable intermediate partially reprogrammed cells to identify compounds or drugs which reprogramming differentiated cells into fully reprogrammed cells (e.g. reprogrammed cells which are in a pluripotent state). In alternative embodiments, the present invention provides drug screening on reprogrammed cells (e.g. human reprogrammed cells) to identify compounds or drugs useful as therapies for diseases or illnesses (e.g. human diseases or illnesses).

The terms "subject" and "individual" are used interchangeably herein, and refer to an animal, for example a human, to whom ISL1+ primordial progenitors and/or human vascularized cardiac tissue as disclosed herein can be implanted into, for e.g. treatment, which in some embodiments encompasses prophylactic treatment or for a disease model, with methods and compositions described herein, is or are provided. For treatment of disease states which are specific for a specific animal such as a human subject, the term "subject" refers to that specific animal. The terms "non-human animals" and "non-human mammals" are used interchangeably herein, and include mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like are also encompassed in the term subject.

The term "tissue" refers to a group or layer of similarly specialized cells which together perform certain special functions. The term "tissue-specific" refers to a source or defining characteristic of cells from a specific tissue.

The term "vascularized cardiac tissue" or "vascularized heart tissue" as referred to herein is a collection of cardiac cells, including different cell types such as cardiomyocytes, endothelial cells and smooth muscle cells which have all differentiated from a population of human primordial ISL1+ progenitors.

As used herein, the term "donor" refers to a subject to which a organ, tissue or cell to be transplanted is harvested from.

As used herein, the term "recipient" refers to a subject which will receive a transplanted organ, tissue or cell.

The term "graft" as used herein refers to the process whereby a free (unattached) cell, tissue, or organ integrates into a tissue following transplantation into a subject.

The term "allograft" refers to a transplanted cell, tissue, or organ derived from a different animal of the same species.

The term "xenograft" or "xenotransplant" as used herein refers to a transplanted cell, tissue, or organ derived from an animal of a different species. In some embodiments, a xenograft is a surgical graft of tissue from one species to an unlike species, genus or family. By way of an example, a graft from a baboon to a human is a xenograft.

The term "xenotransplantation" refers to the process of transplantation of living cells, tissues or organs from one species to another, such as from pigs to humans.

The term "three-dimensional matrix" or "scaffold" or "matrices" as used herein refers in the broad sense to a composition comprising a biocompatible matrix, scaffold, or the like. The three-dimensional matrix may be liquid, gel, semi-solid, or solid at 25° C. The three-dimensional matrix may be biodegradable or non-biodegradable. In some embodiments, the three-dimensional matrix is biocompatible, or bioresorbable or bioreplacable. Exemplary three-dimensional matrices include polymers and hydrogels comprising collagen, fibrin, chitosan, MATRIGELT™, polyethylene glycol, dextrans including chemically crosslinkable or photocrosslinkable dextrans, processed tissue matrix such as submucosal tissue and the like. In certain embodiments, the three-dimensional matrix comprises allogeneic components, autologous components, or both allogeneic components and autologous components. In certain embodiments, the three-dimensional matrix comprises synthetic or semi-synthetic materials. In certain embodiments, the three-dimensional matrix comprises a framework or support, such as a fibrin-derived scaffold.

The term "biodegradable" as used herein denotes a composition that is not biologically harmful and can be chemically degraded or decomposed by natural effectors (e.g., weather, soil bacteria, plants, animals).

The term "bioresorbable" refers to the ability of a material to be reabsorbed over time in the body (e.g. in vivo) so that its original presence is no longer detected once it has been reabsorbed.

The term "bioreplaceable" as used herein, and when used in the context of an implant, refers to a process where de novo growth of the endogenous tissue replaces the implant material. A bioreplacable material as disclosed herein does not provoke an immune or inflammatory response from the subject and does not induce fibrosis. A bioreplaceable material is distinguished from bioresorbable material in that bioresorbable material is not replaced by de novo growth by endogenous tissue.

The term "contacting" or "contact" as used herein as in connection with contacting a ISL1+ primordial progenitor in vivo, e.g. contacting a ISL1+ progenitor in vivo in an animal (e.g. in vivo humanized model of cardiovascular disease) can comprise administering an agent, optionally in a composition, to a subject comprising the ISL1+ primordial progenitor via an appropriate administration route such that the compound contacts the ISL1+ primordial progenitor in vivo. In some embodiments, the term "contacting" as used herein in connection with contacting an Isl1$^+$ primordial progenitor with a growth factor, e.g., VEGF or VEGF homologue (e.g., including but no limited to VEGF$_{165}$), or a TGFβ inhibitor, e.g., ALK5i as disclosed herein, can be in vitro, for example, in conditioned media or exogenously added agent or growth factor. For example, in some embodiment, term "contacting" can refer to a culture media comprising a growth factor, e.g., VEGF or VEGF homologue, e.g., but no limited to $VEGF_{165}$, or a TGFβ inhibitor, e.g., ALK5i which is present in the culture media and is used to culture a population of ISL1+ primordial progenitor cells to induce and/or enhance their differentiation into vasculargenic Isl1+/CD31+ cells.

As used herein, the terms "administering," "introducing" and "transplanting" are used interchangeably and refer to the placement of the human primordial ISL1+ progenitors, or vascularized human cardiac tissue as described herein into a subject by a method or route which results in at least partial localization of the human primordial ISL1+ progenitors, or vascularized human cardiac tissue at a desired site. The human primordial ISL1+ progenitors, or vascularized human cardiac tissue can be administered by any appropriate route which results in delivery to a desired location in the subject where at least a portion of the human primordial ISL1+ progenitors, or cells comprising the vascularized human cardiac tissue remain viable. The period of viability of the cells after administration to a subject can be as short as a few hours, e.g. twenty-four hours, to a few days, to as long as several years.

The term "modulate" is used consistently with its use in the art, e.g., meaning to cause or facilitate a qualitative or quantitative change, alteration, or modification in a process, pathway, or phenomenon of interest. Without limitation, such change may be an increase, decrease, or change in relative strength or activity of different components or branches of the process, pathway, or phenomenon. A "modulator" is an agent that causes or facilitates a qualitative or quantitative change, alteration, or modification in a process, pathway, or phenomenon of interest.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

The term "substantially" as used herein means a proportion of at least about 60%, or preferably at least about 70% or at least about 80%, or at least about 90%, at least about 95%, at least about 97% or at least about 99% or more, or any integer between 70% and 100%.

The terms "vascularize", "vascularizing", or "vascularization" as used herein refer to providing a functional or substantially functional vascular network to an organ or tissue, particularly an engineered tissue. A functional or substantially functional vascular network is one that perfuses or is capable of perfusing the tissue or organ to meet some or all of the tissue's or organ's nutritional needs, oxygen demand, and waste product elimination needs. A vascular tissue is a natural tissue that is rich in vascular elements, such as microvessels, for example, but without limitation, adipose tissue.

The terms "revascularize", "revascularizing", "neovascularization", or "revascularization" as used herein refer to revising an existing vascular network or establishing a new functional or substantially functional vascular network in a tissue or organ that has an avascular or hypovascular zone, typically due to disease, congenital defect, or injury. Revascularizing such a tissue or organ may result in restored or augmented function.

The terms "enhance vascularization" as used herein refers to an increase or acceleration in the rate of formation of a vascularized network. In some embodiments, an enhanced vascularization refers to the formation of a more dense capillary or vascularized network as compared to in the absence of the method (e.g. the vascularization which would occur in the absence of population of SVF cells). Stated another way, an enhancement in vascularization refers to a statistically significant increase in the rate of formation of a vascularized network, or alternatively a statistically significant increase in the amount of capillary which form the vascularized network.

The term "genetically modified" cell, e.g. a genetically modified ISL1+ primordial progenitor as used herein refers to a ISL1+ primordial progenitor into which an exogenous nucleic acid has been introduced by a process involving the hand of man (or a descendant of such a cell that has inherited at least a portion of the nucleic acid). The nucleic acid may for example contain a sequence that is exogenous to the cell, it may contain native sequences (e.g., sequences naturally found in the cells) but in a non-naturally occurring arrangement (e.g., a coding region linked to a promoter from a different gene), or altered versions of native sequences, etc. The process of transferring the nucleic into the cell is referred to as "transducing a cell" and can be achieved by any suitable technique. Suitable techniques include calcium phosphate or lipid-mediated transfection, electroporation, and transduction or infection using a viral vector. In some embodiments the polynucleotide or a portion thereof is integrated into the genome of the cell. The nucleic acid may have subsequently been removed or excised from the genome, provided that such removal or excision results in a detectable alteration in the cell relative to an unmodified but otherwise equivalent cell.

The term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "selectable marker" refers to a gene, RNA, or protein that when expressed, confers upon cells a selectable phenotype, such as resistance to a cytotoxic or cytostatic agent (e.g., antibiotic resistance), nutritional prototrophy, or expression of a particular protein that can be used as a basis to distinguish cells that express the protein from cells that do not. Proteins whose expression can be readily detected such as a fluorescent or luminescent protein or an enzyme that acts on a substrate to produce a colored, fluorescent, or luminescent substance ("detectable markers") constitute a subset of selectable markers. The presence of a selectable marker linked to expression control elements native to a gene that is normally expressed selectively or exclusively in pluripotent cells makes it possible to identify and select somatic cells that have been reprogrammed to a pluripotent state. A variety of selectable marker genes can be used, such as neomycin resistance gene (neo), puromycin resistance gene (puro), guanine phosphoribosyl transferase (gpt), dihydrofolate reductase (DHFR), adenosine deaminase (ada), puromycin-N-acetyl-transferase (PAC), hygromycin resistance gene (hyg), multidrug resistance gene (mdr), thymidine kinase (TK), hypoxanthine-guanine phosphoribosyltransferase (HPRT), and hisD gene. Detectable markers include green fluorescent protein (GFP) blue, sapphire, yellow, red, orange, and cyan fluorescent proteins and variants of any of these. Luminescent proteins such as luciferase (e.g., firefly or *Renilla* luciferase) are also of use. As will be evident to one of skill in the art, the term "selectable marker" as used herein can refer to a gene or to an expression product of the gene, e.g., an encoded protein.

In some embodiments the selectable marker confers a proliferation and/or survival advantage on cells that express it relative to cells that do not express it or that express it at significantly lower levels. Such proliferation and/or survival advantage typically occurs when the cells are maintained under certain conditions, e.g., "selective conditions". To ensure an effective selection, a population of cells can be maintained for a under conditions and for a sufficient period of time such that cells that do not express the marker do not proliferate and/or do not survive and are eliminated from the population or their number is reduced to only a very small fraction of the population. The process of selecting cells that express a marker that confers a proliferation and/or survival advantage by maintaining a population of cells under selective conditions so as to largely or completely eliminate cells that do not express the marker is referred to herein as "positive selection", and the marker is said to be "useful for positive selection". Negative selection and markers useful for negative selection are also of interest in certain of the methods described herein. Expression of such markers confers a proliferation and/or survival disadvantage on cells that express the marker relative to cells that do not express the marker or express it at significantly lower levels (or, considered another way, cells that do not express the marker have a proliferation and/or survival advantage relative to cells that express the marker). Cells that express the marker can therefore be largely or completely eliminated from a population of cells when maintained in selective conditions for a sufficient period of time.

The term "transduction" as used herein refers to the use of viral particles to introduce new genetic material into a cell The term "transfection" as used herein refers the use of chemical methods, most often lipid containing vesicles, to introduce new genetic material into a cell The term "transformation" as used herein refers to when a cell becomes functionally abnormal in the process of malignancy, often obtaining a new capacity to multiply indefinitely or under new circumstances.

As used herein, "protein" is a polymer consisting essentially of any of the 20 amino acids. Although "polypeptide" is often used in reference to relatively large polypeptides, and "peptide" is often used in reference to small polypeptides, usage of these terms in the art overlaps and is varied. The terms "peptide(s)", "protein(s)" and "polypeptide(s)" are used interchangeably herein.

The term "wild type" refers to the naturally-occurring polynucleotide sequence encoding a protein, or a portion thereof, or protein sequence, or portion thereof, respectively, as it normally exists in vivo.

The term "mutant" refers to any change in the genetic material of an organism, in particular a change (i.e., deletion, substitution, addition, or alteration) in a wild-type polynucleotide sequence or any change in a wild-type protein sequence. The term "variant" is used interchangeably with "mutant". Although it is often assumed that a change in the genetic material results in a change of the function of the protein, the terms "mutant" and "variant" refer to a change in the sequence of a wild-type protein regardless of whether that change alters the function of the protein (e.g., increases, decreases, imparts a new function), or whether that change has no effect on the function of the protein (e.g., the mutation or variation is silent). The term mutation is used interchangeably herein with polymorphism in this application.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. The terms "polynucleotide sequence" and "nucleotide sequence" are also used interchangeably herein.

As used herein, the term "gene" or "recombinant gene" refers to a nucleic acid comprising an open reading frame encoding a polypeptide, including both exon and (optionally) intron sequences.

A "reporter gene" as used herein encompasses any gene that is genetically introduced into a cell that adds to the phenotype of the stem cell. Reporter genes as disclosed in this invention are intended to encompass fluorescent, enzymatic and resistance genes, but also other genes which can easily be detected by persons of ordinary skill in the art. In some embodiments of the invention, reporter genes are used as markers for the identification of particular stem cells, cardiovascular stem cells and their differentiated progeny.

The term "recombinant," as used herein, means that a protein is derived from a prokaryotic or eukaryotic expression system.

As used herein, the term "vector" refers to a nucleic acid molecule capable of transporting another nucleic acid to which it has been linked. Preferred vectors are those capable of autonomous replication and/or expression of nucleic acids to which they are linked. Vectors capable of directing the expression of genes to which they are operatively linked are referred to herein as "expression vectors".

The term "viral vectors" refers to the use as viruses, or virus-associated vectors as carriers of the nucleic acid construct into the cell. Constructs may be integrated and packaged into non-replicating, defective viral genomes like Adenovirus, Adeno-associated virus (AAV), or Herpes simplex virus (HSV) or others, including reteroviral and lentiviral vectors, for infection or transduction into cells. The vector may or may not be incorporated into the cells genome. The constructs may include viral sequences for transfection, if desired. Alternatively, the construct may be incorporated into vectors capable of episomal replication, e.g EPV and EBV vectors.

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

The term "regulatory sequence" and "promoter" are used interchangeably herein, refers to a generic term used throughout the specification to refer to nucleic acid sequences, such as initiation signals, enhancers, and promoters, which induce or control transcription of protein coding sequences with which they are operatively linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of a protein.

As used herein, the term "tissue-specific promoter" means a nucleic acid sequence that serves as a promoter, i.e., regulates expression of a selected nucleic acid sequence operably linked to the promoter, and which affects expression of the selected nucleic acid sequence in specific cells of a tissue, such as cells of neural origin, e.g. neuronal cells. The term also covers so-called "leaky" promoters, which regulate expression of a selected nucleic acid primarily in one tissue, but cause expression in other tissues as well.

As used herein, the phrase "cardiovascular condition, disease or disorder" is intended to include all disorders characterized by insufficient, undesired or abnormal cardiac function, e.g. ischemic heart disease, hypertensive heart disease and pulmonary hypertensive heart disease, valvular disease, congenital heart disease and any condition which leads to congestive heart failure in a subject, particularly a human subject. Insufficient or abnormal cardiac function can be the result of disease, injury and/or aging. By way of background, a response to myocardial injury follows a well-defined path in which some cells die while others enter a state of hibernation where they are not yet dead but are dysfunctional. This is followed by infiltration of inflammatory cells, deposition of collagen as part of scarring, all of which happen in parallel with in-growth of new blood vessels and a degree of continued cell death. As used herein, the term "ischemia" refers to any localized tissue ischemia due to reduction of the inflow of blood. The term "myocardial ischemia" refers to circulatory disturbances caused by coronary atherosclerosis and/or inadequate oxygen supply to the myocardium. For example, an acute myocardial infarction represents an irreversible ischemic insult to myocardial tissue. This insult results in an occlusive (e.g., thrombotic or embolic) event in the coronary circulation and produces an environment in which the myocardial metabolic demands exceed the supply of oxygen to the myocardial tissue.

The term "disease" or "disorder" is used interchangeably herein, and refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, indisposition or affection.

The term "pathology" as used herein, refers to symptoms, for example, structural and functional changes in a cell, tissue, or organs, which contribute to a disease or disorder. For example, the pathology may be associated with a particular nucleic acid sequence, or "pathological nucleic acid" which refers to a nucleic acid sequence that contributes, wholly or in part to the pathology, as an example, the pathological nucleic acid may be a nucleic acid sequence encoding a gene with a particular pathology causing or pathology-associated mutation or polymorphism. The pathology may be associated with the expression of a pathological protein or pathological polypeptide that contributes, wholly or in part to the pathology associated with a particular disease or disorder. In another embodiment, the pathology is for example, is associated with other factors, for example ischemia and the like.

As used herein, the term "treating" or "treatment" are used interchangeably herein and refers to reducing or decreasing or alleviating or halting at least one adverse effect or symptom of a cardiovascular condition, disease or disorder, i.e., any disorder characterized by insufficient or undesired cardiac function. Adverse effects or symptoms of cardiac disorders are well-known in the art and include, but are not limited to, dyspnea, chest pain, palpitations, dizziness, syncope, edema, cyanosis, pallor, fatigue and death. In some embodiments, the term "treatment" as used herein refers to prophylactic treatment or preventative treatment to prevent the development of a symptom of a cardiovascular condition in a subject.

The phrases "parenteral administration" and "administered parenterally" as used herein mean modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein mean the administration of cardiovascular stem cells and/or their progeny and/or compound and/or other material other than directly into the cardiac tissue, such that it enters the animal's system and, thus, is subject to metabolism and other like processes, for example, subcutaneous or intravenous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation.

The term "drug" or "compound" as used herein refers to a chemical entity or biological product, or combination of chemical entities or biological products, administered to a subject to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

The term "transplantation" as used herein refers to introduction of new cells (e.g. reprogrammed cells), tissues (such as differentated cells produced from reprogrammed cells), or organs into a host (i.e. transplant recipient or transplant subject)

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Human Primordial ISL1+ Progenitors

In the present invention, a human ISL1+ primordial cardiovascular progenitor has been discovered, isolated and characterized. One aspect of the invention provides methods for the isolation of a human ISL1+ primordial cardiovascular progenitor that are capable of differentiating into multiple different lineages, such as cardiac muscle, endothelial cells and vascular smooth muscle cells.

The inventors have discovered a population of human ISL1+ primordial cardiovascular progenitor cells with multipotent capability which are ISL1+, but surprisingly, in contrast to the same multipotent ISL1+ progenitors in mice (which are ISL1+/NKX2.5+/Flk+), these human Isl1+ cardiovascular progenitors express ISL1+, but do not express either NKX2.5 or KDR (the human ortholog of Flk).

The inventors demonstrate that these ISL1+/NKX2.5–/KDR– cells are present in the right atrium and outflow tract of the developing human heart. The inventors demonstrate that these human ISL1+ primordial cardiovascular progenitors give rise to a family of multipotent intermediate progenitors, including multipotent Isl1+ cardiovascular progenitor cells (MICPs) which are Isl1+/Nkx2.5+/KDR+, as disclosed in International Patent WO 2008/054819 which is incorporated herein in its entirety by reference. Thus, the human ISL1+ primordial progenitors disclosed herein are precursors to the multipotent cardiovascular progenitors which are ISL1+/NKX2.5+/KDR+ (or flk+) as disclosed in WO 2008/054819, which is incorporated herein in its entirety by reference.

As disclosed herein, the inventors have discovered a human ISL1+ primordial cardiovascular stem cell that is capable of differentiating into multiple different lineages. In particular, one aspect of the invention relates to methods for isolating a human ISL1+ primordial cardiovascular stem cell from a population of cells, such as ES cells or pluripotent cells, involving identifying cells where are positive for Islet 1 expression (Isl1+) and negative for expression of Nkx2.5 and/or KDR expression, and isolating and collecting the cells which are positive for islet expression but not for Nkx2.5 or KDR expression (e.g. positive cells which are ISL1+/Nkx2.5–/KDR–) from those cells which are negative for Islet1 expression or express Nkx2.5 and/or KDR (e.g. negative cells which are ISL1–, or ISL+/Nkx2.5+ and/or KDR+). In some embodiments, the human ISL1+ primordial cardiovascular are also negative for one or any combination of the following markers; SCA–, C-KIT– and CD31–, TBX–, MTH6, WT1, α-actinin, cTnT, CD146, CD31–, SM-MHC.

One aspect of the present invention relates to a method for isolating a substantially pure population of human primordial ISL1+ progenitors, the method comprising contacting a population of cells with agents reactive to Islet1, Nkx2.5 and KDR, and separating cells which are positive for ISL1 (ISL1+) and negative for NKX2.5 (NKX2.5–) and KDR (KDR–) from the cells which are negative for ISL1 (ISL1–) reactivity and/or positive for NKX2.5 and/or KDR reactivity.

Another aspect of the present invention relates to a method for isolating a substantially pure population of human primordial ISL1+ progenitors, the method comprising introducing a reporter gene operatively linked to the regulatory sequence of the Islea and/or Nkx2.5 and/or KDR genes, and separating cells which are positive for ISL1 expression (ISL1+) and negative for NKX2.5 expression (NKX2.5−) and KDR (KDR−) expression (e.g. ISL1+/NKX2.5−/KDR− cells) from the cells which are negative for ISL1 (ISL1−) reactivity and/or positive for NKX2.5 and/or KDR reactivity (e.g. ISL1−/NKX2.5+ or ISL1−/NKX2.5− or ISL1−/KDR− or ISL1−/KDR+, or ISL1+/NKX2.5+/KDR+ cells).

In some embodiments, the human primordial ISL1+ progenitors as disclosed herein are capable of differentiating into a plurality of subtypes of human cardiovascular progenitors in vivo, for example but not limited to human cardiovascular vascular progenitors and human cardiovascular muscle progenitors.

In some embodiments, the human ISL1+ progenitors can be identified based on their ability to differentiate into all three lineages cardiomyocyte progenitors, endothelial progenitors, and smooth muscle progenitors. Table 1 shows the marker expression which can be used to identify and isolate the human ISL1+ progenitors, as well as assess their ability to differentiate into three lineages.

In some embodiments, human primordial ISL1+ progenitors can be differentiated into human cardiovascular vascular progenitors which are Islet-1-positive, KDR-positive and Nkx2.5-negative cardiovascular vascular progenitors. In some embodiments, human primordial ISL1+ progenitors can differentiate into human cardiovascular muscle progenitors which are Islet-1-positive, Nkx2.5-positive and KDR-negative cardiovascular muscle progenitors, or Nkx2.5-positive, Islet-1-negative and KDR-negative human cardiovascular muscle progenitors.

In some embodiments, contacting a population of isl1+ primordial progenitor cells (which are Isl1+/Nkx2.5−/KDR−) with a VEGF or a VEGF analogue such as VEGF$_{165}$ or an inhibitor of TGFβ signalling, such as an ALK5 inhibitor is more efficient to differentiate along vasculargenic lineages to Isl1+/CD31+ cells than contacting a population of MICP (which are Isl1+/Nkx2.5+/KDR+) VEGF or a VEGF analogue such as VEGF$_{165}$ or an inhibitor of TGFβ signalling, such as an ALK5 inhibitor. In some embodiments, contacting a population of isl1+ primordial progenitor cells (which are Isl1+/Nkx2.5−/KDR−) with a VEGF or a VEGF analogue such as VEGF$_{165}$ or an inhibitor of TGFβ signalling, such as an ALK5 inhibitor is more efficient, by about at least 1.5-fold, or at least about 2-fold, or at least about 3-fold, or at least about 4-fold, or at least about 5-fold, or at least about 6-fold, or at least about 7-fold, or more than about 7-fold as compared to contacting a population of MICP (which are Isl1+/Nkx2.5+/KDR+) with VEGF or a VEGF analogue such as VEGF$_{165}$ or an inhibitor of TGFβ signalling, such as an ALK5 inhibitor.

One aspect of the present invention relates to a method to increase the efficiency of differentiation of embryonic stem (ES) cells, or human induced pluripotent cells (iPSCs) along vasculargenic lineages by contacting the ES cells or iPSCs with VEGF and/or an inhibitor of the TGFβ signaling pathway, such as an ALK5 inhibitor (ALK5i) or the like. Another aspect of the invention relates to increasing the yield of CD31+ cells differentiated from ES cells and/or iPSCs by culturing the cells in a media comprising VEGF or an ana-

TABLE 1

| | Positive markers | negative markers | other negative markers |
|---|---|---|---|
| human ISL1+ primordial progenitor | ISL1+ | NKX2.5−<br>KDR− | TBX−, MTH6−, WT1−, a-actinin−, cTnT−, CD146−, CD31−, SM-MHC |
| Cardiomyocyte progenitor (e.g. Isl1+ intermediate cardiomyocyte progenitor) | ISL1+/cTNT+ | | |
| Cardiomyocyte | cTNT+ | ISL1− | |
| Endothelial progenitor (e.g. Isl1+ intermediate endothelial progenitor) | ISL1+/CD31+/CD146+ | | |
| endothelial cell | CD31+/CD146+/PECAM+/VE-caderin+ | ISL1− | |
| smooth muscle progenitor (e.g. Isl1+ intermediate SM progenitor) | ISL+/SMMHC+ | | |
| smooth muscle cell | SMMHC+, SMTN+ | ISL1− | |
| Epicardial progenitor | ISL+/WT1+ | | |

In one aspect of the present invention relates to increasing the efficiency of differentiating the human primordial ISL1+ progenitors along vascular lineages by contacting a population of isl1+ primordial progenitor cells with a VEGF or a VEGF analogue such as VEGF$_{165}$ or an inhibitor of TGFβ signalling, such as an ALK5 inhibitor. In some embodiments, contacting a population of isl1+ primordial progenitor cells with a VEGF or a VEGF analogue such as VEGF$_{165}$ or an inhibitor of TGFβ signalling, such as an ALK5 inhibitor increase the efficiency of differentiation along vasculargenic lineages to Isl1+/CD31+ cells by about at least 1.5-fold, or at least about 2-fold, or at least about 3-fold, or at least about 4-fold, or at least about 5-fold, or at least about 6-fold, or at least about 7-fold, or more than about 7-fold as compared to the absence of a VEGF or a VEGF analogue such as VEGF$_{165}$ or an inhibitor of TGFβ signalling, such as an ALK5 inhibitor.

logue or functional homologue thereof, and/or an inhibitor of the TGFβ signaling pathway, such as an ALK5 inhibitor (ALK5i) or the like.

In another embodiment, the human Isl1+ progenitors are differentiated along vasculargenic lineages, e.g., to cardiovascular progenitors, where the cells are differentiated into Isl1+/CD31+ cells by contacting the cells with at least one of the following; VEGF, VEGF homologue, a inhibitor of TGF-β signalling, an ALK5-inhibitor and the like. In some embodiments, the human Isl1+ progenitors are differentiated along vasculargenic lineages to differentiate into Isl1+/CD31+ cells by contacting the cells with at least one or more growth factor, selected from the group comprising; the following; vascular endothelial growth factor (VEGF, including, but not limited to VEGF-165), interleukins, fibroblast growth factors, for example, but not limited to, FGF-1 and FGF-2, hepatocyte growth factor, (HGF), endothelins (such as ET-1, ET-2, and ET-3), insulin-like growth factor (IGF-1), angiopoietins (such as Ang-1, Ang-2, Ang-3/4), angiopoietin-like proteins (such as ANGPTL1, ANGPTL-2, ANGPTL-3, and ANGPTL-4), platelet-derived growth factor (PDGF), including, but not limited to PDGF-AA, PDGF-BB and PDGF-AB, epidermal growth factor (EGF), endothelial cell growth factor (ECGF), including ECGS, platelet-derived endothelial cell growth factor (PD-ECGF), placenta growth factor (PLGF), and the like.

In further embodiments, the human primordial ISL1+ progenitors as disclosed herein are capable of differentiating into human endothelial lineages, myocyte lineages, neuronal lineages, autonomic nervous system progenitors. In some embodiments, human primordial ISL1+ progenitors that have differentiated into endothelial lineages can be identified by endothelial markers, for example but not limited to cells expressing markers PECAM1, KDR, CD31, VE-cadherin, CD146, vWF and other endothelial markers commonly known by persons of ordinary skill in the art.

In some embodiments, human primordial ISL1+ progenitors that have differentiated into human smooth muscle lineages can be identified by smooth muscle markers, for example but not limited to cells expressing markers smooth muscle actin (SMA or SM-actin) or smooth muscle myosin heavy chain (SM-MHC) and response to vasoactive hormone Angotensin II to result in a progressive cytosolic [Ca2+]i increase or other smooth muscle markers commonly known by persons of ordinary skill in the art. For example, human primordial ISL1+ progenitors that have differentiated along human cardiomyocyte lineages can be identified by expressing troponin (TnT), TnT1, α-actinin, atrial natruic factor (ANT), acetylcholinesterase and other cardiomyocyte markers commonly known by persons of ordinary skill in the art.

In some embodiments, the human primordial ISL1+ progenitors as disclosed herein are capable of further differentiating into cells having an autonomic nervous system phenotype; cells having a neural stem cell phenotype, cells having a myocytic phenotype, cells having an endothelial phenotype. For example, cells having neural stem cell phenotype express a neural marker, such as Nestin, Neu, NeuN or other neuronal precursor markers, and cells with myocytic phenotype or myocyte phenotype, or cardiomyocyte phenotype markers such as, but not limited to, ANP (Atrial natriuretic peptide), Arpp, BBF-1, BNP (B-type natriuretic peptide), Caveolin-3 (Cav-3), Connexin-43, Desmin, Dystrophin (Xp21), EGFP, Endothelin-1, Fluoromisonidazole, FABP (Heart fatty-acid-binding protein), GATA-4, GATA-5 MEF-2 (MEF2), MLC2v, Myosin, N-cadherin, Nestin, Popdc2 (Popeye domain containing gene 2), Sarcomeric Actin, Troponin or Troponin I.

In some embodiments, the human primordial ISL1+ progenitors that differentiate along autonomic nervous system lineage have a cardiac autonomic nervous system phenotype, for example express acetylycholinesterase. In some embodiments, the cardiovascular stem cells differentiated along cardiac autonomic cell type have cardiac pace maker phenotype and/or conduction phenotype, and can be identified by markers such as EGFP (Kolossov et al, FASAB J, 2005; 19; 577-579) or other electrical properties of the cells commonly known by persons of ordinary skill in the art.

In one embodiment, the invention relates to a method of isolating populations of cardiovascular stem cells characterized by the markers Isl-1+, Nkx2.5– and KDR– by means of positive selection. The methods described permit enrichment of a purified population or substantially pure population of primordial ISL1+ progenitors expressing Isl-1, but not Nkx2.5 and KDR can be obtained.

In a further embodiment, the human primordial ISL1+ progenitors described herein differentiate into multiple human lineages, for example, lineages including endothelial lineages, myocyte lineages, neuronal lineages, differentiation along autonomic nervous system progenitor pathways etc. Methods for such directed differentiation protocols are well known in the art, and include as a non-limiting example, directed differentiation of cardiovascular stem cells into cardiomyocytes, which can be performed by culturing the cells on fibronectin coated plates in the presence of DMEM/M199 (4:1 ratio) medium containing 10% horse serum and 5% fetal bovine serum (FBS). As a non-limiting example, the cardiovascular stem cells can be directed to differentiate into smooth muscle cells by culturing on fibronectin in the presence of DMEM/F12 media containing B27 media and 2% FBS and 10 ng/ml EGF. As another non-limiting example, the cardiovascular stem cells can be directed to differentiate into endothelial cells by plating on collagenase IV in the presence of DMEM supplemented with 10% FBS and 50 ng/ml mouse VEGF (see Example 6). The cardiovascular stem cells can be differentiated either as a monolayer in culture or on feeder cells.

One important embodiment of the invention encompasses the differentiation of the human primordial ISL1+ progenitors as disclosed herein into human cardiomyocytes linage cells. The human cardiomyocyte lineage cells may be human cardiomyocyte precursor cells, or differentiated human cardiomyocytes. Differentiated human cardiomyocytes include one or more of primary cardiomyocytes, nodal (pacemaker) cardiomyocytes; conduction cardiomyocytes; and working (contractile) cardiomyocytes, which may be of atrial or ventricular type.

As disclosed herein in the Examples, the human primordial ISL1+ progenitors as disclosed herein can differentiate into 3 different lineages in vitro and in vivo; smooth muscle cells (and human smooth muscle cell progenitors), cardiomyocytes (e.g. human cardiomyocyte progenitors) and endothelial cell (e.g. human endothelial progenitors) lineages. As shown in the Examples and FIG. 5, the human primordial ISL1+ progenitors as disclosed herein can differentiate into progenitors co-expressing Isl1$^+$ and CD31 and are a subset of vascular progenitors which can give rise of endothelial and smooth muscle lineages. The identification of cardiovascular stem cells as disclosed herein differentiated into endothelial cells can be identified by expressing markers PECAM1, flk1 (KDR), CD31, VE-cadherin, CD146, vWF.

The identification of human primordial ISL1+ progenitors as disclosed herein which differentiate into smooth muscle cells can be identified by expressing markers smooth muscle actin (SMA or SM-actin) or smooth muscle myosin heavy chain (SM-MHC) and response to vasoactive hormone Angotensin II to result in a progressive cytosolic $[Ca2^+]_i$ increase. The human primordial ISL1+ progenitors can also differentiate into progenitors co-expressing Nkx2.5 but not KDR and can be isl1 and are subset of cardiac progenitors which would serve as restricted cardiac muscle progenitors or cardiomyocytes, and have been demonstrated to differentiate into subsets of cardiomyocytes such as pacemaker, sino-atrial (SA) node and atrial-ventricular (AV) node as identified by acetylcholinesterase (Ach-esterase).

The identification of human primordial ISL1+ progenitors as disclosed herein which have differentiated into human cardiomyocytes can be identified by expressing troponin (cTnT), TnT1, α-actinin, atrial natruic factor (ANT), acetylcholinesterase. In some embodiments, human primordial ISL1+ progenitors as disclosed herein can be induced to differentiate along cardiomyocyte lineages by growing on fibronectin in the presence of DMEM/MM199 (1:4 ratio) in 10% horse serum and 5% FBS, as disclosed in the examples addition of cardiotrophic factors such as those disclosed in U.S. Patent application 2003/0022367 which is incorporated herein by reference, activin A, activin B, IGF, BMPs, FGF, PDGF, LIF, EGF, TGFα, cripto gene and other growth factors known by persons of ordinary skill in the art that can differentiate cells along a cardiac muscle linage.

In some embodiments, the human ISL1+ primordial progenitors differentiate into human cardiomyocyte progenitors. A human "cardiomyocyte progenitor" is defined as a human cell that is capable (without dedifferentiation or reprogramming) of giving rise to progeny that include cardiomyocytes. Such precursors may express markers typical of the lineage, including, without limitation, cardiac troponin I (cTnI), cardiac troponin T (cTnT), sarcomeric myosin heavy chain (MHC), GATA4, Nkx2.5, N-cadherin, beta1-adrenoreceptor (beta1-AR), ANF, the MEF-2 family of transcription factors, creatine kinase MB (CK-MB), myoglobin, or atrial natriuretic factor (ANF). Throughout this disclosure, techniques and compositions that refer to human "cardiomyocytes" or "cardiomyocyte progenitor" can be taken to apply equally to cells at any stage of cardiomyocyte ontogeny without restriction, as defined above, unless otherwise specified. The cells may or may not have the ability to proliferate or exhibit contractile activity. The culture conditions may optionally comprise agents that enhance differentiation to a specific lineage. For example, myocardial lineage differentiation may be promoted by including cardiotrophic agents in the culture, e.g. agents capable of forming high energy phosphate bonds (such as creatine) and acyl group carrier molecules (such as carnitine); and a cardiomyocyte calcium channel modulator (such as taurine). Optionally, cardiotropic factors, including, but not limited to those described in U.S. Patent Application Serial No. 2003/0022367, (which is incorporated herein in its entirety by reference), may be added to the culture. Such factors may include, for example but not limited to nucleotide analogs that affect DNA methylation and alter expression of cardiomyocyte-related genes; TGF-beta ligands, such as activin A, activin B, insulin-like growth factors, bone morphogenic proteins, fibroblast growth factors, platelet-derived growth factor natriuretic factors, insulin, leukemia inhibitory factor (LIF), epidermal growth factor (EGF), TGFalpha, and products of the cripto gene; antibodies, peptidomimetics with agonist activity for the same receptors, pseudo ligands, for example peptides and antibodies, cells secreting such factors, and other methods for directed differentiation of stem cells along specific cell lineages in particular cardiomyocyte lineages.

In some embodiments, cardiovascular cells of invention can differentiate into cells that demonstrate spontaneous periodic contractile activity, whereas others may differentiated into cells with non-spontaneous contractile activity (evoked upon appropriate stimulation). Spontaneous contraction generally means that, when cultured in a suitable tissue culture environment with an appropriate Ca++ concentration and electrolyte balance, the cells can be observed to contract in a periodic fashion across one axis of the cell, and then release from contraction, without having to add any additional components to the culture medium. Non-spontaneous contraction may be observed, for example, in the presence of pacemaker cells, or other stimulus.

Based on morphological and electrophysiological criteria, four main phenotypes of cardiomyocytes that arise during development of the mammalian (e.g. human) heart can be distinguished: primary cardiomyocytes; nodal cardiomyocytes; conducting cardiomyocytes and working cardiomyocytes. Morphologically and functionally, the chamber myocardium of the developing atria and ventricles are distinguished from the primary myocardium of the linear heart tube. The chamber myocardium becomes trabeculated, whereas the primary myocardium is smooth and covered with cardiac cushions. The clearest markers that in mammals identify the developing chamber myocardium are the atrial natriuretic factor (Anf) and Cx40 genes, which are not expressed in the myocardium of the primary heart tube. During further development, the smooth-walled dorsal atrial wall (comprising the pulmonary and caval myocardium) as well as the atrial septa, are incorporated into the atria. These components do not express Anf, but do express Cx40. A gene that is clearly upregulated in the cardiac chambers is sarco-endoplasmic reticulum Ca2+ ATPase (Serca2a), but because it is also expressed in the primary myocardium it is less suited as a marker for the developing chambers. The functional significance of the chamber program of gene expression is that it allows fast, synchronous contractions. All cardiomyocytes have sarcomeres and a sarcoplasmic reticulum (SR), are coupled by gap junctions, and display automaticity. Cells of the primary heart tube are characterized by high automaticity, low conduction velocity, low contractility, and low SR activity. This phenotype largely persists in nodal cells. In contrast, atrial and ventricular working myocardial cells display virtually no automaticity, are well coupled intercellularly, have well developed sarcomeres, and have a high SR activity. Conducting cells from the atrioventricular bundle, bundle branches and peripheral ventricular conduction system have poorly developed sarcomeres, low SR activity, but are well coupled and display high automaticity. For alpha and beta-myosin heavy chain (Mhc) and cardiac Troponin I and slow skeletal Troponin I, developmental transitions have been observed in differentiated ES cell cultures. Expression of Mlc2v and Anf is often used to demarcate ventricular-like and atrial-like cells in ES cell cultures, respectively, although in ESDCs, Anf expression does not exclusively identify atrial cardiomyocytes and may be a general marker of the working myocardial cells.

Isolation and Identification of a Substantially Pure Population of Human Primordial Isl1+ Progenitors One aspect of the present invention relates to the isolation of a substantially pure population of human ISL1++ primordial cardiovascular progenitors as disclosed herein Methods to determine the expression, for example the expression of RNA or protein expression of markers of human ISL1+ primordial cardiovascular progenitors, such as expression of Isl-1, but not Nkx2.5 or KDR expression are well known in the art, and are encompassed for use in this invention. Such methods of measuring gene expression are well known in the art, and are commonly performed on using DNA or RNA collected from a biological sample of the cells, and can be performed by a variety of techniques known in the art, including but not limited to, PCR, RT-PCR, quantitative RT-PCR (qRT-PCR), hybridization with probes, northern blot analysis, in situ hybridization, microarray analysis, RNA protection assay, SAGE or MPSS. In some embodiments, the probes used detect the nucleic acid expression of the marker genes can be nucleic acids (such as DNA or RNA) or nucleic acid analogues, for example peptide-nucleic acid (PNA), pseudocomplementary PNA (pcPNA), locked nucleic acid (LNA) or analogues or variants thereof.

In other embodiments, the expression of the markers can be detected at the level of protein expression. The detection of the presence of nucleotide gene expression of the markers, or detection of protein expression can be similarity analyzed using well known techniques in the art, for example but not limited to immunoblotting analysis, western blot analysis, immunohistochemical analysis, ELISA, and mass spectrometry. Determining the activity of the markers, and hence the presence of the markers can be also be done, typically by in vitro assays known by a person skilled in the art, for example Northern blot, RNA protection assay, microarray assay etc and activation of signaling pathways of isl1 etc. In particular embodiments, qRT-PCR can be conducted as ordinary qRT-PCR or as multiplex qRT-PCR assay where the assay enables the detection of multiple markers simultaneously, for example for the positive expression of isl-1 and negative expression of Nkx2.5 and/or KDR, either together or separately from the same reaction sample, as shown in the Examples and in FIGS. 3A, 3D, and 4B.

One variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., Genome Research 6:986-994 (1996). Methods of real-time quantitative PCR using TaqMan probes are well known in the art. Detailed protocols for real-time quantitative PCR are provided, for example, for RNA in: Gibson et al., 1996, A novel method for real time quantitative RT-PCR. Genome Res., 10:995-1001; and for DNA in: Heid et al., 1996, Real time quantitative PCR. Genome Res., 10:986-994. TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data. 5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct). To minimize errors and the effect of sample-to-sample variation, RT-PCR is usually performed using an internal standard. The ideal internal standard is expressed at a relatively constant level among different tissues, and is unaffected by the experimental treatment. RNAs frequently used to normalize patterns of gene expression are mRNAs for the housekeeping genes glyceraldehyde-3-phosphate-dehydrogenase (GAPDH) and β-actin.

In some embodiments, the systems for real-time PCR uses, for example, Applied Biosystems (Foster City, Calif.) 7700 Prism instrument. Matching primers and fluorescent probes can be designed for genes of interest using, for example, the primer express program provided by Perkin Elmer/Applied Biosystems (Foster City, Calif.). Optimal concentrations of primers and probes can be initially determined by those of ordinary skill in the art, and control (for example, beta-actin) primers and probes may be obtained commercially from, for example, Perkin Elmer/Applied Biosystems (Foster City, Calif.). To quantitate the amount of the specific nucleic acid of interest in a sample, a standard curve is generated using a control. Standard curves may be generated using the Ct values determined in the real-time PCR, which are related to the initial concentration of the nucleic acid of interest used in the assay. Standard dilutions ranging from $10\text{-}10^6$ copies of the sequence of interest are generally sufficient. In addition, a standard curve is generated for the control sequence. This permits standardization of initial content of the nucleic acid of interest in a tissue sample to the amount of control for comparison purposes.

Other methods for detecting the expression of the marker gene are well known in the art and disclosed in patent application WO2000/04194, incorporated herein by reference. In an exemplary method, the method comprises amplifying a segment of DNA or RNA (generally after converting the RNA to cDNA) spanning one or more known isoforms of the markers (such as Isl-1, Nkx2.5, flk1) gene sequences. This amplified segment is then subjected to a detection method, such as signal detection, for example fluorescence, enzymatic etc. and/or polyacrylamide gel electrophoresis. The analysis of the PCR products by quantitative mean of the test biological sample to a control sample indicates the presence or absence of the marker gene in the cardiovascular stem cell sample. This analysis may also be performed by established methods such as quantitative RT-PCR (qRT-PCR).

The methods of RNA isolation, RNA reverse transcription (RT) to cDNA (copy DNA) and cDNA or nucleic acid amplification and analysis are routine for one skilled in the art and examples of protocols can be found, for example, in the Molecular Cloning: A Laboratory Manual (3-Volume Set) Ed. Joseph Sambrook, David W. Russel, and Joe Sambrook, Cold Spring Harbor Laboratory; 3rd edition (Jan. 15, 2001), ISBN: 0879695773. Particularly useful protocol source for methods used in PCR amplification is PCR (Basics: From Background to Bench) by M. J. McPherson, S. G. Willer, R. Beynon, C. Howe, Springer Verlag; 1st edition (Oct. 15, 2000), ISBN: 0387916008. Other methods for detecting expression of the marker genes by analyzing RNA expression comprise methods, for example but not limited to, Northern blot, RNA protection assay, hybridization methodology and microarray assay etc. Such methods are well known in the art and are encompassed for use in this invention.

Primers specific for PCR application can be designed to recognize nucleic acid sequence encoding isl1, Nkx2.5 and flk1, are well known in the art. For purposes of a non-limiting example, the nucleic acid sequence encoding human Nkx2.5 can be identified by accession number: AB021133. For purposes of an example only, the nucleic acid sequence encoding human Isl1 can be identified by accession number: BC031213. For purposes of an example, the nucleic acid sequence encoding human flk1 can be identified by accession no AF035121 or murine flk1 can be identified by accession number: NM_010612. Flk1 is also known by synonyms; KDR, Flk-1, Flk1, vascular endothelial growth factor receptor-2, VEGF receptor-2, VEGFR-2, VEGFR2.

Any suitable immunoassay format known in the art and as described herein can be used to detect the presence of and/or quantify the amount of marker in the human ISL1+ primordial cardiovascular progenitors, for example for the positive expression of Isl-1, and negative expression of Nkx2.5 and KDR markers expressed by the cardiovascular stem cell. The invention provides a method of screening for the markers expressed by the cardiovascular stem cells by immunohistochemical or immunocytochemical methods, typically termed immunohistochemistry ("IHC") and immunocytochemistry ("ICC") techniques. IHC is the application of immunochemistry on samples of tissue, whereas ICC is the application of immunochemistry to cells or tissue imprints after they have undergone specific cytological preparations such as, for example, liquid-based preparations Immunochemistry is a family of techniques based on the use of a specific antibody, wherein antibodies are used to specifically recognize and bind to target molecules on the inside or on the surface of the human ISL1+ primordial cardiovascular progenitors, for example to detect the presence of Isl-1, and negative expression of Nkx2.5 and/or KDR. In some embodiments, the antibody contains a reporter or marker that will catalyze a biochemical reaction, and thereby bring about a change color, upon encountering the targeted molecules. In some instances, signal amplification may be integrated into the particular protocol, wherein a secondary antibody, that includes the marker stain, follows the application of a primary specific antibody. In such embodiments, the marker is an enzyme, and a color change occurs in the presence and after catalysis of a substrate for that enzyme.

Immunohistochemical assays are known to those of skill in the art (e.g., see Jalkanen, et al., J. Cell. Biol. 101:976-985 (1985); Jalkanen, et al., J. Cell. Biol. 105:3087-3096 (1987). Antibodies, polyclonal or monoclonal, can be purchased from a variety of commercial suppliers, or may be manufactured using well-known methods, e.g., as described in Harlow et al., Antibodies: A Laboratory Manual, 2nd Ed; Cold. Spring Harbor Laboratory Press, Cold Spring Harbor, N.Y. (1988). In general, examples of antibodies useful in the present invention include anti-Isetl, anti-Nkx2.5, anti-KDR antibodies. Such antibodies can be purchased, for example, from Developmental Hybridoma Bank; BD PharMingen; Biomedical Technologies; Sigma; RDI; Roche and other commercially available sources. Alternatively, antibodies (monoclonal and polyclonal) can easily produced by methods known to person skilled in the art. In alternative embodiments, the antibody can be an antibody fragment, an analogue or variant of an antibody.

In some embodiments, any antibodies that recognize Isl-1, Nkx2.5 and Flk1 can be used by any persons skilled in the art, and from any commercial source. Examples of such antibodies include but are not limited to: anti-Isl1 (mouse monoclonal antibody, clone 39.4D5, Developmental Hybridoma bank); anti-Isl1 from Sigma, anti-Isl1 from Abcam; anti-KDR a rat monoclonal, clone Avas 12a1, BD Pharmingen; anti-flk1 from AbCam; anti-Nkx2.5, a goat polyclonal from R&D systems; and anti-Nkx2.5 from Santa Cruz Biotechnology, Inc.

In some embodiments, for detection of the markers by immunohistochemistry, the human ISL1+ primordial cardiovascular progenitors may be fixed by a suitable fixing agent such as alcohol, acetone, and paraformaldehyde prior to, during or after being reacted with (or probed) with an antibody. In some embodiments, immunohistochemistry on the human ISL1+ primordial cardiovascular progenitors can be performed on non-fixed cells. Conventional methods for immunohistochemistry are described in Harlow and Lane (Eds) (1988) In "Antibodies A Laboratory Manual", Cold Spring Harbor Press, Cold Spring Harbor, N.Y.; Ausbel et al (Eds) (1987), in Current Protocols In Molecular Biology, John Wiley and Sons (New York, N.Y.). For direct labeling techniques, a labeled antibody is utilized. For indirect labeling techniques, the sample is further reacted with a labeled substance. Alternatively, immunocytochemistry may be utilized. In general, cells are obtained from a patient and fixed by a suitable fixing agent such as alcohol, acetone, and paraformaldehyde, prior to, during or after being reacted with (or probed) with an antibody. Methods of immunocytological staining of biological samples, including human samples, are known to those of skill in the art and described, for example, in Brauer et al., 2001 (FASEB J, 15, 2689-2701), Smith Swintosky et al., 1997 Immunological methods of the present invention are advantageous because they require only small quantities of biological material, such as a small quantity of cardiovascular stem cells. Such methods may be done at the cellular level and thereby necessitate a minimum of one cell.

In some embodiments, cells can be permeabilized to stain cytoplasmic molecules. In general, antibodies that specifically bind a differentially expressed polypeptide are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.) The absence or presence of antibody binding can be determined by various methods, including flow cytometry of dissociated cells, microscopy, radiography, scintillation counting, etc. Any suitable alternative methods can of qualitative or quantitative detection of levels or amounts of differentially expressed polypeptide can be used, for example ELISA, western blot, immunoprecipitation, radioimmunoassay, etc.

In a different embodiment, antibodies (a term that encompasses all antigen-binding antibody derivatives and antigen-binding antibody fragments) that recognize the markers Isl1, Nkx2.5 and flk1 are used to detect cells that express the markers. The antibodies bind at least one epitope on one or more of the markers and can be used in analytical techniques, such as by protein dot blots, sodium dodecyl sulfate polyacrylamide gel electrophoresis (SDS-PAGE), or any other gel system that separates proteins, with subsequent visualization of the marker (such as Western blots). Antibodies can also be used, for example, in gel filtration or affinity column purification, or as specific reagents in techniques such as fluorescent-activated cell sorting (FACS). Other assays for cells expressing a specific marker can include, for example, staining with dyes that have a specific reaction with a marker molecule (such as ruthenium red and extracellular matrix molecules), identification specific morphological characteristics (such as the presence of microvilli in epithelia, or the pseudopodialfilopodia in migrating cells, such as fibroblasts and mesenchyme). Biochemical assays include, for example, assaying for an enzymatic product or intermediate, or for the overall composition of a cell, such as the ratio of protein to lipid, or lipid to sugar, or even the ratio of two specific lipids to each other, or polysaccharides. If such a marker is a morphological and/or functional trait or characteristic, suitable methods including visual inspection using, for example, the unaided eye, a stereomicroscope, a dissecting microscope, a confocal microscope, or an electron microscope are encompassed for use in the invention. The invention also contemplates methods of analyzing the progressive or terminal differentiation of a cell employing a single marker, as well as any combination of molecular and/or non-molecular markers.

Various methods can be utilized for quantifying the presence of the selected markers and or reporter gene. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) Trends Biotechnol. 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) Biotechniques 26(1):112-225; Kawamoto et al. (1999) Genome Res 9(12):1305-12; and Chen et al. (1998) Genomics 51(3):313-24, for examples.

Also encompassed for use in this invention, is the isolation of human ISL1+ primordial cardiovascular progenitors of the invention by the use of an introduced reporter gene that aids with the identification and isolation of human ISL1+ primordial cardiovascular progenitors. For example, a ES cell can be genetically engineered to express a construct comprising a reporter gene which can be used for selection and identification purposes. For example, a human ES cell or human ES cell line can be genetically engineered to comprise a reporter gene, for example but not limited to a fluorescent protein, enzyme or resistance gene, which is operatively linked to a particular promoter (for example, but not limited to the Isl1 promoter). In such an embodiment, when the human ES cell expresses the gene to which the reporter of interest is operatively linked, it also expresses the reporter gene, for example the enzyme, fluorescent protein, (e.g. Red fluorescent protein (RFP) or yellow fluorescent protein (YFP)) or resistance gene. ES cells that express the reporter gene can be readily identified as human ISL1+ primordial cardiovascular progenitors and in some embodiments can be positively selected for such human cells comprising the reporter gene or the gene product of the reporter gene. Other reporter genes that can be used include fluorescent proteins, luciferase, alkaline phosphatase, lacZ, or CAT.

In some embodiments, where the reporter gene is a resistance gene, the resistance gene can be, for example but not limited to, genes for resistance to amplicillin, chloroamphenicol, tetracycline, puromycin, G418, blasticidin and variants and fragments thereof. In other embodiments, the reporter gene can be a fluorescent protein, for example but not limited to: green fluorescent protein (GFP); green fluorescent-like protein (GFP-like); yellow fluorescent protein (YFP); blue fluorescent protein (BFP); enhanced green fluorescent protein (EGFP); enhanced blue fluorescent protein (EBFP); cyan fluorescent protein (CFP); enhanced cyan fluorescent protein (ECFP); red fluorescent protein (dsRED); and modifications and fluorescent fragments thereof.

This invention also encompasses the generation of useful clonal reporter cell lines of human ISL1+ primordial cardiovascular progenitors that could comprise multiple reporters to help identify human ISL1+ primordial cardiovascular progenitors that have differentiated along particular and/or multiple lineages, as disclosed in the Examples. Human ISL1+ primordial cardiovascular progenitors expressing these reporters could be easily purified by FACS, antibody affinity capture, magnetic separation, or a combination thereof. The purified or substantially pure reporter-expressing cells can be used for genomic analysis by techniques such as microarray hybridization, SAGE, MPSS, or proteomic analysis to identify more markers that characterize the cardiovascular stem cell and/or cardiovascular progenitor population of interest. These methods can be used to identify cells in an undifferentiated human ISL1+ primordial cardiovascular progenitor state, for instance cells that have not differentiated along the desired lineages, as well as populations of cells that have differentiated along the desired lineages. In some embodiments, there are many cells that have not differentiated along the desired lineages; the desired cells may be isolated and subcultured to generate a substantially purified population of the desired cardiovascular stem cell.

In some embodiments, methods to remove unwanted cells (e.g. cells which are not human ISL1+ primordial cardiovascular progenitors) are encompassed, by removing unwanted cells by negative selection. For example, unwanted antibody-labeled cells are removed by methods known in the art, such as labeling a cell population with an antibody or a cocktail of antibodies, to a cell surface protein and separation by FACS or magnetic colloids. In some embodiments, cells which express NKx2.5 and/or KDR+ can be selected and discarded as being human non-ISL1+ primordial cardiovascular progenitors. In an alternative embodiment, the reporter gene may be used to negatively select non-desired cells, for example a reporter gene encodes a cytotoxic protein in cells that are not desired. In such an embodiment, the reporter gene is operatively linked to a regulatory sequence of a gene normally expressed in the cells with undesirable phenotype.

One embodiment of the invention is a composition of human ISL1+ primordial cardiovascular progenitors as disclosed herein which are positive for expression of ISL1+, but negative for Nkx2.5 and KDR expression. In some embodiments, the human ISL1+ primordial cardiovascular progenitors are of human origin. In other embodiments, the human ISL1+ primordial cardiovascular progenitors are genetically engineered human ISL1+ primordial cardiovascular progenitors. In some embodiments, the composition is substantially pure for human ISL1+ primordial cardiovascular progenitors.

Sources of Human Stem Cells for Differentiating into Human Primordial ISL1 Progenitors The human ISL1+ primordial progenitors as disclosed herein, can be derived from any pluripotent stem cell source, for example, ES cells, as well as embryonic tissue such as fetal or pre-fetal tissue, or adult tissue), and any pluripotent stem cell that is capable under appropriate conditions of producing progeny of different cell types that are derivatives of all of the 3 germinal layers (endoderm, mesoderm, and ectoderm).

In some embodiments, a human ISL1+ progenitor as disclosed herein is isolated from an established cell line, or they may be obtained directly from primary embryonic tissue and used immediately for differentiation. In some embodiments, human ISL1+ progenitors are obtained from NIH Human Embryonic Stem Cell Registry, e.g. hESBGN-01, hESBGN-$O_2$, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, 1114 (Wisconsin Alumni Research Foundation (WiCell Research Institute)).

In some embodiments, human ISL1+ primordial progenitors as disclosed herein are derived from iPS cells or partially induced pluripotent stem cells. In some embodiments, human ISL1+ primordial progenitors are derived from a population of pluripotent stem cells, including adult stem cells, embryonic stem cells, embryonic stem cell lines and the like. Alternatively, one can use cells for cell transplants derived from any number of cells sources known to a person of ordinary skill in the art, such as for example, but not limited to, stem cells, such as cardiac progenitor cells, or embryonic sources, embryonic stem (ES) cells, adult stem cells (ASC), embryoid bodies (EB) and iPS cells.

In some embodiments, where human ISL1+ primordial progenitors are isolated from embryonic sources, ES cells or EBs, the embryo is not destroyed. Accordingly, in one embodiment, human ISL1+ primordial progenitors are isolated from ES cells where a human embryo is not destroyed.

In another embodiment, the human ISL1+ primordial progenitors can be isolated from embryonic cells of various types, exemplified by human embryonic stem (hES) cells, described by Thomson et al. (1998) Science 282:1145; embryonic stem cells from other primates, such as Rhesus stem cells (Thomson et al. (1995) Proc. Natl. Acad. Sci. USA 92:7844); marmoset stem cells (Thomson et al. (1996) Biol. Reprod. 55:254); and human embryonic germ (hEG) cells (Shambloft et al., Proc. Natl. Acad. Sci. USA 95:13726, 1998). Also of interest are lineage committed stem cells, such as mesodermal stem cells and other early cardiogenic cells (see Reyes et al. (2001) Blood 98:2615-2625; Eisenberg & Bader (1996) Circ Res. 78(2):205-16; etc.) The stem cells may be obtained from any mammalian species, e.g. human, equine, bovine, porcine, canine, feline, rodent, e.g. mice, rats, hamster, primate, etc.

ES cells are considered to be undifferentiated when they have not committed to a specific differentiation lineage. Such cells display morphological characteristics that distinguish them from differentiated cells of embryo or adult origin. Undifferentiated ES cells are easily recognized by those skilled in the art, and typically appear in the two dimensions of a microscopic view in colonies of cells with high nuclear/cytoplasmic ratios and prominent nucleoli. Undifferentiated ES cells express genes that may be used as markers to detect the presence of undifferentiated cells, and whose polypeptide products may be used as markers for negative selection. For example, see U.S. application Ser. No. 2003/0224411 A1; Bhattacharya (2004) Blood 103(8):2956-64; and Thomson (1998), supra., each herein incorporated by reference. Human ES cell lines express cell surface markers that characterize undifferentiated nonhuman primate ES and human EC cells, including stage-specific embryonic antigen (SSEA)-3, SSEA-4, TRA-1-60, TRA-1-81, and alkaline phosphatase. The globo-series glycolipid GL7, which carries the SSEA-4 epitope, is formed by the addition of sialic acid to the globo-series glycolipid Gb5, which carries the SSEA-3 epitope. Thus, GL7 reacts with antibodies to both SSEA-3 and SSEA-4. The undifferentiated human ES cell lines did not stain for SSEA-1, but differentiated cells stained strongly for SSEA-I. Methods for proliferating hES cells in the undifferentiated form are described in WO 99/20741, WO 01/51616, and WO 03/020920, which are incorporated herein in their entirety by reference.

In some embodiments, Isl1+ primordial progenitors are derived from human embryonic stem cells as the starting material. Such pluripotent cells can be cells that originate from the morula, embryonic inner cell mass or those obtained from embryonic gonadal ridges. Human embryonic stem cells can be maintained in culture in a pluripotent state without substantial differentiation using methods that are known in the art. Such methods are described, for example, in U.S. Pat. Nos. 5,453,357, 5,670,372, 5,690,926 5,843,780, 6,200,806 and 6,251,671 the disclosures of which are incorporated herein in their entireties by reference.

In some processes, hESCs are maintained on a feeder layer. In such processes, any feeder layer which allows hESCs to be maintained in a pluripotent state can be used. One commonly used feeder layer for the cultivation of human embryonic stem cells is a layer of mouse fibroblasts. More recently, human fibroblast feeder layers have been developed for use in the cultivation of hESCs (see US Patent Application No. 2002/0072117, the disclosure of which is incorporated herein by reference in its entirety). Alternative processes permit the maintenance of pluripotent hESC without the use of a feeder layer. Methods of maintaining pluripotent hESCs under feeder-free conditions have been described in US Patent Application No. 2003/0175956, the disclosure of which is incorporated herein by reference in its entirety.

The human embryonic stem cells used herein can be maintained in culture either with or without serum. In some embryonic stem cell maintenance procedures, serum replacement is used. In others, serum free culture techniques, such as those described in US Patent Application No. 2003/0190748, the disclosure of which is incorporated herein by reference in its entirety, are used.

Stem cells are maintained in culture in a pluripotent state by routine passage until it is desired that they be differentiated into definitive endoderm then ultimately to endocrine precursor cells and/or pancreatic islet hormone-expressing cells.

In some embodiments, the human ISL1+ primordial progenitors can derived from reprogrammed cells, e.g., induced pluripotent stem cells (iPS cells) derived from differentiated or somatic cells. In such an embodiment, the iPS cells can be derived from, for example, but not limited to, neoplastic cells, tumor cells and cancer cells. Such an embodiment is useful in identifying and/or isolating and/or studying cancerous cells and tumor cells. In some embodiments, the de-differentiated cells are from a subject, and in some embodiments, the de-differentiated stem cells are obtained from a biopsy.

In some embodiments, an iPS cell used for generation of ISL1+ primordial progenitor can be produced by any method known in the art can be used, for example virally-induced or chemically induced generation of iPS cells are described in Mauritz et al., Circulation. 2008; 118:507-517, and disclosed in International Application WO2008/088882, EP1970446, US2009/0047263, US2009/0068742, and 2009/0227032, which are incorporated herein in their entirety by reference.

iPS cells can also be generated using other methods commonly known in the art, such as, including but not limited to uses of non-viral methods, polycistronic vectors, mRNA species, miRNA, and proteins, including International Patent Applications WO2010/019569, WO2009/149233, WO2009/093022, WO2010/022194, WO2009/101084, WO2008/038148, WO2010/059806, WO2010/057614, WO2010/056831, WO2010/050626, WO2010/033906, WO2009/126250, WO2009/143421, WO2009/140655, WO2009/133971, WO2009/101407, WO2009/091659, WO2009/086425, WO2009/079007, WO2009/058413, WO2009/032456, WO2009/032194, WO2008/103462, JP4411362, EP2128245, and U.S. Patent Applications US2004/0072343, US2009/0253203, US2010/0112693, US2010/07542, US2009/0246875, US2009/0203141, US2010/00625343, US2009/0269763, which are incorporated herein in their entirety by reference.

In another embodiment, the human ISL1+ primordial progenitors can be isolated from tissue including solid tissues (the exception to solid tissue is whole blood, including blood, plasma and bone marrow) which were previously unidentified in the literature as sources of stem cells. In some embodiments, the tissue is heart or cardiac tissue. In other embodiments, the tissue is for example but not limited to, umbilical cord blood, placenta, bone marrow, or chondral villi.

A mixture of cells from a suitable source of endothelial, muscle, and/or neural stem cells, as described above, is harvested from a mammalian donor by methods known in the art. A suitable source is the hematopoietic microenvironment. For example, circulating peripheral blood, preferably mobilized (i.e., recruited) as described below, may be removed from a subject. Alternatively, bone marrow may be obtained from a mammal, such as a human patient, undergoing an autologous transplant In another embodiment, the human ISL1+ primordial progenitors can be isolated from human umbilical cord blood cells (HUCBC) have recently been recognized as a rich source of hematopoietic and mesenchymal progenitor cells (Broxmeyer et al., 1992 Proc. Natl. Acad. Sci. USA 89:4109-4113). Previously, umbilical cord and placental blood were considered a waste product normally discarded at the birth of an infant. Cord blood cells are used as a source of transplantable stem and progenitor cells and as a source of marrow repopulating cells for the treatment of malignant diseases (i.e. acute lymphoid leukemia, acute myeloid leukemia, chronic myeloid leukemia, myelodysplastic syndrome, and nueroblastoma) and non-malignant diseases such as Fanconi's anemia and aplastic anemia (Kohli-Kumar et al., 1993 Br. J. Haematol. 85:419-422; Wagner et al., 1992 Blood 79; 1874-1881; Lu et al., 1996 Crit. Rev. Oncol. Hematol 22:61-78; Lu et al., 1995 Cell Transplantation 4:493-503). A distinct advantage of HUCBC is the immature immunity of these cells that is very similar to fetal cells, which significantly reduces the risk for rejection by the host (Taylor & Bryson, 1985 J. Immunol. 134:1493-1497).

Human umbilical cord blood contains mesenchymal and hematopoietic progenitor cells, and endothelial cell precursors that can be expanded in tissue culture (Broxmeyer et al., 1992 Proc. Natl. Acad. Sci. USA 89:4109-4113; Kohli-Kumar et al., 1993 Br. J. Haematol. 85:419-422; Wagner et al., 1992 Blood 79; 1874-1881; Lu et al., 1996 Crit. Rev. Oncol. Hematol 22:61-78; Lu et al., 1995 Cell Transplantation 4:493-503; Taylor & Bryson, 1985 J. Immunol. 134:1493-1497 Broxmeyer, 1995 Transfusion 35:694-702; Chen et al., 2001 Stroke 32:2682-2688; Nieda et al., 1997

Br. J. Haematology 98:775-777; Erices et al., 2000 Br. J. Haematology 109:235-242). The total content of hematopoietic progenitor cells in umbilical cord blood equals or exceeds bone marrow, and in addition, the highly proliferative hematopoietic cells are eightfold higher in HUCBC than in bone marrow and express hematopoietic markers such as CD14, CD34, and CD45 (Sanchez-Ramos et al., 2001 Exp. Neur. 171:109-115; Bicknese et al., 2002 Cell Transplantation 11:261-264; Lu et al., 1993 J. Exp Med. 178:2089-2096).

In another embodiment, the human ISL1+ primordial progenitors can be isolated from a source of cells is the hematopoietic micro-environment, such as the circulating peripheral blood, preferably from the mononuclear fraction of peripheral blood, umbilical cord blood, bone marrow, fetal liver, or yolk sac of a mammal. The stem cells, especially neural stem cells, may also be derived from the central nervous system, including the meninges.

In another embodiment, the human ISL1+ primordial progenitors can be isolated from a human pluripotent stem cell source, and can proliferated prior to its use for generation of a vascularized human cardiac tissue. Methods for proliferation of human primordial ISL1+ cells include a co-culture with a mesenchymal cell, or cardiac messenchymal feeder layer, where the mesenchymal cells provide an environment permissive for maintenance of stem cells in an undifferentiated state in which stem cells can proliferate. Methods to proliferate the ISL1+ cells are disclosed in International Patent Applications WO 2008/054819 and WO 2008/098184 which are incorporated herein in their entirety by reference.

The inventors demonstrate that the human ISL1+ primordial progenitors can be also be induced to differentiate and/or mature along different lineages (e.g. cardiomyocyte lineages, endothelial lineages and smooth muscle lineages) spontaneously in the co-culture of a cardiac messanchymal feeder layer, or alternatively by addition of factors to induce differentiation, by such methods that are commonly known in the art. Such conditions may also be referred to as differentiate conditions. For instance, any growth factors or differentiation-inducing factors can be added to the medium, as well as a supporting structure (such as a substrate on a solid surface) to induce differentiation. Differentiation may be initiated by allowing the stem cells to form aggregates, or similar structures, for example, aggregates can result from overgrowth of a stem cell culture, or by culturing the stem cells in culture vessels having a substrate with low adhesion properties.

In one embodiment of the invention, embryoid bodies are formed by harvesting ES cells with brief protease digestion, and allowing small clumps of undifferentiated human ESCs to grow in suspension culture. Differentiation is induced by withdrawal of conditioned medium. The resulting embryoid bodies are plated onto semi-solid substrates. Formation of differentiated cells may be observed after around about 7 days to around about 4 weeks. Viable differentiating cells from in vitro cultures of stem cells are selected for by partially dissociating embryoid bodies or similar structures to provide cell aggregates. Aggregates comprising cells of interest are selected for phenotypic features using methods that substantially maintain the cell to cell contacts in the aggregate.

Three-Dimensional Human Vascularized Cardiac Tissue.

One aspect of the present invention relates to the use of human primordial ISL1+ progenitors to generate functional three-dimensional vascularized human cardiac tissue in vivo. In one embodiment, the human primordial ISL1+ progenitors are implanted into a subject, where they spontaneously differentiate into human smooth muscle progenitors, epithelial progenitors and cardiomyocyte progenitors, which further differentiate into smooth muscle tissue, vascular tissue and cardiac muscle respectively. In some embodiments, a population of human primordial ISL1+ progenitors can be implanted into a subject, and proportion of human primordial ISL1+ progenitor cells within the population will differentiate along cardiomyocyte lineages, a proportion of human primordial ISL1+ progenitor cells will differentiate along endothelial lineages and a proportion of human primordial ISL1+ progenitor cells will differentiate along smooth muscle lineages. Accordingly, one aspect of the present invention relates to the use of human primordial ISL1+ progenitors to generate a functional three-dimensional vascularized cardiac tissue in vivo, with out the need of scaffolds or matrices or other manipulations (e.g. addition of growth factors or angiogenic agents or other agents) for production of human vascularized cardiac tissue.

In some embodiments, a population of human primordial ISL1+ progenitor cells are primed to increase the efficiency to differentiate along endothelial lineages by culturing in the presence of VEGF and/or an inhibitor of the TGFβ signaling pathway, such as an ALK5 inhibitor (ALK5i) or the like. In some embodiments, the primordial ISL1+ progenitor cells are differentiated into isl1+/CD31+ cell by culturing the primordial ISL1+ progenitor cells in a media comprising VEGF or an analogue or functional homologue thereof, and/or an inhibitor of the TGFβ signaling pathway, such as an ALK5 inhibitor (ALK5i) or the like.

In some embodiments, a population of human ISL1+ primordial progenitors implanted into a subject can undergo coordinated differentiation into cardiomyocytes, endothelial cells and smooth muscle cells, such that they form, in vivo, a functional cardiac tissue which is vascularized. In some embodiments, the population of human ISL1+ primordial progenitors has been contacted with VEGF and/or an inhibitor of the TGFβ signaling pathway, such as an ALK5 inhibitor (ALK5i) prior to implantation, and in some embodiments, the human ISL1+ primordial progenitors are implanted into the subject in the presence of VEGF and/or an inhibitor of the TGFβ signaling pathway, such as an ALK5 inhibitor (ALK5i), e.g., for example as an admixture of cells and human ISL1+ primordial progenitors. In some embodiments, the human ISL1+ primordial progenitors are present on a three-dimensional matrix or scaffold as disclosed herein. In some embodiments, the three dimensional scaffold comprising the ISL1+ primordial progenitors also comprises VEGF and/or an inhibitor of the TGFβ signaling pathway, such as an ALK5 inhibitor (ALK5i).

In some embodiments, when a population of human primordial ISL1+ progenitors is implanted into a subject, some primordial ISL1+ progenitors will self-replicate (e.g. proliferate or renew), and some will differentiate along cardiomyocyte lineages to produce a cardiomyocyte progenitor, or differentiate along an endothelial lineage to produce an endothelial progenitor, or differentiate along a smooth muscle lineage to produce a smooth muscle progenitor. In such instances, these human cardiomyocyte progenitors, human endothelial progenitors and human smooth muscle progenitors can self-replicate (e.g. proliferate) before terminally differentiating into cardiomyocytes, endothelial cells and smooth muscle cells respectively.

In some embodiments, the human ISL1+ progenitors are implanted into a subject, for example a human, for example for therapeutic purposes, or an animal subject. In some embodiment, human ISL1+ progenitors can be implanted into any suitable location in a subject, for example but not limited to, a kidney such as a kidney capsule, heart, ascites, peritoneal cavity, pericardium, epicardium, on the surface of the heart, in a pericardial space, and the like.

In some embodiments, a population of human ISL1+ progenitors are encapsulated in a bioreactor bag, which can be implanted into a subject at a suitable location, for example on the surface of the heart, subcutaneously or the like. Examples of a bioreactor include, for example, a sleeved organized ISL1+ primordial progenitors, wherein the sleeve comprises a biocompatible structure encircling a length of the tissue, or circumferentially surrounding or enclosing the tissue. As used herein, "a length of the tissue" refers to at least 50% of the total length of the tissue, or at least 80%, 90% or even greater than the length of the tissue. Where multiple organized tissues are contained within a sleeve, the sleeve will encompass "a length" of at least one such organized tissue, and possibly also of two, three, four or more plural organized tissues. The sleeved organized tissue according to the invention also includes a sleeved tissue wherein the tissue is substantially encapsulated or surrounded (i.e., encircled along a length, where the length of encirclement is at least 50% of the length of the tissue, or 80%, 90%, or fully encapsulated) by the sleeve. Examples of bioreactors are disclosed in U.S. Patent Applications 2005/0260178; 2004/0043010, 2003/0235561 and 2003/0180264 which are incorporated herein in their entirety by reference.

Figure 5:
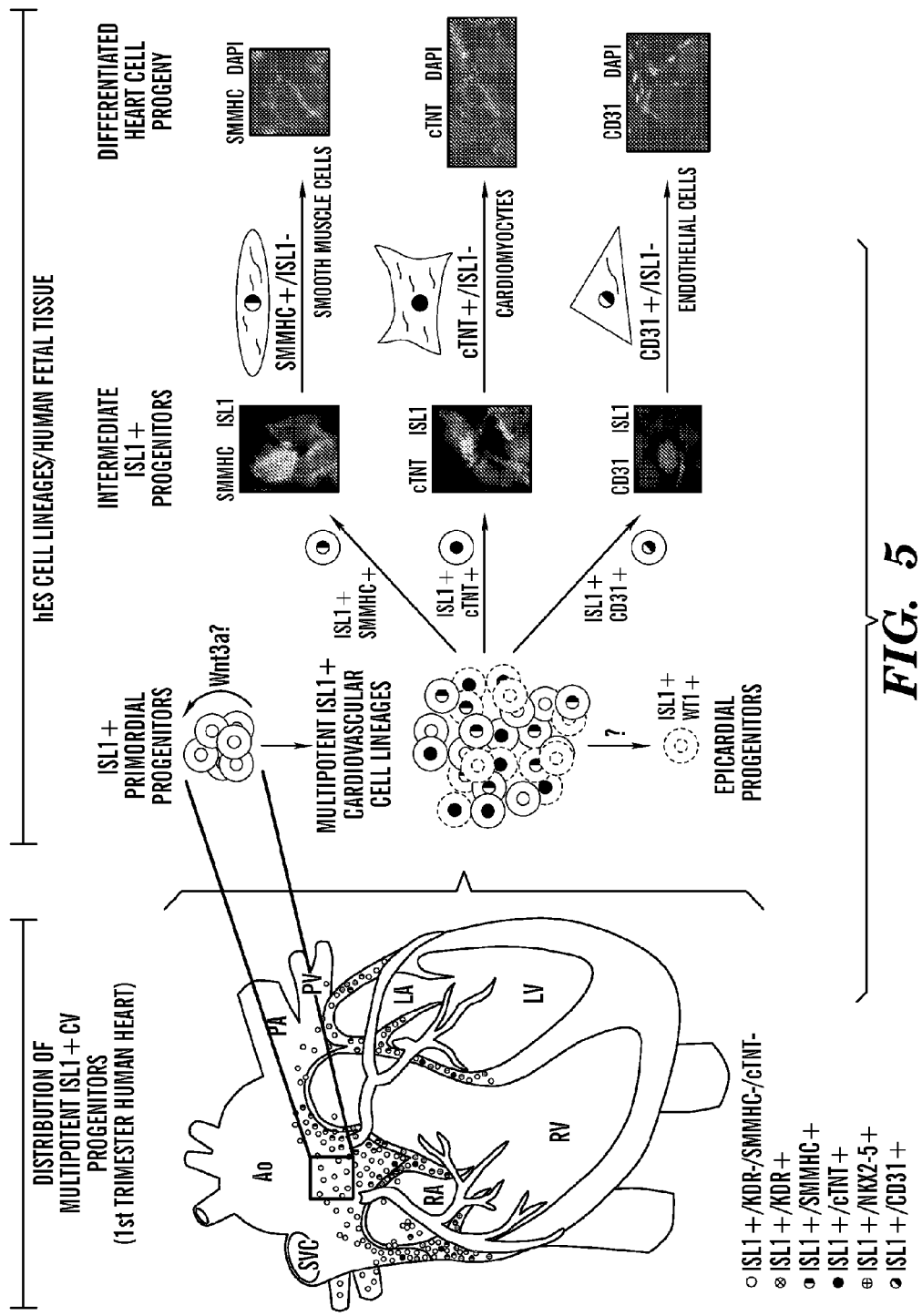
FIG. 5 shows a working model proposing a primordial ISL1+ progenitor generating a family of human multipotent cardiovascular lineages.

As the human ISL1+ primordial progenitors (Isl1+/Nkx2.5−/KDR−) can differentiate into multipotent Isl1+ cardiovascular progenitor (MICP) cell lineages, which are Isl1+/Nkx2.5+/KDR+ pluripotent cardiac cells as disclosed in WO2008/054819 and are precursor cells of virtually all the different tissue types in the heart (see FIG. 5 of Martin-Puing et al, Cell Stem Cell, 2008, 2, 320-330 "Lives of a Heart Cell: Tracting the origins of Cardiac Progenitors", which is incorporated herein by reference), the ISL1+ primordial cells can be differentiated into multipotent Isl1+ cardiovascular cell lineages and can then subsequently differentiate into any cell type of the heart, including but not limited to, epicardial cells, endothelial cells, cardiomyocytes and smooth muscle cells, including pace maker cells, purkinji cells, and cells which make up the vascular coronary tree, the population of ISL1+ primordial cells implanted into a subject can form functional human vascularized tissue.

In some embodiments, the functional 3D human vascularized human tissue has substantially the same properties of normal functional endogenous human myocardium, including but not limited to, substantially the same contracting force, contraction frequency, contraction stamina, and vascularization as endogenous human myocardium.

In some embodiments, the human ISL1+ primordial progenitors can be implanted into a subject in the absence of a matrix or scaffold. In some embodiments, the human ISL1+ primordial progenitors can be implanted into a subject in the presence of a three-dimensional matrix or scaffold, as defined herein. In some embodiments, the scaffold can be a patterned polymer scaffold as disclosed in International daPatent Application PCT/US2009/060224 or WO2008/045506, which are incorporated herein in their entirety by reference. Alternatively, one of ordinary skill in the art can use any scaffold, for example biocompatible or bioresorbable scaffolds, including those disclosed in US Patent Applications: 2008/019229 and International Application WO/2003/050266, which are incorporated herein in their entirety by reference.

In some embodiments, the human ISL1+ primordial progenitors can be implanted into a subject in the absence of growth factors. Alternatively, in some embodiments, the human ISL1+ primordial progenitors can be implanted into a subject in the presence of at least one or a combination of growth factors, such as cardiotrophic factors as disclosed herein, or at least one or a combination of angiogenic factors.

Differentiation of Human ISL1+ Primordial Progenitors Along Vasculargenic Lineages As disclosed herein, the inventors have discovered that human Isl1+ primordial progenitors (which are Isl1$^+$/Nkx2.5$^-$/KDR$^-$) can be differentiated along vasculargenic lineages, e.g., into cardiac vascular progenitors cells that are Isl1+/CD31+, and in some embodiments, results in about a 4-5 fold greater enrichment by contacting the primordial Isl1+ cells with at least one of the following; VEGF, VEGF homologue, a inhibitor of TGF-β signalling, an ALK5-inhibitor and the like. The differentiation of the human Isl1+ primordial progenitors along vasculargenic lineages, e.g., into cardiac vascular progenitors expressing Isl1+/CD31+ are particularly useful for generating the vascular network for a properly vascularized cardiac tissue as disclosed herein. In particular, using Isl1+ primordial progenitors for differentiating into Isl1+/CD31+ cells is advantageous as it allows their differentiation to balance with the differentiation of Isl1+ primordial progenitors into other cell types, e.g., along myogenic lineages for the auto-assembly of a vascularized cardiac tissue.

Dalton et al, in WO2010/011352 allegedly reports treating an epicardial pluripotent cell (EPCs), which can be derived from an ISL1+ multipotent progenitor (IMP), with VEGF or SB431542. The IMPs discussed in the '352 application are Isl1+ and Nkx2.5+, and are different from the Isl1+ primordial progenitors of the present invention (which are $Isl1^+$/$Nkx2.5^-$/$KDR^-$). The '352 application does not discuss or disclose $Isl1^+$/$Nkx2.5^-$/$KDR^-$ primordial progenitors of the present invention (see FIG. 5 of the present application). Thus, in contrast to the present application, the '352 application does not suggest or discuss contacting human Isl1+ primordial progenitors (which are $Isl1^+$/$Nkx2.5^-$/$KDR^-$) with VEGF and/or SB431542 to induce their differentiation along vascularogenic lineages. As disclosed herein, the inventors have surprisingly demonstrated that it is advantageous to differentiate Isl1+/CD31+ directly from the Isl1+ primordial progenitors, as this is more efficient than from their downstream progenitors, and also enables coordinated myogenesis and vascularization for the auto-assembly of a vascularized cardiac tissue.

In some embodiments, the human ISL1+ primordial progenitors can be implanted into a subject in the presence of VEGF or an inhibitor of TGFβ signalling, such as ALK5-inhibitor as disclosed herein. In some embodiments, the human ISL1+ primordial progenitors can be implanted into a subject after being contacted with VEGF or an inhibitor of TGFβ signalling, where a proportion of the population of the human ISL1+ primordial progenitors cells have been differentiated into Isl1+/CD31+ vascularogenic progenitors. In some embodiments, at least about 0.2% or at least about 0.3%, or at least about 0.4%, or at least about 0.5%, or at least about 0.6%, or at least about 0.7%, or at least about 0.8%, or at least about 0.9%, or at least about 1.0%, or at least about 1.2%, or at least about 1.4%, or at least about 1.5%, or at least about 2.0% of the proportion of the human ISL1+ primordial progenitors cells have differentiated to be Isl1+/CD31+ cardiovascular progenitors.

Accordingly, in some embodiments, the human vascularized cardiac tissue or human ISL1+ primordial progenitors can be implanted into a subject in need thereof in the presence of growth factors, and/or angiogenic factors. In some embodiments, the ISL1+ primordial cells are genetically modified to express the growth factors and/or angiogenic factors as disclosed herein, under the control of constitutive, or tissue-specific or inducible promoters. Exemplary angiogenic factors include, vascularogenic factors is selected from the group consisting of: VEGF A, VEGF B, VEGF C, VEGF D, VEGF E, VEGF F, FGF 1, FGF 2, FGF 3, FGF 4, FGF-5, PDGF AA, PDGF BB, PDGF AB, angiopoeitin, MCP, EPO, IL-1, IL-2, IL-3, IL-4, IL-S, IL-6, IL-7, IL-8, IL-9, IL-10, IL-11, IL-12, IL-13, IL-14, IL-15, IL-16, IL-17, IL-18, IL-19, IL-20, IL-21, IL-22. Exemplary cytokines include angiogenin, vascular endothelial growth factor (VEGF, including, but not limited to VEGF-165), interleukins, fibroblast growth factors, for example, but not limited to, FGF-1 and FGF-2, hepatocyte growth factor, (HGF), transforming growth factor beta (TGF-β) endothelins (such as ET-1, ET-2, and ET-3), insulin-like growth factor (IGF-1), angiopoietins (such as Ang-1, Ang-2, Ang-3/4), angiopoietin-like proteins (such as ANGPTL1, ANGPTL-2, ANGPTL-3, and ANGPTL-4), platelet-derived growth factor (PDGF), including, but not limited to PDGF-AA, PDGF-BB and PDGF-AB, epidermal growth factor (EGF), endothelial cell growth factor (ECGF), including ECGS, platelet-derived endothelial cell growth factor (PD-ECGF), placenta growth factor (PLGF), and the like. The skilled artisan will understand that the choice of chemokines and cytokine fragments to be expressed by human ISL1+ primordial progenitors, or administered with the human vascularized cardiac tissue will, in part, on the target tissue or organ to be implanted with the human vascularized cardiac tissue.

VEGF

As disclosed herein, the inventors demonstrate the that contacting the cells with VEGF or an inhibitor of ALK5 increases the vasculargenic development of Isl1+ primordial progenitors and promotes vascular commitment into Isl1+/CD31+ cells by at least 2-fold. In some embodiments, contacting a population of Isl1+ primordial progenitor cells with a VEGF or a VEGF analogue such as $VEGF_{165}$ increases the efficiency of differentiation along vascularogenic lineages to Isl1+/CD31+ cells by about at least 1.5-fold, or at least about 1.7-fold, or at least about 2-fold, or at least about 3-fold, or at least about 4-fold, or at least about 5-fold, more than about 5-fold as compared to the absence of a VEGF or a VEGF analogue such as $VEGF_{165}$. In some embodiments, contacting Isl1+ primordial progenitors with VEGF or a VEGF analogue, e.g., $VEGF_{165}$ results in a higher yield of Isl1+/CD31+ cells as compared to contacting a population of the downstream multipotent Isl1+ cardiovascular progenitors (MICP). In some embodiment, the increased yield is about at least 5%, or about a 10% increased yield, or about a 15% increased yield, or about a 30% increased yield, or about a 40% increased yield, or about a 50% increased yield, or a greater than 50% yield in Isl1+/CD31+ cells derived from Isl1+ primordial progenitors as disclosed herein as compared to from Isl1+/Nkx2.5+/KDR+MICPs.

In some embodiments, a human Isl1+ primordial cell as disclosed herein is contacted with VEGF at a concentration of between 25-50 ng/ml, or about at least about 1 Ong/n1, or about at least about 15 ng/ml, or about at least about 20 ng/ml, or about at least about 25 ng/ml, or about at least about 30 ng/ml, or about at least about 35 ng/ml, or about at least about 40 ng/ml, or about at least about 45 ng/ml, or about at least about 50 ng/ml, or about at least about 55 ng/ml, or about at least about 60 ng/ml, or about at least about 65 ng/ml, or more than about at least about 65 ng/ml for increasing efficacy of differentiating Isl1+/CD31+ cells.

In some embodiments, a where the Isl1+ primordial cells as disclosed herein are from mouse, they can be contacted with VEGF at a concentration of between 2-10 ng/ml, or about at least about 1 ng/ml, or about at least about 2 ng/ml, or about at least about 3 ng/ml, or about at least about 4 ng/ml, or about at least about 5 ng/ml, or about at least about 6 ng/ml, or about at least about 1 ng/ml, or about at least about 8 ng/ml, or about at least about 9 ng/ml, or about at least about 10 ng/ml, or about at least about 11 ng/ml, or about at least about 12 ng/ml, or more than about at least about 12 ng/ml for increasing efficacy of differentiating Isl1+/CD31+ cells. In some embodiments, mouse Isl1+ primordial cells are contacted with 5 ng/ml of VEGF or a functional homologue thereof.

In some embodiments, human Isl1+ primordial progenitors are contacted with VEGF or a biological active homologue thereof for a period of at least one day, or a least 2 days, or a least about 3 days, or at least about 4 days or more, e.g., between 3-5 days, or 5-7 days, or 7-10 days, or 10-13 days or 13-16 days, beginning at any timepoint between Day 4 (D4) and Day 20 (D20) of cell age, for example, at D4, D5, D6, D7, D8, D9, D10, D11, D12, D13, D14, D15, D16, D17, D18, D19 or D20 or at a timepoint after D20.

In some embodiments, where the Isl1+ primordial progenitors are derived from mouse ES cells, the Isl1+ progenitors are contacted with VEGF or a biological active homologue thereof for a period of at least one day, or a least 2 days, or a least about 3 days, or at least about 4 days or more, e.g., between 3-5 days, or 5-7 days, or 7-10 days, beginning at any timepoint between Day 4 (D4) and Day 12 (D12) of cell age, for example, at D4, D5, D6, D7, D8, D9, D10, D11 or D12 or at a timepoint after D12.

Any VEGF or any biologically active variant or isoform thereof can be used, including known isoforms of VEGF (derived from mRNA splice site variation).

VEGF is a growth factor that acts preferentially on endothelial cells. With the current focus of biomedical research on angiogenesis, the biology of VEGF has been under intense scrutiny. In humans, there are several different genes that encode VEGF-like proteins, the most studied of these genes is that for VEGF-A. As described by several different laboratories, the VEGF-A gene gives rise to several different mature mRNA transcripts that differ in the protein products they encode. These variant transcripts arise through an alternative splicing mechanism and the abundance of any particular VEGF-A transcript differs, depending on the tissue examined. The most predominant VEGF-A transcripts found in adult tissues encode proteins of 188/189, 164/165 and 120/121 amino acids (rat/human). Other, rarer variant transcripts arising from VEGF-A have also been reported (encoding 205/206 and 144/145 amino acid proteins), but these forms were only found in a few tissues, mainly fetal in origin (VEGF 205/206: human fetal liver, sheep and human placenta/VEGF 144/145: human uterus, human endometrial carcinoma cells, sheep and human placenta, respectively). During a preliminary survey of adult penile tissues for the expression of VEGF-A isoforms, it was found that the expression of VEGF-A mRNA splice variants encoding the 205/206 and 144/145 forms of VEGF can be identified by standard RT-PCR techniques and confirmed by cloning and sequencing from other adult rat and human tissues and cultured cells. These results suggest that these rarer splice variants of VEGF-A might have a wider tissue distribution than originally anticipated.

This invention provides the above methods, wherein the vascular endothelial growth factor is VEGF-A 205/206, VEGF-A 188/189, VEGF-A 164/165, VEGF-A 144/145, VEGF-A 120/121, or VEGF-A 110.

As used herein, "VEGF-A 205/206" refers to the VEGF-A rat 205 amino acid splice variant or VEGF-A human 206 amino acid splice variant.

As used herein, "VEGF-A 188/18911" refers to the VEGF-A rat 188 amino acid splice variant or VEGF-A human 189 amino acid splice variant.

As used herein, "VEGF-A 164/165" refers to the VEGF-A rat 164 amino acid splice variant or VEGF-A human. 165 amino acid splice variant.

As used herein, "VEGF-A 144/145" refers to the VEGF-A rat 144 amino acid splice variant or VEGF-A human 145 amino acid splice variant.

As used herein, "VEGF-A 120/121" refers to the VEGF-A rat 120 amino acid splice variant or VEGF-A human 121 amino acid splice variant.

As used herein, "VEGF-A 110" refers to the VEGF-A human 110 amino acid splice variant.

TGF β Inhibition

Described herein are compounds that can be used in the methods and kits described herein for the differentiation of Isl1+ primordial progenitor cells into cardiac vascular lineages, e.g., Isl1+/CD31+ cells. Exemplary compounds for use in the methods and kits described herein as TGFβ inhibitors, such as TGFBR1 inhibitors include those described herein, as well as other TGFBRI inhibitors, e.g., the compounds described herein as ALK5i, also known as SB431542. SB431542 Is a Potent and Specific Inhibitor of Transforming Growth Factor-13 Superfamily Type I Activin Receptor-Like Kinase (ALK) Receptors ALK4, ALK5, and ALK7 (Inman et al., Molecular Pharmacology 2002, 62; 65-74)

Without wishing to be bound to theory, activin receptor-like kinase (ALK) 5 inhibitors block the TGF-signaling pathway. Also, the use of any ALK-5 inhibitors can be used in the methods and kits disclosed herein for the directed differentiation of Isl1+ primordial progenitor along vascular lineages. In one embodiment, one or more of the following compounds may be used. Manufacturer designation has been provided where available. The compounds are commercially available, for example from Sigma, P.O. Box 14508, St. Louis, Mo.

In an alternative embodiment, an inhibitor of ALK5 is A-83-01 or SB431542 as disclosed in WO2009/117439, which is incorporated herein in its entirety by reference. In some embodiments, a TGF beta receptor (e.g., ALK5) inhibitors can include antibodies to, dominant negative variants of, and antisense nucleic acids that suppress expression of, TGF beta receptors (e.g., ALK5). Exemplary TGFβ receptor/ALK5 inhibitors include, but are not limited to, SB431542 (see, e.g., Inman, et al, Molecular Pharmacology 62(1):65-74 (2002)), A-83-01, also known as 3-(6-Methyl-2-pyridinyl)-N-phenyl-4-(4-quinolinyl)-1H-pyrazole-1-carbothioamide (see, e.g., Tojo, et al, Cancer Science 96(11):791-800 (2005), and commercially available from, e.g., Toicris Bioscience); 2-(3-(6-Methylpyridin-2-yl)-1H-pyrazol-4-yl)-1,5-naphthyridine, Wnt3a/BIO (see, e.g., Dalton, et al, WO2008/094597, which is herein incorporated in its entirety by reference), BMP4 (see, Dalton, supra), GW788388 (-(4-[3-(pyridin-2-yl)-1H-pyrazol-4-yl]pyridm-2-yl}-N-(tetrahydro-2H-pyran-4-yl)benzamide) (see, e.g., Gellibert, et al, Journal of Medicinal Chemistry 49(7):2210-2221 (2006)), SM16 (see, e.g., Suzuki, et al, Cancer Research 67(5):2351-2359 (2007)), IN-1130 (3-((5-(6-methylpyridin-2-yl)-4-(quinoxalin-6-yl)-1H-imidazol-2-yHmethyl)benzamide) (see, e.g., Kim, et al, Xenobiotica 38(3):325-339 (2008)), GW6604 (2-phenyl-4-(3-pyridin-2-yl-1H-pyrazol-4-yl)pyridine) (see, e.g., de Gouville, et al., Drug News Perspective 19(2):85-90 (2006)), SB-505124 (2-(5-benzo[1,3]dioxol-5-yl-2-tert-butyl-3H-imidazol-4-yl)-6-methylpyridine hydrochloride) (see, e.g., DaCosta, et al., Molecular Pharmacology' 65(3):744-752 (2004)) and pyrimidine derivatives (see, e.g., those listed in Stiefl, et al., WO2008/006583, herein incorporated in its entirety by reference).

Further, while "an ALK5 inhibitor" is not intended to encompass non-specific kinase inhibitors, an "ALK5 inhibitor (ALK5i)" should be understood to encompass inhibitors that inhibit ALK4 and/or ALK7 in addition to ALK5, such as, for example, SB-431542 (see, e.g., Inman, et al, J Mol. Pharmacol. 62(1): 65-74 (2002).

As disclosed herein, the inventors demonstrate the that contacting the cells with an ALK5i increases the vasculargenic development of Isl1+ primordial progenitors and promotes vascular commitment into Isl1+/CD31+ cells by at least 4 to 5-fold.

In some embodiments, contacting a population of Isl1+ primordial progenitor cells with a TGFβ inhibitor, e.g., a ALK5i increases the efficiency of differentiation along vasculargenic lineages to Isl1+/CD31+ cells by about at least about 2-fold, or at least about 3-fold, or at least about 4-fold, or at least about 5-fold, or at least about 6-fold, or at least about 7-fold, more than about 7-fold as compared to the absence of TGFβ inhibitor, e.g., a ALK5i, e.g., SB-431542. In some embodiments, contacting Isl1+ primordial progenitors with TGFβ inhibitor, e.g., a ALK5i.e.g., SB-431542, results in a higher yield of Isl1+/CD31+ cells as compared to contacting a population of the downstream multipotent Isl1+ cardiovascular progenitors (MICP). In some embodiment, the increased yield is about at least 5%, or about a 10% increased yield, or about a 15% increased yield, or about a 30% increased yield, or about a 40% increased yield, or about a 50% increased yield, or a greater than 50% yield in Isl1+/CD31+ cells derived from Isl1+ primordial progenitors as disclosed herein, as compared to Isl1+/CD31+ cells derived from Isl1+/Nkx2.5+/KDR+ MICPs.

In some embodiments, a human Isl1+ primordial cell as disclosed herein is contacted with an ALK5i, e.g., SB-431542 at a concentration of between 15-25 ng/ml, or about at least about 10 ng/n1, or about at least about 12 ng/ml, or about at least about 15 ng/n1, or about at least about 17/nUml, or about at least about 20 ng/ml, or about at least about 22 ng/ml, or about at least about 25 ng/ml, or about at least about 27 ng/ml, or about at least about 30 ng/ml, or more than about at least about 30 ng/m to increase the efficacy to differentiate into Isl1+/CD31+ cells. In some embodiments the concentration of an ALK5i, e.g., SB-431542 is 18 ng/ml.

In some embodiments, a where the Isl1+ primordial cells as disclosed herein are from mouse, they can be contacted with an ALK5i, e.g., SB-431542 at a concentration of between 2-10 ng/ml, or about at least about 1 ng/n1, or about at least about 2 ng/ml, or about at least about 3 ng/ml, or about at least about 4 ng/ml, or about at least about 5 ng/ml, or about at least about 6 ng/ml, or about at least about 1 ng/ml, or about at least about 8 ng/ml, or about at least about 9 ng/ml, or about at least about 10 ng/ml, or about at least about 11 ng/ml, or about at least about 12 ng/ml, or more than about at least about 12 ng/ml increase the efficacy to differentiate into Isl1+/CD31+ cells. In some embodiments the concentration of an ALK5i, e.g., SB-431542 is 5 ng/ml.

In some embodiments, human Isl1+ primordial progenitors are contacted with an ALK5i, e.g., SB-431542 or a biological active homologue thereof for a period of at least one day, or a least 2 days, or a least about 3 days, or at least about 4 days or more, e.g., between 3-5 days, or 5-7 days, or 7-10 days, or 10-13 days or 13-16 days, beginning at any timepoint between Day 5 (D5) and Day 20 (D20) of cell age, for example, at D5, D6, D7, D8, D9, D10, D11, D12, D13, D14, D15, D16, D17, D18, D19 or D20 or at a timepoint after D20.

In some embodiments, where the Isl1+ primordial progenitors are derived from mouse ES cells, the Isl1+ progenitors are contacted with an ALK5i, e.g., SB-431542 or a biological active homologue thereof for a period of at least one day, or a least 2 days, or a least about 3 days, or at least about 4 days or more, e.g., between 3-5 days, or 5-7 days, or 7-10 days, beginning at any timepoint between Day 5 (D5) and Day 12 (D12) of cell age, for example, at D5, D6, D7, D8, D9, D10, D11 or D12 or at a timepoint after D12.

Inhibitors of TGFβ-Receptor Cell Signaling

In view of the data herein showing the effect of inhibiting ALK5 on the differentiation of Isl1+ primordial progenitors along vasculargenic developmental pathways to Isl1+/CD31+ cells, it is believed that inhibition of the TGFβ/activin pathway will have similar effects. Thus, any inhibitor (e.g., upstream or downstream) of the TGFβ/activin pathway can be used in combination with, or instead of, ALK5 inhibitors as described in each paragraph herein. Exemplary TGFβ/activin pathway inhibitors include but are not limited to: TGF beta receptor inhibitors, inhibitors of SMAD 2/3 phosphorylation, inhibitors of the interaction of SMAD 2/3 and SMAD 4, and activators/agonists of SMAD 6 and SMAD 7. Furthermore, the categorizations described below are merely for organizational purposes and one of skill in the art would know that compounds can affect one or more points within a pathway, and thus compounds may function in more than one of the defined categories.

Accordingly, in some embodiments, the differentiation of Isl1+ primordial progenitors into Isl1+/CD31+ vasculargenic progenitors can be produced by contacting a differentiated cell with an inhibitor of TGFβ cell signaling.

TGF beta receptor inhibitors can include antibodies to, dominant negative variants of and siRNA or antisense nucleic acids that target TGF beta receptors. Specific examples of inhibitors include but are not limited to SU5416; 2-(5-benzo[1,3]dioxol-5-yl-2-tert-butyl-3H-imidazol-4-yl)-6-methylpyridine hydrochloride (SB-505124); lerdelimumb (CAT-152); metelimumab (CAT-192); GC-1008; ID11; AP-12009; AP-11014; LY550410; LY580276; LY364947; LY2109761; SB-505124; SB-431542; SD-208; SM16; NPC-30345; Ki26894; SB-203580; SD-093; Gleevec; 3,5,7,2',4'-pentahydroxyfiavone (Morin); activin-M108A; P144; soluble TBR2-Fc; and antisense transfected tumor cells that target TGF beta receptors. (See, e.g., Wrzesinski, et al., Clinical Cancer Research 13(18):5262-5270 (2007); Kaminska, et al., Acta Biochimica Polonica 52(2):329-337 (2005); and Chang, et al, Frontiers in Bioscience 12:4393-4401 (2007).)

TGF-Beta Receptor (TGFβR) Inhibitors

The TGF-β receptors contemplated for use in the methods described herein for the differentiation of Isl1+ primordial progenitors into Isl1+/CD31+ vasculargenic progenitors can be produced by can be any TGF-β receptor including those from the Activin-like kinase family (ALK), the Bone Morphogenic Protein (BMP) family, the Nodal family, the Growth and Differentiation Factors family (GDF), and the TGF-β receptor family of receptors. TGF-β receptors are serine/threonine kinase receptors that effect various growth and differentiation pathways in the cell.

As used herein, the term "TGF-β signaling inhibitor" or "TGFβR inhibitor" or "TGFBR inhibitor" is any agent or small molecule (e.g. a compound) that inhibits TGF-β signal transduction by inhibiting any of the factors constituting the TGF-β signal transduction system pathway, such as TGF-β ligand, TGF-β Type I receptors, TGF-β Type II receptors, TGF-β Type III receptors ((3-glycan and endoglin), soluble forms of the TGF-β receptors, Smad proteins (1-8). A TGFBR inhibitor is any agent, including small molecules, antibodies against receptors and ligands implicated in the signaling pathway, nucleic acid based molecules (e.g., antisense, siRNA, aptamers and ribozymes) targeting the pathway members, or a combination thereof.

An "inhibitor" of a TGFβR, as the term is used herein, can function in a competitive or non-competitive manner, and can function, in one embodiment, by interfering with the expression of the TGFβR polypeptide. A TGFβR inhibitor includes any chemical or biological entity that, upon treatment of a cell, results in inhibition of a biological activity caused by activation of the TGFβR in response to binding of its natural ligand. While any TGF-β signaling pathway inhibitor can potentially be used in the methods described herein, it is preferable that a TGF-β signaling pathway inhibitor is either selective for, or specific for, a member of the TGF-β signaling pathway. By "specific" is meant that at the dose necessary for the inhibiting agent to inhibit the TGF-β signaling pathway, the inhibiting agent does not have any other substantial pharmacological action in the cell or host. By "selective" is meant that the dose of the inhibitor necessary for inhibition of the TGF-β signaling pathway is at least 2-fold lower than the dose necessary for activation or inhibition of another pharmacological action as measured by the $ED_{50}$ or $EC_{50}$ of the agent for each pharmacological effect; preferably the dose of inhibitor necessary for TGF-β pathway inhibition is at least 5-fold lower, at least 10 fold lower, at least 20-fold lower, at least 30-fold lower, at least 40-fold lower, at least 50-fold lower, at least 60-fold lower, at least 70-fold lower, at least 80-fold lower, at least 90-fold lower, at least 100-fold lower, at least 500-fold lower, at least 1000 fold lower or more, than the dose necessary for another pharmacological action. Thus, to be clear, the agents useful for the methods described herein primarily inhibit the TGF-β signaling pathway with only minor, if any, effects on other pharmacological pathways, and the dose used for inhibition of the TGF-β signaling pathway is sub-clinical or sub-threshold for other pharmacological responses.

Such an inhibitor can act by binding to the intracellular domain of the receptor and blockade of its serine/threonine kinase activity (e.g., ATP binding site). Alternatively, such an inhibitor can act by occupying or sterically hindering the ligand binding site (or a portion thereof) of the TGFβR, thereby rendering the receptor inaccessible to binding by the natural ligand, which prevents activation by that ligand. In addition, the TGFβR inhibitor can also bind to a non-ligand binding site and, for example, produce a conformational shift in the TGFβR, such that a ligand of the TGFβR can no longer access the binding site. An inhibitor can be, for example, a competitive inhibitor, a non-competitive inhibitor, an inverse agonist or a partial agonist of the TGFβR.

Alternatively, such an inhibitor can act by modulating the heterodimerization of TGFβR polypeptides, the interaction of TGFβR with other proteins, or the ubiquitination or endocytic degradation of the receptor. TGFβR inhibitors, include, but are not limited to small molecules, antibodies or antigen-binding antibody fragments, antisense constructs, siRNAs and ribozymes.

The receptor activity of a TGF-β receptor can be measured, for example, as described by Laping, N J., et al (2002) Molecular Pharmacology 62(1):58-64, which is herein incorporated by reference in its entirety. In addition, the dose-response curve for a TGF-β receptor inhibitor can be determined by measuring TGF-β receptor activity over a variety of inhibitor concentrations using the method of Laping, N J., et al (2002).

Without wishing to be bound by theory, the transforming growth factor beta (TGFβ) signaling pathway is involved in many cellular processes in both the adult organism and the developing embryo including cell growth, cell differentiation, apoptosis, cellular homeostasis and other cellular functions. In spite of the wide range of cellular processes that the TGFβ signaling pathway regulates, the process is relatively simple. TGFβ superfamily ligands bind to a type II receptor, which recruits and phosphorylates a type I receptor. The type I receptor then phosphorylates receptor-regulated SMADs (R-SMADs) which can now bind the coSMAD SMAD4. R-SMAD/coSMAD complexes accumulate in the nucleus where they act as transcription factors and participate in the regulation of target gene expression.

TGFβ receptors are single pass serine/threonine kinase receptors. They exist in several different isoforms that can be homo- or heterodimeric. The number of characterized ligands in the TGFβ superfamily far exceeds the number of known receptors, suggesting the promiscuity that exists between the ligand and receptor interactions.

TGF can be found in many different tissue types, including brain, heart, kidney, liver and testes. Over-expression of TGF can induce renal fibrosis, causing kidney disease, as well as diabetes, and ultimately end-stage renal disease (ESRD). Recent developments have found that, using certain types of protein antagonists against TGFβ receptors, can halt and in some cases reverse the effects of renal fibrosis.

Three TGF-β receptor types can be distinguished by their structural and functional properties. Receptor types I and II have similar ligand binding affinities and can only be distinguished from each other by peptide mapping, both receptor types I and II have a high affinity for TGF-β1 and low affinity for TGF-β2. TGF-β receptor type III has a high affinity for both TGF-β1 and -β2 and in addition TGF-β1.2.

Transforming growth factor, beta receptor I (herein termed "TGFBR1") (activin A receptor type II-like kinase, 53 kDa) is a TGF beta receptor. TGFBR1 is its human gene. The protein encoded by this gene forms a heteromeric complex with type II TGF-beta receptors when bound to TGF-beta, transducing the TGF-beta signal from the cell surface to the cytoplasm. The encoded protein is a serine/threonine protein kinase. Mutations in this gene have been associated with Loeys-Dietz aortic aneurysm syndrome (LDAS).

Transforming growth factor, beta receptor II (70/80 kDa) is a TGF beta receptor. TGFBR2 is its human gene. This gene encodes a member of the Ser/Thr protein kinase family and the TGFB receptor subfamily. The encoded protein is a transmembrane protein that has a protein kinase domain, forms a heterodimeric complex with another receptor protein, and binds TGF-beta. This receptor/ligand complex phosphorylates proteins, which then enter the nucleus and regulate the transcription of a subset of genes related to cell proliferation. Mutations in this gene have been associated with Marfan Syndrome, Loeys-Dietz Aortic Aneurysm Syndrome, Osler-Weber-Rendu syndrome, and the development of various types of tumors. Alternatively spliced transcript variants encoding different isoforms have been characterized.

Transforming growth factor β (TGF-β) is a member of a large family of pleiotropic cytokines that are involved in many biological processes, including growth control, differentiation, migration, cell survival, adhesion, and specification of developmental fate, in both normal and diseased states. TGF-β superfamily members signal through a receptor complex comprising a type II and type I receptor, both serine/threonine kinases.

In some embodiments, a small molecule inhibitor referred to herein as SB-431542 can be used in the methods as disclosed herein to promote the differentiation of Isl1+ primordial progenitors into Isl1+/CD31+ vasculargenic progenitors, as SB-431542 is an inhibitor of activin receptor-like kinase (ALK)$_5$ (the TGF-β type I receptor). As disclosed herein in the Examples and in FIGS. 18A-18C and 19, the inventors demonstrate that SB-431542 increases the efficiency of differentiation of both mouse and human Isl1+ primordial progenitors to Isl1+/CD31+ vasculargenic progenitors. SB-431542 has previously been reported to be useful to maintain and expand human embryonic stem cell-derived endothelial cells, as disclosed in James et al., Nature Biotech, 28, 161-166, 2010, which is incorporated herein in its entirety by reference. In particular, James et al., demonstrate that inhibition of TGFβ resulted in the expansion of endothelial cells from human ES cells, and maintained the Id1+ expression for preservation of the endothelial cell commitment. However in contrast to the present invention, James et al., did not mention or discuss that TGFβ inhibition, e.g., using SB-431542 could be used to differentiate Isl1+ primordial progenitors along an endothelial linage.

In one embodiment, the inhibition of a TGF-β receptor useful for the methods described herein for promoting the differentiation of Isl1+ primordial progenitors into Isl1+/CD31+ vasculargenic progenitors is the inhibition of an ALK4, ALK5, or ALK7 receptor. In another embodiment, the TGF-β receptor inhibited by the methods described herein to promote the differentiation of Isl1+ primordial progenitors into Isl1+/CD31+ vasculargenic progenitors is an ALK5 receptor. In another embodiment, downstream effectors of any of the aforementioned TGF-beta receptor signaling pathways can be targeted directly to effect cell reprogramming with the methods described herein.

If desired, one of skill in the art can locate the protein sequence of any of the TGF-β receptors by simply searching "transforming growth factor beta receptor" in a protein sequence database such as NCBI. Some non-limiting examples of protein sequence accession numbers for TGF-β receptors are P36897.1 (SEQ ID NO: 1), Q5T7S2 (SEQ ID NO: 2), Q61R47, P37173 (SEQ ID NO: 3), Q6A176 (not shown), Q706C0 (not shown), Q706C1 (not shown), and Q03167.2 (SEQ ID NO: 4), among others.

TGF-β1 is a prototypic member of a family of cytokines including the TGF-βs, activins, inhibins, bone morphogenetic proteins and Mullerian-inhibiting substance, that signal through a family of single transmembrane serine/threonine kinase receptors. These receptors can be divided into two classes, the type I or activin like kinase (ALK) receptors and type II receptors. The ALK receptors are distinguished from the type II receptors in that the ALK receptors (a) lack the serine/threonine rich intracellular tail, (b) possess serine/threonine kinase domains that are very homologous between type I receptors, and (c) share a common sequence motif called the GS domain, consisting of a region rich in glycine and serine residues. The $G_s$ domain is at the amino terminal end of the intracellular kinase domain and is critical for activation by the type II receptor. Several studies have reported that TGF-β signaling requires both the ALK and type II receptors. Specifically, the type II receptor phosphorylates the GS domain of the type I receptor for TGF-β, ALK5, in the presence of TGF-β. The ALK5, in turn, phosphorylates the cytoplasmic proteins Smad2 and Smad3 at two carboxy terminal serines. The phosphorylated Smad proteins translocate into the nucleus and activate genes that contribute to e.g., the production of extracellular matrix.

Activin ligands transduce signals in a manner similar to TGF-β ligands. Activins bind to and activate ALK receptors, which in turn phosphorylate Smad proteins such as Smad2 and Smad3. The consequent formation of a hetero-Smad complex with Smad4 results in the activin-induced regulation of gene transcription.

Smad proteins are exemplary downstream signal transduction factors in the TGF-beta pathway and therefore can be activated or inhibited directly to effect reprogramming (e.g., by treating a cell with an activator or inhibitor of a Smad protein). In one embodiment, an activator of Smad 7 is used to effect cell reprogramming. In another embodiment, inhibition of Smad 2, 3, or 5 is used to effect cell reprogramming.

Inhibitors of SMAD 2/3 phosphorylation can include antibodies to, dominant negative variants of and antisense nucleic acids that target SMAD2 or SMAD3. Specific examples of inhibitors include PD169316; 5B203580; SB-431542; LY364947; A77-01; and 3,5,7,2',4'-pentahydroxyflavone (Morin). (See, e.g., Wrzesinski, supra; Kaminska, supra; Shimanuki, et al., Oncogene 26:3311-3320 (2007); and Kataoka, et al, EP1992360, incorporated herein by reference.) Inhibitors of the interaction of SMAD 2/3 and smad4 can include antibodies to, dominant negative variants of and antisense nucleic acids that target SMAD2, SMAD3 and/or smad4. Specific examples of inhibitors of the interaction of SMAD 2/3 and SMAD4 include but are not limited to Trx-SARA, Trx-xFoxH1b and Trx-Lef1. (See, e.g., Cui, et al, Oncogene 24:3864-3874 (2005) and Zhao, et al., Molecular Biology of the Cell, 17:3819-3831 (2006).)

Activators/agonists of SMAD 6 and SMAD 7 include but are not limited to antibodies to, dominant negative variants of and antisense nucleic acids that target SMAD 6 or SMAD 7. Specific examples of inhibitors include but are not limited to smad7-as PTO— oligonucleotides. (See, e.g., Miyazono, et al., U.S. Pat. No. 6,534,476, and Steinbrecher, et al., US2005119203, both incorporated herein in their entirety by reference.)

Anti-TGFβ3 Antibodies

In some embodiments, the inhibitor of TGFβ cell signaling used to replace Sox2 is an anti-TGFβ antibody. Antibodies to anti-TGFβ are well known in the art, and include pan specific anti-TGFB from R&D (cat No: Ab-100 NA) and specific anti-TGFβRII from R&S systems (Cat No. AB-13 NA) as disclosed herein in the Examples.

Other Inhibitors of TGF β Cell Signaling

Small molecule inhibitors of TGFβ signaling pathway are known in the art e.g., Callahan J F et al., J. Med. Chem. (2002) 45: 999-1001; Sawyer J S et al., J. Med. Chem. (2003) 46, 3953-3956; Gellibert F et al., J. Med. Chem. (2004) 47: 4494-4506; Tojo Metal., Cancer Sci. (2005) 96: 791-800; Valdimarsdottir G et al., APMIS (2005) 113: 773-789 and Petersen et al., Kidney International (2008) 73: 705-715. Each of these references is incorporated by reference in its entirety. Non-limiting examples of small molecule inhibitors of TGFβ signaling pathway include Dihydropyrroloimidazole Analogues (e.g. SKF-104365), Triarylimidazole Analogues (e.g., SB-202620 and SB-203580), RL-0061425, 1,5-naphthyridine aminothiazole and pyrazole derivatives (e.g., 4-(6-Methyl-pyridin-2-yl)-5-(1,5-naphthyridin-2-yl)-1,3-thiazol-2-amine and 2-[3-(6-Methyl-pyridin-2-yl)-1H-pyrazol-4-yl]-1,5-naphthyridine), 4-(5-benzo[1,3]dioxol-5-yl-4-pyridin-2-yl-1H-imidazol-2-yl)-benzamide (SB431542), 4-(4-[3-(Pyridin-2-yl)-1H-pyrazol-4-yl)pyridin-2-yl)-N-(tetrahydro-2Hpyran-4-yl) benzamide (GW788388), A-83-01, Decorin, Lefty1, Lefty2, Follistatin, Noggin, Chordin, Cerberus, Cerberus, Gremlin, Inhibin, and BIO (6-bromoindirubin-3' oxime).

In some embodiments, other non-limiting examples of small molecule inhibitors of TGFβRs which can be used to replace exogenous Sox2 include for example, 2-(3-(6-Methylpyridin-2-yl)-1H-pyrazol-4-yl)-1,5 napththyridine, [3-(Pyridin-2-yl)-4-(4-quinoyl)]-1H-pyrazole, and 3-(6-Methylpyridin-2-yl)-4-(4-quinolyl)-1-phenylthiocarbamoyl-1H-pyrazole, which can be purchased from Calbiochem (San Diego, Calif.). Other small molecule inhibitors include, but are not limited to, SB-431542 (see e.g., Halder et al., 2005; Neoplasia 7(5):509-521), SM16 (see e.g., Fu, K et al., 2008; Arteriosclerosis, Thrombosis and Vascular Biology 28(4): 665), and SB-505124 (see e.g., Dacosta Byfield, S., et al., 2004; Molecular Pharmacology 65:744-52), among others.

In one embodiment, the ALK5 inhibitor 2-(3-(6-Methylpyridin-2-yl)-1H-pyrazol-4-yl)-1,5 napththyridine is used with the methods described herein. This inhibitor is also referred to herein as ALK5 inhibitor II and is available commercially from Calbiochem (Cat. No. 616452; San Diego, Calif.). In one embodiment, the inhibitor is SB 431542, an ALK-4, -5, -7 inhibitor, commercially available from Sigma (product no. 54317; Saint Louis, Mo.). SB 431542 is also referred to by the following chemical names: 4-[4-(1,3-Benzodioxol-5-yl)-5-(2-pyridinyl)-1H-imidazol-2-yl]-benzamide, 4-[4-(3,4-methylenedioxyphenyl)-5-(2-pyridyl)-1H-imidazol-2-yl]-benzamide, or 4-(5-benzol[1,3]dioxol-5-yl-4-pyridin-2-yl-1H-imidazol-2-yl)-benzamide hydrate.

Small molecules inhibitors of TGF-β signaling can be classified based on the basic scaffold of the molecule. For example, TGF-β signaling inhibitors can be based on the dihydropyrrlipyrazole-based scaffold, imidazole-based scaffold, pyrazolopyridine-based scaffold, pyrazole-based scaffold, imidazopyridine-based scaffold, triazole-based scaffold, pyridopyrimidine-based scaffold, pyrrolopyrazole-based scaffold, isothiazole-based scaffold and oxazole-based scaffold.

Inhibitors of TGF-β signaling are described in Callahan, J. F. et al., J. Med. Chem. 45, 999-1001 (2002); Sawyer, J. S. et al., J. Med. Chem. 46, 3953-3956 (20031; Gellibert, F. et al., J. Med. Chem. 47, 4494-4506 (2004); Tojo, M. et al., Cancer Sci. 96: 791-800 (2005); Valdimarsdottir, G. et al., APMIS113, 773-389 (2005); Petersen et al. Kidney International 73, 705-715 (2008); Yingling, J. M. et al., Nature Rev. Drug Disc. 3, 1011-1022 (2004); Byfield, S. D. et al., Mol. Pharmacol., 65, 744-752 (2004); Dumont, N, et al., Cancer Cell 3, 531-536 (2003); WO Publication No. 2002/094833; WO Publication No. 2004/026865; WO Publication No. 2004/067530; WO Publication No. 209/032667; WO Publication No. 2004/013135; WO Publication No. 2003/097639; WO Publication No. 2007/048857; WO Publication No. 2007/018818; WO Publication No. 2006/018967; WO Publication No. 2005/039570; WO Publication No. 2000/031135; WO Publication No. 1999/058128; U.S. Pat. No. 6,509,318; U.S. Pat. No. 6,090,383; U.S. Pat. No. 6,419,928; U.S. Pat. No. 9,927,738; U.S. Pat. No. 7,223,766; U.S. Pat. No. 6,476,031; U.S. Pat. No. 6,419,928; U.S. Pat. No. 7,030,125; U.S. Pat. No. 6,943,191; U.S. Publication No. 2005/0245520; U.S. Publication No. 2004/0147574; U.S. Publication No. 2007/0066632; U.S. Publication No. 2003/0028905; U.S. Publication No. 2005/0032835; U.S. Publication No. 2008/0108656; U.S. Publication No. 2004/015781; U.S. Publication No. 2004/0204431; U.S. Publication No. 2006/0003929; U.S. Publication No. 2007/0155722; U.S. Publication No. 2004/0138188 and U.S. Publication No. 2009/0036382, the contents of each which are herein incorporated by reference in their entirety.

Oligonucleotide based modulators of TGF-β signaling, such as siRNAs and antisense oligonucleotides, are described in U.S. Pat. No. 5,731,424; U.S. Pat. No. 6,124,449; U.S. Publication Nos. 2008/0015161; 2006/0229266; 2004/0006030; 2005/0227936 and 2005/0287128, each of which are herein incorporated by reference in their entirety. Other antisense nucleic acids and siRNAs can be obtained by methods known to one of ordinary skill in the art.

Exemplary inhibitors of TGF-β signaling include, but are not limited to, AP-12009 (TGF-β Receptor type II antisense oligonucleotide), Lerdelimumab (CAT 152, antibody against TGF-β Receptor type II) GC-1008 (antibody to all isoforms of human TGF-β), ID11 (antibody to all isoforms of murine TGF-β), soluble TGF-13, soluble TGF-β Receptor type II, dihydropyrroloimidazole analogs (e.g., SKF-104365), triarylimidazole analogs (e.g., SB-202620 (4-(4-(4-fluorophenyl)-5-(pyridin-4-yl)-1H-imidazol-2-yl)benzoic acid) and SB-203580 (4-(4-Fluorophenyl)-2-(4-methylsulfinyl phenyl)-5-(4-pyridyl)-1H-imidazole)), RL-0061425, 1,5-naphthyridine aminothiazole and pyrazole derivatives (e.g., 4-(6-methyl-pyridin-2-yl)-5-(1,5-naphthyridin-2-yl)-1,3-thiazole-2-amine and 2-[3-(6-methyl-pyridin-2-yl)-1H-pyrazole-4-yl]-1,5-naphthyridine), SB-431542 (4-(5-Benzol[1,3]dioxol-5-yl-4-pyridin-2-yl-1H-imidazol-2-yl)-benzamide), GW788388 (4-(4-(3-(pyridin-2-yl)-1H-pyrazol-4-yl)pyridin-2-yl)-N-(tetrahydro-2H-pyran-4-yl) benzamide), A-83-01 (3-(6-Methyl-2-pyridinyl)-N-phenyl-4-(4-quinolinyl)-1H-pyrazole-1-carbothioamide), Decorin, Lefty 1, Lefty 2, Follistatin, Noggin, Chordin, Cerberus, Gremlin, Inhibin, BIO (6-bromo-indirubin-3'-oxime), Smad proteins (e.g., Smad6, Smad7), and Cystatin C.

Inhibitors of TGF-β signaling also include molecules which inhibit TGF-β Receptor type I. Inhibitors of TGF-β Receptor type I are described in Byfield, S. D., and Roberts, A. B., Trends Cell Biol. 14, 107-111 (2004); Sawyer J. S. et al., Bioorg. Med. Chem. Lett. 14, 3581-3584 (2004); Sawyer, J. S. et al., J. Med. Chem. 46, 3953-3956 (2003); Byfield, S. D. et al., Mol. Pharmacol. 65, 744-752 (2004); Gellibert, F. et al., J. Med. Chem. 47, 4494-4506 (2004); Yingling, J. M. et al., Nature Rev. Drug Disc. 3, 1011-1022 (2004); Dumont, N, et al., Cancer Cell 3, 531-536 (2003); Tojo, M. et al., Cancer Sci. 96: 791-800 (2005); WO Publication No. 2004/026871; WO Publication No. 2004/021989; WO Publication No. 2004/026307; WO Publication No. 2000/012497; U.S. Pat. No. 5,731,424; U.S. Pat. No. 5,731,144; U.S. Pat. No. 7,151,169; U.S. Publication No. 2004/00038856 and U.S. Publication No. 2005/0245508, contents of all of which are herein incorporated in their entireties.

Exemplary inhibitors of TGF-β Receptor type I include, but are not limited to, soluble TGF-β Receptor type I; AP-11014 (TGF-β Receptor type I antisense oligonucleotide); Metelimumab (CAT 152, TGF-β Receptor type I antibody); LY550410; LY580276 (3-(4-fluorophenyl)-5,6-dihydro-2-(6-methylpyridin-2-yl)-4H-pyrrolo[1,2-b]pyrazole); LY364947 (4-[3-(2-Pyridinyl)-1H-pyrazol-4-yl]-quinoline); LY2109761; LY573636 (N-((5-bromo-2-thienyl)sulfonyl)-2,4-dichlorobenzamide); SB-505124 (2-(5-Benzo[1,3]dioxol-5-yl-2-tert-butyl-3H-imidazol-4-yl)-6-methylpyridine); SD-208 (2-(5-Chloro-2-fluorophenyl)-4-[(4-pyridyl)amino] pteridine); SD-093; KI2689; SM16; FKBP12 protein; 3-(4-(2-(6-methylpyridin-2-yl)H-imidazo[1,2-a]pyridin-3-yflquinolin-7-yloxy)-N,N-dimethylpropan-1-amine;

RNAi Inhibitors of TGFβ Receptor

TGFBR1 mRNA has been successfully targeted using siRNAs; see for example, which can be obtained from Santacruz Biotechnology (cat No: sc-40222), which is incorporated herein by reference. Others siRNA molecules may be readily prepared by those of skill in the art based on the known sequence of the target mRNA. To avoid doubt, the sequence of a human TGFBR cDNA is provided at, for example, GenBank Accession Nos. P36897.1 (SEQ ID NO: 1), Q5T7S2 (SEQ ID NO: 2), Q61R47, P37173 (SEQ ID NO: 3), Q6A176 (not shown), Q706C0 (not shown), Q706C1 (not shown), and Q03167.2 (SEQ ID NO: 4), among others.

In some embodiments, at least one or a combination of growth factors can be administered locally at the same site of the implantation of ISL1+ progenitors, or alternatively, at least one or a combination of growth factors can be administered systemically to the animal. In another embodiment, the administration of at least one or a combination of growth factors, such as VEGF can be administered at one or more timepoints, for example, multiple bolus administrations of at least one or a combination of growth factors. In alternative embodiments, the subject can be administered at least one or a combination of growth factors by continuous infusion, for example using infusion pumps or slow-release formulations of the growth factors by methods commonly known by one of ordinary skill in the art.

In some embodiments, the human ISL1+ primordial progenitors can be implanted into a subject as a substantially pure population of human ISL1+ progenitors, and in some embodiments, the population of human ISL1+ primordial progenitors is implanted in conjunction with an additional cell population. In some embodiments, a population of human ISL1+ primordial progenitors comprises a population of Isl1+/CD31+ vasculargenic progenitors differentiated from the human ISL1+ primordial cells, for example, at least about 0.2% or at least about 0.3%, or at least about 0.4%, or at least about 0.5%, or at least about 0.6%, or at least about 0.7%, or at least about 0.8%, or at least about 0.9%, or at least about 1.0%, or at least about 1.2%, or at least about 1.4%, or at least about 1.5%, or at least about 2.0%, or at least about 3.0%, or at least about 4.0%, or at least about 5.0%, or at least about 6.0%, or at least about 7.0%, or at least about 8.0%, or at least about 9.0%, or at least about 10% or more than 10% of the human ISL1+ primordial progenitors cell population are Isl1+/CD31+ vasculargenic progenitors.

In some embodiments, the human ISL1+ primordial progenitors can be implanted concurrently with the additional cell population, e.g. as a mixture, or substantially immediately before or after implantation of the additional cell population (e.g. concurrent administration) to generate the human vascularized cardiac tissue as disclosed herein. In alternative embodiments, there can be temporal separation of administration of the ISL1+ primordial progenitors and the additional population of cells, such as, for example, a subject can be implanted with a population of ISL1+ progenitors, in some embodiments at multiple timepoints, prior to, or after the implantation of the additional cell population. In some embodiments, the separation of administration of the different cell populations is at least about 1 hr, or at least about 2 hrs, or at least about 6 hrs, or at least about 12 hrs, or at least about 24 hrs, or a least about 48 hrs, or a least about 3 days, or at least about 4 days, or at least about 7 days, or at least about 2 weeks, or a least about 21 days, or at least about a month or more in duration.

The additional cells to be implanted in combination with the human ISL1+ cells can be from any origin and any species. Preferably, in some embodiments, the cells are human cells. In some embodiments, the cells are human committed ventricular progenitors (CVP) as disclosed in International Patent Application PCT/US2009/060224, which is incorporated herein in its entirety by reference. In some embodiments, the cells are isl1+/CD31+ vasculargenic progenitors, as disclose herein. In some embodiments, where the population of ISL1+ primordial progenitors is mixed with a population of other cells, such as e.g., CVPs or Isl1+/CD31+ cells, any ratio of the cells which are human ISL1+ primordial progenitors to cells which belong to another cell population can be used, for example, 1:1, 2:1, 3:1, 4:1, 5:1, 6:1, 7:1, 8:1, 9:1, 10:1, 15:1, 20:1, 50:1, 100:1, 200:1, 300:1, 500:1 and 1000:1 ratios, or 1:1000, 1:500, 1:300, 1:200, 1:100, 1:50. 1:20, 1; 15, 1:10, 1:5, 1:4, 1; 3 and 1:2 where the ratios relates to the number of human ISL1+ primordial progenitors to the number of cells of another cell population (e.g., CVPs or isl1+/CD31+ vasculargenic progenitors).

In some embodiments, the number or amount of ISL1+ primordial progenitors implanted into a subject can be determined by one of ordinary skill in the art, and depends on part on the site of implantation and the species of subject which is the recipient of the implanted cells. For example, a pig or monkey or human subject can have a greater number of human ISL1+ primordial progenitors implanted than a rodent subject, such as a mouse. Similarly, the site of impanation can determine the number of human ISL1+ progenitors implanted, for example more human ISL1+ primordial progenitors can be implanted into a peritoneal cavity or subcutaneous space as compared to a kidney capsule. By way of example only, one can implant at least about 2,000 cells, for example about 500-1000, or about 1000-2000, or about 2000-5000 cells into the kidney capsule of a mouse.

In some embodiments, the number of human ISL1+ primordial progenitors implanted is the total amount of cells which is less than (e.g. about 5% or about 0% less) the total amount of cells where the cells begin to compete for nutrients and thus decrease in viability after implantation. In some embodiments, the amount or number of human ISL1+ primordial progenitors implanted is the amount in which at least about 50% or at least about 60% or at least about 70% or at least about 80% or at least about 90% or at least about 95% or at least about 98% or at least about 99% or more of the originally implanted human ISL1+ primordial progenitors are viable after about 2 weeks of implantation, or a after about 3 weeks or a month after implantation into a subject.

In some embodiments, the ISL1+ primordial progenitors do not proliferate or self-renew once implanted into a subject. The inventors have demonstrate a population of human ISL1+ primordial progenitors do not express Ki67 marker, which indicates the ISL1+ primordial progenitors are not proliferating post implantation. Thus, the inventors have demonstrated minimal risk of formation of teratomas after implantation of ISL1+ primordial progenitors into a subject.

In some embodiments, the ISL1+ primordial progenitor can be genetically modified prior to implantation into a subject and formation of vascularized human cardiac tissue as disclosed herein. In some embodiments, the human ISL1+ primordial can be genetically modified to prolong the survival of humanized vascularized cardiac graft tissue by inhibiting apoptosis, promoting survival pathways, and minimizing immune rejection of the isl1+ progenitors and their differentiated cardiac cells. In some embodiments, the ISL1+ progenitors are genetically modified to express truncated Creb312, as disclosed in U.S. Patent Application 61/145,208, filed on Jan. 16, 2009, which is incorporated herein in its entirety by reference. In some embodiments, the ISL1+ primordial progenitors can express growth factors, such as cardiotrophic factors and angiogenic factors such as VEGF. In some embodiments, the expression of the transgenes are regulated by tissue-specific promoters and/or inducible promoters as commonly known by methods of one of ordinary skill in the art.

In some embodiments, the ISL1+ primordial progenitors are genetically modified to correct a genetic defect, for example, to correct a SNP or genetic variation which contributes to a cardiac disease, disorder or dysfunction. In some embodiments, the ISL1+ progenitor can genetically modified to express dystrophin, for example where the ISL1+ progenitors are implanted into a subject (e.g. human or animal model) with Duchene's muscular dystrophy.

In some embodiments, the human ISL1+ primordial progenitors are implanted into a host subject for a sufficient amount of time to generate human vascularized cardiac tissue as disclosed herein, where the human vascularized cardiac tissue can then be removed from the subject and implanted into a different subject, for example a human subject. Thus, the human ISL1+ primordial progenitors in the first subject serves as a bioreactor for generation of the human vascularized cardiac tissue, which is then implanted, for example for therapeutic use, into a second subject, typically a human subject. Typically the first subject (e.g. the bioreactor subject) is an animal subject, where the implanted human ISL1+ primordial progenitors is a xenograft, and which is then removed and implanted into a second subject, typically a human subject. However, the human vascularized cardiac tissue removed from the first subject (e.g. bioreactor subject) can be implanted into a second animal subject, such as monkey or the like, and production of an in vivo model of vascular disease as disclosed herein.

In another aspect of the invention, the methods provide use of human vascularized cardiac tissue. In one embodiment of the invention, the human vascularized cardiac tissue may be used for the production of a pharmaceutical composition, for the use in implantation (e.g. transplantation) into subjects in need of cardiac tissue transplantation, for example but not limited to subjects with congenital and acquired heart disease and subjects with vascular diseases. In one embodiment, the human vascularized cardiac tissue may be genetically modified. In another aspect, the subject may have or be at risk of heart disease and/or vascular disease. In some embodiments, the human vascularized cardiac tissue may be autologous and/or allogenic. In some embodiments, the subject is a mammal, and in other embodiments the mammal is a human.

In Vivo Humanized Model of Vascularized Disease

In some embodiments where human ISL1+ progenitors are implanted into an animal subject, the animal can be use as an in vivo humanized model of vascular disease. For example, an animal model which comprises functional vascularized human cardiac tissue, can be used to screen for agents which affect any one, or a combination of viability, functionality, contractibility, differentiation of the human cardiac tissue.

Accordingly, one embodiment relates to the use of an in vivo humanized model of vascular disease as an assay, for example to assess drug toxicity (e.g. cardiotoxicity) on human heart tissue in vivo (e.g. to identify agents which increase apoptosis, decrease viability, modulate (e.g. increase or decrease by a statistically significantly amount) contractibility and/or conductivity of heart tissue). In some embodiments, the drugs and/or compounds can be existing drugs or compounds, and in other embodiments, the drugs or compounds can be new or modified drugs and compounds.

In another embodiment, an in vivo humanized model of vascular disease can be used as an assay for example to identify agents which increase and decrease coronary blood flow to human vascularized heart tissue in vivo. For example, in one embodiment, the human vascularized heart tissue could be given atherosclerosis, for example by implanting the human ISL1+ progenitors into a LDR −/− mouse and feeding the mouse a high fat diet.

Another aspect of the invention relates use of the in vivo humanized model of vascular disease as disclosed herein to screen for agents, for example molecules and genes involved in biological events. In such an embodiment, the biological event is an event that affects the differentiation of a human ISL1+ progenitor, or the function of the human vascularized cardiac tissues. The in vivo humanized model of vascular disease can be used to identify any agent which promotes the differentiation, proliferation, survival, regeneration, maintenance of the undifferentiated state of the ISL1+ progenitor, and/or inhibition or down-regulation of differentiation.

In another embodiment, the in vivo humanized model of vascular disease can be used to assess the effect of genetic variation (e.g. ethnicity, human mutations or gene variants or polymorphism) on cardiac function. For example, the effect of different environmental factors, such as, for example, obesity, high fat diet, lack of exercise, can be assessed in human vascularized cardiac tissue in vivo generated from ISL1+ progenitors from different genetic backgrounds. In an alternative embodiment, the effect (e.g. efficacy and/or safety profile) of different therapeutic agents and cardiac drugs can be assessed in human vascularized cardiac tissue in vivo generated from ISL1+ progenitors from different genetic backgrounds. Accordingly, in some embodiments, an in vivo humanized model of vascular disease is generated using human primordial ISL1+ progenitors which are a variant human primordial ISL1+ progenitor, for example but not limited to a genetic variant and/or a genetically modified human primordial ISL1+ progenitor.

In another embodiment, the in vivo humanized model of vascular disease as disclosed herein can be used as an assay for example to identify other cells which can be implanted in combination with the human ISL1+ cells, for example, addition of committed ventricular progenitors (CVP) as disclosed in International Patent Application PCT/US2009/060224, which is incorporated herein in its entirety by reference.

In another embodiment, the in vivo humanized model of vascular disease can be used in an assay for studying the differentiation pathways of human primordial ISL1+ progenitors into multiple lineages, for example but not limited to, human cardiac, human smooth muscle and human endothelial cell lineages. In some embodiments, the human primordial ISL1+ progenitors can be genetically engineered to comprise markers operatively linked to promoters that are expressed in one or more of the lineages being studied.

In some embodiments, the in vivo humanized model of vascular disease can be used in an assay for studying the differentiation pathway of human ISL1+ progenitors into subpopulations of human cardiomyocytes. In some embodiments, the human ISL1+ progenitors can be genetically engineered to comprise markers operatively linked to promoters that drive gene transcription in specific cardiomyocyte subpopulations, for example but not limited to atrial, ventricular, outflow tract and conduction systems. In other embodiments, the human ISL1+ progenitors can be used in an assay for studying the role of cardiac mesenchyme on cardiovascular stem cells.

In alternative embodiments, the human ISL1+ progenitors used to generate human vascularized tissue, and for the generation the in vivo humanized model of vascular disease can comprise a mutation and/or polymorphism that relates to the disease phenotype, and in other embodiments, the human ISL1+ progenitor been genetically engineered to carry a mutation and/or polymorphism.

Any suitable animal can be used for implanting a population of ISL1+ cells to generate an in vivo humanized model of vascular disease as disclosed herein, for example, rodents (such as mice, rats), monkeys, pigs and the like. In some embodiments, the subject animal is a transgenic or knockout animal, e.g., a transgenic mice or knock out mice. In some embodiments, the subject animal is a humanized mouse, such as the SCID mouse.

In some embodiments, an in vivo humanized model of vascular disease as disclosed herein is useful as an in vivo assays and screening method to detect agents that are active on ISL1+ primordial progenitors, for example, to screen for agents that affect the differentiation of the human ISL1+ primordial progenitors, including differentiation along the cardiomyocyte lineage. Of particular interest are screening assays for agents that are active on human ISL1+ primordial progenitors.

In some embodiments, the in vivo humanized model of vascular disease as disclosed herein can be used to identify an agent for the effect of the agent assessed by monitoring output parameters, such as expression of markers, cell viability, differentiation characteristics, multipotenticy capacity and the like.

In some embodiments, the in vivo humanized model of vascular disease can be produced by implanting a population of human ISL1+ primordial progenitors into an immunodeficient animal (such as nude mice, such as SCID mice, or animals rendered immunodeficient chemically or by irradiation). The human vascular heart tissues can be harvested after a period of regrowth, and assessed as to whether the human vascular heart tissue are still present, viable and functioning normally.

In some embodiments, the ISL1+ primordial progenitors administered to the subject can express a detectable label (such as green fluorescent protein, or beta-galactosidase); that have been prelabeled (for example, with BrdU or [3H] thymidine), or by subsequent detection of a constitutive cell marker (for example, using human-specific antibody). The presence and phenotype of the administered ISL1+ primordial progenitors can be assessed by immunohistochemistry or ELISA using human-specific antibody, or by RT-PCR analysis using primers and hybridization conditions that cause amplification to be specific for human polynucleotides, according to published sequence data.

The effect of an agent administered to an in vivo humanized model of vascular disease can be assessed by the degree of cardiac recuperation that ensues from inflicting injury to the human vascular tissue. A number of animal models are available for such testing. For example, hearts can be cryoinjured by placing a precooled aluminum rod in contact with the surface of the anterior left ventricle wall (Murry et al., J. Clin. Invest. 98:2209, 1996; Reinecke et al., Circulation 100:193, 1999; U.S. Pat. No. 6,099,832). In larger animals, cryoinjury can be inflicted by placing a 30-50 mm copper disk probe cooled in liquid N2 on the anterior wall of the left ventricle for approximately 20 min (Chiu et al., Ann. Thorac. Surg. 60:12, 1995). Infarction can be induced by ligating the left main coronary artery (Li et al., J. Clin. Invest. 100:1991, 1997). Injured sites are treated with cell preparations of this invention, and the heart tissue is examined by histology for the presence of the cells in the damaged area. Cardiac function can be monitored by determining such parameters as left ventricular end-diastolic pressure, developed pressure, rate of pressure rise, and rate of pressure decay.

The ISL1+ primordial progenitors may be freshly isolated, cultured, genetically engineered as described above, or the like. The ISL1+ primordial progenitors may be environmentally induced variants of clonal cultures: e.g. split into independent cultures and grown under distinct conditions, for example with or without virus; in the presence or absence of other cytokines or combinations thereof. Alternatively, the ISL1+ primordial progenitors may be variants with a desired pathological characteristic. For example, the desired pathological characteristic includes a mutation and/or polymorphism which contribute to disease pathology.

In such an embodiment, the in vivo humanized model of vascular disease of the invention can be used to screen for agents which alleviate the pathology. In alternative embodiments, the in vivo humanized model of vascular disease can be assessed by the degree of cardiac recuperation that ensues from inflicting injury to the human vascular cardiac tissue of the invention can be used to screen for agents in which some stem cells comprising a particular mutation and/or polymorphism respond differently compared with human vascular cardiac tissue without the mutation and/or polymorphism, therefore the methods can be used for example, to assess an effect of a particular drug and/or agent on human vascular cardiac tissue from a defined subpopulation of people and/or cells, therefore acting as an in vivo high-throughput screen for personalized medicine and/or pharmogenetics. The manner in which human vascular cardiac tissue respond to an agent, particularly a pharmacologic agent, including the timing of responses, is an important reflection of the physiologic state of the human vascular cardiac tissue.

The use of the in vivo humanized model of vascular disease as disclosed herein provides significant advantages over existing method to assess agents on cardiac tissue, because the in vivo humanized model of vascular disease comprises human vascularized cardiac tissue which is formed from ISL1+ primordial cells in vivo, and is properly vascularized and comprises all the desired cell types of heart tissue, including cells of cardiomyocyte phenotypes, endothelial cell phenotypes, smooth muscle phenotypes, as well as characteristics and properties of functional heart tissue. This is highly advantageous as it provides a model of human heart tissue in vivo, which is significantly advantageous over existing cardiac function assays which either are assays using human heart tissue in vitro, or are in vivo models using non-human heart tissue.

In another embodiment, the in vivo humanized model of vascular disease as disclosed herein can be used as a model for studying differentiation pathways of ISL1+ primordial progenitors into multiple lineages, for example but not limited to, cardiac, smooth muscle and endothelial cell lineages. In some embodiments, the ISL1+ primordial progenitors can be genetically engineered to comprise markers operatively linked to promoters that are expressed in one or more of the lineages being studied. In some embodiments, the in vivo humanized model of vascular disease as disclosed herein can be used as a model for studying the differentiation pathway of human ISL1+ primordial progenitors into subpopulations of cardiomyocytes. In some embodiments, the human ISL1+ primordial progenitors may be genetically engineered to comprise markers operatively linked to promoters that drive gene transcription in specific cardiomyocyte subpopulations, for example but not limited to atial, ventricular, outflow tract and conduction systems.

In other embodiments, the in vivo humanized model of vascular disease as disclosed herein can be used as models for studying the role of cardiac mesenchyme on cardiovascular stem cells. In some embodiments, the human ISL1+ primordial progenitors can be from an ES cell source that leads to development of a normal heart or, alternatively, the human ISL1+ primordial progenitors can be isolated from an ES source which if developed has a congenital heart abnormality and lead to the formation of a heart with a congenital heart abnormality or dysfunction. In some embodiments the human ISL1+ primordial progenitors carries a mutation and/or polymorphism, and in other embodiments, the human ISL1+ primordial progenitors has been genetically engineered to carry a mutation and/or polymorphism.

In some embodiments, an agent administered to an in vivo humanized model of vascular disease as disclosed herein can be selected from a group of a chemical, small molecule, chemical entity, nucleic acid sequences, an action; nucleic acid analogues or protein or polypeptide or analogue of fragment thereof. In some embodiments, the nucleic acid is DNA or RNA, and nucleic acid analogues, for example can be PNA, pcPNA and LNA. A nucleic acid may be single or double stranded, and can be selected from a group comprising; nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide agent or fragment thereof, can be any protein of interest, for example, but not limited to; mutated proteins; therapeutic proteins; truncated proteins, wherein the protein is normally absent or expressed at lower levels in the cell. Proteins of interest can be selected from a group comprising; mutated proteins, genetically engineered proteins, peptides, synthetic peptides, recombinant proteins, chimeric proteins, antibodies, humanized proteins, humanized antibodies, chimeric antibodies, modified proteins and fragments thereof.

In some embodiment, at least one agent is administered to an in vivo humanized model of vascular disease as disclosed herein by any suitable means known to one of ordinary skill in the art. In some embodiments, administration occurs more than once, for example at multiple different time points. In some embodiments, the administration of an agent to a in vivo humanized model of vascular disease is continuous, for example via means of an infusion pump or cather or the like, or via a slow-release formulation of the agent. In some embodiments, the agent is administered locally to the site of the human vascularized cardiac tissue in the in vivo humanized model of vascular disease, or alternatively, systemically to the in vivo humanized model of vascular disease.

In some embodiments, an agent is administered to an in vivo humanized model of vascular disease via any or a combination of the following administration methods; systemic administration, intravenous, transdermal, intrasynovial, intramuscular, oral administration, parenteral administration, intraarterial administration, intrathecal administration, intraventricular administration, intraparenchymal, intracranial, intracisternal, intrastriatal, and intranigral administration, and intracoronary administration.

In some embodiments, the agents are conveniently administered to the an in vivo humanized model of vascular disease in a pharmacological applicable carrier, such as solution, or readily soluble form. The agents may be added in a pump (e.g. flow-through system), as a stream, intermittent or continuous, or alternatively, adding a bolus of the compound, singly or incrementally, to an otherwise static solution. In some embodiments, agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

In some embodiments, an agent may be applied to the media comprising the ISL1+ primordial cells prior to the implantation into the subject, where the agent contacts the ISL1+ primordial cells and induces its effects. Alternatively, the agent may be intracellular within the ISL1+ primordial progenitor as a result of introduction of the nucleic acid sequence into the cell and its transcription resulting in the production of the nucleic acid and/or protein agent within the cell.

In some embodiment, an agent also encompasses any action and/or event the in vivo humanized model of vascular disease as disclosed herein is are subjected to. As a non-limiting examples, an action can comprise any action that triggers a physiological change in human vascularized heart tissue in the in vivo humanized model of vascular disease as disclosed herein, for example but not limited to; heat-shock, ionizing irradiation, cold-shock, electrical impulse, light and/or wavelength exposure, UV exposure, pressure, stretching action, increased and/or decreased oxygen exposure, exposure to reactive oxygen species (ROS), ischemic conditions, fluorescence exposure etc. Environmental stimuli also include intrinsic environmental stimuli defined below. The exposure to agent may be continuous or non-continuous.

In some embodiments, the environmental stimuli includes a high fat diet and/or lack or excess of exercise. Any environmental stimuli which can lead to cardiovascular disease can be included, such as high stress, high cholesterol diet, high fat diet and the like. In such embodiments, the environmental stimuli are administered to the in vivo humanized model of vascular disease in the diet (e.g. oral administration) or exposure to stressful conditions, such as continuous noise or light, continuous duration of strobe or intermittent light, over-crowded housing of the subject, housing with aggressive same species subjects and the like.

In some embodiments, the in vivo humanized model of vascular disease is exposed to environmental conditions to induce coronary heart disease and/or cardiovascular disease, and then is administered at least one agent to counteract the effects of the environmental stimuli which lead to cardiovascular disease. By way of an example only, in some embodiments, the in vivo humanized model of vascular disease is a LDL knockout mouse which comprises human vascularized heart tissue as disclosed herein, which is fed a high fat diet to induce cardiovascular disease. In such embodiments, the LDL −/− animal subject which is fed a high fat diet which comprises human vascularized heart tissue is administered an agent to monitor if the agent decreases the symptoms of cardiovascular disease in the subject.

The term "agent" refers to any chemical, entity or moiety, including without limitation synthetic and naturally-occurring non-proteinaceous entities. In certain embodiments the compound of interest is a small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

In some embodiments, the agent is an agent of interest including known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like. Candidate agents also include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Also included as agents are pharmacologically active drugs, genetically active molecules, etc. Compounds of interest include, for example, chemotherapeutic agents, hormones or hormone antagonists, growth factors or recombinant growth factors and fragments and variants thereof. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The agents include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

Agents are screened for effect on the humanized vascularized heart tissue by administering at least one agent to a subject which is the in vivo humanized model of vascular disease. The change in parameters in response to the agent is measured, and the result evaluated by comparison to reference agents or absence of agent or other controls one of ordinary skill in the art would use.

Parameters of functional human vascularized cardiac tissue can be quantifiable components of humanized vascular heart tissue, particularly parameters that can be accurately measured, desirably in real time and/or in vivo when the humanized vascular heart tissue is still in a live animal which is the host for the in vivo humanized model of vascular disease as disclosed herein. In some embodiments, the human vascularized cardiac tissue present within the in vivo humanized model of vascular disease can be injected with a dye or visualizing agent, such by direct injection into the vascularization of the human cardiac tissue (e.g. into the vascular coronary tree) to see, for example, an increase or decrease of vascular blood flow or increase or decrease in angiogenesis to the human cardiac tissue in response to administration of an agent to the in vivo humanized model of vascular disease. The visualization can be performed by MRI or other visualization methods commonly known in the art in real-time without the need to sacrifice the in vivo humanized model of vascular disease. This methods of visualization can also be useful to determine if an agent promotes or inhibits the formation of different types of blood vessels, such as arteries versus veins, as well as promote or inhibit blood flow through arteries or veins.

In some embodiments, the ISL1+ primordial progenitors can be genetically modified to express markers, e.g. bioluminescence markers, such as luciferase and the like and other bioluminescent markers commonly known in the art for real-time imaging of the function, and/or growth of the humanized vascular heart tissue in vivo in real time. The is advantageous as it allows the continuous and/or time-point analysis of the effect of an agent on the human vascularized heart tissue in the same animal over a period of time, as well as allows one to compare the effect of multiple different agents (administered to the subject at different timepoints) in the same in vivo humanized model of vascular disease subject without sacrificing the in vivo humanized model of vascular disease.

In some embodiments, quantifiable parameters can include contractile force, contractibility, cardiomyocyte atrophy, altered contraction, frequency of contraction, contraction duration, contraction stamina, vascularization of the human three-dimensional vascularized cardiac tissue. In some embodiments, quantifiable parameters differentiation, survival and regeneration of the ISL1+ primordial progenitors within the human three-dimensional vascularized cardiac tissue.

While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

A plurality of in vivo humanized model of vascular disease assays may be run in parallel (e.g. different subjects comprising human vascularized cardiac tissue) with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Optionally, the human ISL+ primordial progenitor used in the screen can be manipulated to express desired gene products. Gene therapy can be used to either modify a cell to replace a gene product or add or knockdown a gene product. In some embodiments the genetic engineering is done to facilitate regeneration of tissue, to treat disease, or to improve survival of the cells following implantation into a subject. In some embodiments, the human ISL+ primordial progenitor is genetically modified to express a stress survival factor so the ISL+ primordial cells can survive contraction, e.g. such as expression of truncated Creb312 as disclosed in U.S. provisional application 61/145,208, filed on Jan. 16, 2009, which is incorporated herein by reference. In some embodiments, a population of human ISL+ primordial progenitor is genetically modified to express at least one gene which prevent rejection. Techniques for transfecting cells are known in the art.

A skilled artisan could envision a multitude of genes which would convey beneficial properties to the transfected human ISL+ primordial progenitor to be used in implantation (discussed in more detail below). The added gene may ultimately remain in the recipient human ISL+ primordial progenitor and all its progeny, or may only remain transiently, depending on the embodiment. For example, genes encoding angiogenic factors could be transfected into human ISL+ primordial progenitor then go to form human vascularized cardiac tissue as disclosed herein. Such genes would be useful for inducing collateral blood vessel formation as the cardiac smooth muscle tissue is regenerated. It some situations, it may be desirable to transfect the human ISL+ primordial progenitor with more than one gene.

In some instances, it is desirable to have the gene product secreted from the human ISL+ primordial progenitor. In such cases, the gene product preferably contains a secretory signal sequence that facilitates secretion of the protein. For example, if the desired gene product is an angiogenic protein, a skilled artisan could either select an angiogenic protein with a native signal sequence, e.g. VEGF, or can modify the gene product to contain such a sequence using routine genetic manipulation (See Nabel et al., 1993).

The desired gene can be transfected into the human ISL+ primordial progenitor using a variety of techniques. Preferably, the gene is transfected into the human ISL+ primordial progenitor using an expression vector. Suitable expression vectors include plasmid vectors (such as those available from Stratagene, Madison Wis.), viral vectors (such as replication defective retroviral vectors, herpes virus, adenovirus, adenovirus associated virus, and lentivirus), and non-viral vectors (such as liposomes or receptor ligands).

The desired gene is usually operably linked to its own promoter or to a foreign promoter which, in either case, mediates transcription of the gene product. Promoters are chosen based on their ability to drive expression in restricted or in general tissue types, for example in mesenchymal cells, or on the level of expression they promote, or how they respond to added chemicals, drugs or hormones. Other genetic regulatory sequences that alter expression of a gene may be co-transfected. In some embodiments, the host cell DNA may provide the promoter and/or additional regulatory sequences. Other elements that can enhance expression can also be included such as an enhancer or a system that results in high levels of expression.

Methods of targeting genes in mammalian cells are well known to those of skill in the art (U.S. Pat. Nos. 5,830,698; 5,789,215; 5,721,367 and 5,612,205). By "targeting genes" it is meant that the entire or a portion of a gene residing in the chromosome of a cell is replaced by a heterologous nucleotide fragment. The fragment may contain primarily the targeted gene sequence with specific mutations to the gene or may contain a second gene. The second gene may be operably linked to a promoter or may be dependent for transcription on a promoter contained within the genome of the cell. In a preferred embodiment, the second gene confers resistance to a compound that is toxic to cells lacking the gene. Such genes are typically referred to as antibiotic-resistance genes. Cells containing the gene may then be selected for by culturing the cells in the presence of the toxic compound.

Methods of gene targeting in mammals are commonly used to generate "knockout" or modified ES cells, which can be applied to human or marine ES cells (U.S. Pat. Nos. 5,616,491; 5,614,396, which are incorporated herein in their entirety by reference). These techniques take advantage of the ability of embryonic stem cells to promote homologous recombination, an event that is rare in differentiated mammalian cells. Recent advances in human embryonic stem cell culture may provide a needed component to applying the technology to human systems (Thomson; 1998). Furthermore, the methods of the present invention can be used to isolate and enrich for stem cells or progenitor cells that are capable of homologous recombination and, therefore, subject to gene targeting technology. Indeed, the ability to isolate and grow somatic stem cells and progenitor cells has been viewed as impeding progress in human gene targeting (Yanez & Porter, 1998).

Therapeutic Uses of Isl+ Primordial Heart Cells

Another embodiment relates to the therapeutic use of human primordial ISL1+ progenitors, for example, in one embodiment the invention provides methods for the treatment cardiovascular disorders and/or congenital heart disease in a subject comprising transplanting into subjects vascularized human heart tissue generated from human ISL1+ progenitors.

In another aspect of the invention, the methods provide use vascularized human cardiac tissue produced from the human ISL1+ progenitors by the methods as disclosed herein. In one embodiment, the vascularized human cardiac tissue can be used for the production of a pharmaceutical composition, for the use in transplantation into subjects in need of cardiac tissue transplantation, for example but not limited to subjects with congenital and/or acquired heart disease and/or subjects with vascular diseases. In one embodiment, human ISL1+ progenitors used to produced the vascularized human cardiac tissue can be genetically modified. In another aspect, the subject can have or be at risk of heart disease and/or vascular disease. In some embodiments, the human ISL1+ progenitors used to produced the vascularized human cardiac tissue can be autologous and/or allogenic. In some embodiments, the human ISL1+ progenitors used to produced the vascularized human cardiac tissue for transplanted are immunogenetically matched to the transplant receipt (e.g. blood type and HLA matched).

In some embodiments, a subject in which human ISL1+ progenitors are implanted for therapeutic purposes is a mammal, such as a human.

In one embodiment of the invention relates to a method of treating a circulatory disorder comprising administering an effective amount of a composition comprising human vascularized cardiac tissue as disclosed herein to a subject with a circulatory disorder. In a further embodiment, the invention provides a method for treating myocardial infarction, comprising administering a composition comprising human vascularized cardiac tissue to a subject having a myocardial infarction in an effective amount sufficient to produce human vascularized cardiac tissue in the heart of the individual.

The invention further provides for a method of treating an injured tissue in an individual comprising: (a) determining a site of tissue injury in the individual; and (b) administering human vascularized cardiac tissue of the invention in a composition into and around the site of tissue injury. In one embodiment, the tissue is human vascularized cardiac tissue. In one embodiment, the human vascularized cardiac tissue is produced from human ISL1+ primordial progenitors, isolated from ES cells or alternatively derived from an iPS cells, which are derived from an autologous source. In a further embodiment, the tissue injury is a myocardial infarction, cardiomyopathy or congenital heart disease In one embodiment of the above methods, the subject is a human and the composition is human vascularized cardiac tissue. In alternative embodiments, the human vascularized cardiac tissue can be use to treat circulatory disorder is selected from the group consisting of cardiomyopathy, myocardial infarction, and congenital heart disease. In some embodiments, the circulatory disorder is a myocardial infarction. The invention provides that the human vascularized cardiac tissue is used to treat myocardial infarction by reducing the size of the myocardial infarct. It is also contemplated that the cells from the human vascularized cardiac tissue treats myocardial infarction by reducing the size of the scar resulting from the myocardial infarct. The invention contemplates that human vascularized cardiac tissue is administered directly to heart tissue of a subject, or is administered systemically by any means known by one of ordinary skill in the art.

In some embodiments, the human vascularized heart tissue can be used as a "patch" or band aid at site of cardiac injury or cardiac dysfunction. In some embodiments, the vascularized heart tissue "patch" or band aid at site of myocardial infarction. In some embodiments, the human vascularized cardiac tissue can be applied as a patch to the heart. In some embodiment, the patch can be attached by any means, such as by a fixative, glue, sutures and staples and the like.

In certain embodiments, human vascularized cardiac tissue can be attached to at least one tissue e.g, heart or diaphragm at the time of implantation, using techniques known in the art. Exemplary attachment means include suturing, stapling, for example, with surgical staples, glue or adhesive, such as surgical glue, biochemical interactions such as with the extracellular matrix, photo-activated glue, fibrin glue, acrylate-based adhesives, and the like.

The present invention is also directed to a method of treating circulatory damage in the heart or peripheral vasculature which occurs as a consequence of genetic defect, physical injury, environmental insult or damage from a stroke, heart attack or cardiovascular disease (most often due to ischemia) in a subject, the method comprising administering (including implanting or transplanting) a human vascularized cardiac tissue to a subject. Medical indications for such treatment include treatment of acute and chronic heart conditions of various kinds, such as coronary heart disease, cardiomyopathy, endocarditis, congenital cardiovascular defects, and congestive heart failure. Efficacy of treatment can be monitored by clinically accepted criteria, such as reduction in area occupied by scar tissue or revascularization of scar tissue, and in the frequency and severity of angina; or an improvement in developed pressure, systolic pressure, end diastolic pressure, patient mobility, and quality of life.

In some embodiments, the human vascularized cardiac tissue is useful for the treatment of congenital cardiovascular abnormalities. In some embodiments, the recipient subjects is an adult, an in some embodiments, the recipient subject is a neonate or child such as a human baby or human child. In some embodiments, the human vascular tissue as disclosed herein and/or ISL1+ primordial cells can be implanted into a neonate, which has the advantage that it will grow into appropriate cardiovascular structures, e.g. valves, myocardium etc with the normal development of the neonate thorough childhood and into adulthood. This is advantage as current methodologies using cardiac tissue implants or grafts for treatment of neonates and young children with congenital cardiovascular defects do not grow and develop as the child develops, and thus such children or subjects with severe congenital defects need multiple surgeries to repair the heart, and often do not survive beyond 2 years of age.

In some embodiments, the effects of administration of human vascularized cardiac tissue would be demonstrated by, but not limited to, one of the following clinical measures: increased heart ejection fraction, decreased rate of heart failure, decreased infarct size, decreased associated morbidity (pulmonary edema, renal failure, arrhythmias) improved exercise tolerance or other quality of life measures, and decreased mortality. The effects of the administration of human vascularized cardiac tissue can be evident over the course of days to weeks after the procedure. However, beneficial effects may be observed as early as several hours after the procedure, and may persist for several years.

In some embodiments, the human vascularized cardiac tissue can be implanted as a patch for the diaphragm. This can be useful for treatment of diseases or disorders where diaphragm function is impaired, as well as diseases such as Duchene Muscular dystrophy. In some embodiments, the human vascularized cardiac tissue can be genetically modified to increase survival post implantation, for example express the mechanical stretch survival factor, such as Creb312 as disclosed herein, and/or express the normal dystrophin gene.

In some embodiments, the human vascularized cardiac tissue are administered to a subject in need thereof in a manner that permits the cells in the human vascularized cardiac tissue to graft and/or migrate to the intended tissue site and reconstitute or regenerate the functionally deficient area. Special devices are available that are adapted for administering the human vascularized cardiac tissue capable of reconstituting cardiac function directly to the chambers of the heart, the pericardium, or the interior of the cardiac muscle at the desired location. The human vascularized cardiac tissue may be administered to a recipient heart by intracoronary injection, e.g. into the coronary circulation. The human vascularized cardiac tissue may also be administered by intramuscular injection into the wall of the heart.

In some embodiments, the human vascularized cardiac tissue for treatment can comprise at least one type of additional cells, such as CVP cells as disclosed herein.

In some embodiments, the human vascularized cardiac tissue can be implanted into a subject in need thereof in the presence of growth factors, and/or angiogenic factors. In some embodiments, the ISL1+ primordial cells are genetically modified to express the growth factors and/or angiogenic factors as disclosed herein, under the control of constitutive, or tissue-specific or inducible promoters. Exemplary cytokines include angiogenin, vascular endothelial growth factor (VEGF, including, but not limited to VEGF-165), interleukins, fibroblast growth factors, for example, but not limited to, FGF-1 and FGF-2, hepatocyte growth factor, (HGF), endothelins (such as ET-1, ET-2, and ET-3), insulin-like growth factor (IGF-1), angiopoietins (such as Ang-1, Ang-2, Ang-3/4), angiopoietin-like proteins (such as ANGPTL1, ANGPTL-2, ANGPTL-3, and ANGPTL-4), platelet-derived growth factor (PDGF), including, but not limited to PDGF-AA, PDGF-BB and PDGF-AB, epidermal growth factor (EGF), endothelial cell growth factor (ECGF), including ECGS, platelet-derived endothelial cell growth factor (PD-ECGF), placenta growth factor (PLGF), and the like. The skilled artisan will understand that the choice of chemokines and cytokine fragments to be expressed by human ISL1+ primordial progenitors, or administered with the human vascularized cardiac tissue will, in part, on the target tissue or organ to be implanted with the human vascularized cardiac tissue.

The compositions comprising human vascularized cardiac tissue can have a variety of uses in clinical therapy, research, development, and commercial purposes. For therapeutic purposes, for example, human vascularized cardiac tissue may be administered to enhance tissue maintenance or repair of cardiac muscle for any perceived need, such as an inborn en⁻or in metabolic function, the effect of a disease condition, or the result of significant trauma. The human vascularized cardiac tissue that are administered to the subject not only help restore function to damaged or otherwise unhealthy tissues, but also facilitate remodeling of the damaged tissues.

To determine the suitability of human vascularized cardiac tissue for therapeutic administration, the human vascularized cardiac tissue can first be tested in a suitable animal model, such as the in vivo humanized model of cardiovascular disease as disclosed herein. At one level, human vascularized cardiac tissue is assessed for its ability to survive and maintain function in vivo.

The human vascularized cardiac tissue can be administered in any physiologically acceptable excipient. The human vascularized cardiac tissue may be introduced by injection, catheter, or the like. In some embodiments, the human vascularized cardiac tissue can be cryopreserved (e.g. frozen) at liquid nitrogen temperatures and stored for long periods of time, being capable of use on thawing. If frozen, the cells will usually be stored in a 10% DMSO, 50% FCS, 40% RPMI 1640 medium. Once thawed, the human vascularized cardiac tissue can be cultured ex vivo in the presence of growth factors and/or feeder layers for an appropriate period of time prior to implanting into a subject in need thereof.

The human vascularized cardiac tissue as disclosed herein can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition will be adapted in accordance with the route and device used for administration. The composition comprising human vascularized cardiac tissue may also comprise or be accompanied with one or more other ingredients that facilitate the engraftment or functional mobilization of the cells. Suitable ingredients include matrix proteins that support or promote adhesion of the cells, or complementary cell types, especially endothelial cells. In another embodiment, the composition may comprise resorbable or biodegradable matrix scaffolds.

As discussed herein, in some embodiments, the human vascularized cardiac tissue can be generated from human ISL1+ primordial progenitors which are genetically altered in order to introduce genes useful in the human vascularized cardiac tissue, e.g. repair of a genetic defect in an individual, selectable marker, etc., or genes useful in selection against cells which are not ISL1+ primordial cells. As discussed, the human vascularized cardiac tissue can be generated from human ISL1+ primordial progenitors which are genetically modified to enhance survival, control proliferation, and the like. Human ISL1+ primordial progenitors may be genetically altering by transfection or transduction with a suitable vector, homologous recombination, or other appropriate technique, so that they express a gene of interest. In one embodiment, the human vascularized cardiac tissue can be generated from human ISL1+ primordial progenitors which are transfected with genes encoding a telomerase catalytic component (TERT), typically under a heterologous promoter that increases telomerase expression beyond what occurs under the endogenous promoter, (see International Patent Application WO 98/14592). In other embodiments, a selectable marker is introduced, to provide for greater purity of the desired differentiating cell. In some embodiments, the human vascularized cardiac tissue can be generated from human ISL1+ primordial progenitors which are genetically altered using vector containing supernatants over a 8-16 h period, and then exchanged into growth medium for 1-2 days. Genetically altered ISL1+ primordial progenitors can be selected using a drug selection agent such as puromycin, G418, or blasticidin, and then recultured.

Gene therapy can be used to either modify a cell to replace a gene product, to facilitate regeneration of tissue, to treat disease, or to improve survival of the cells following implantation into a subject (i.e. prevent rejection).

In an alternative embodiment, the human vascularized cardiac tissue can be generated from human ISL1+ primordial progenitors which are also be genetically altered in order to enhance their ability to be involved in tissue regeneration, or to deliver a therapeutic gene to a site of administration. A vector is designed using the known encoding sequence for the desired gene, operatively linked to a promoter that is either pan-specific or specifically active in the differentiated cell type. Of particular interest are human ISL1+ primordial progenitors that are genetically altered to express one or more growth factors of various types, cardiotropic factors such as atrial natriuretic factor, cripto, and angiogenic factors such as VEGF.

Many vectors useful for transferring exogenous genes into target human ISL1+ primordial progenitors are available. The vectors may be episomal, e.g. plasmids, virus derived vectors such as cytomegalovirus, adenovirus, etc., or may be integrated into the target cell genome, through homologous recombination or random integration, e.g. retrovirus derived vectors such MMLV, HIV-1, ALV, etc. For modification of stem cells, lentiviral vectors are preferred. Lentiviral vectors such as those based on HIV or FIV gag sequences can be used to transfect non-dividing cells, such as the resting phase of human stem cells (see Uchida et al. (1998) P.N.A.S. 95(20): 11939-44). In some embodiments, combinations of retroviruses and an appropriate packaging cell line may also find use, where the capsid proteins will be functional for infecting the target cells. Usually, the cells and virus will be incubated for at least about 24 hours in the culture medium. The cells are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line.

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) Mol. Cell. Biol. 5:431-437); PA317 (Miller et al. (1986) Mol. Cell. Biol. 6:2895-2902) GRIP (Danos et al. (1988) PNAS 85:6460-6464). Retroviruses packaged with xenotropic envelope protein, e.g. AKR env, are capable of infecting most mammalian cell types, except murine cells. In some embodiments, the vectors may include genes that must later be removed, e.g. using a recombinase system such as Cre/Lox, or the cells that express them destroyed, e.g. by including genes that allow selective toxicity such as herpesvirus TK, Bcl-Xs, etc.

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in different cell types.

In one aspect of the present invention, the human vascularized cardiac tissue generated from human ISL1+ primordial progenitors can be administered systemically or to a target anatomical site. The human vascularized cardiac tissue generated from human ISL1+ primordial progenitors can be grafted into or nearby a subject's heart, for example, or may be administered systemically, such as, but not limited to, intra-arterial or intravenous administration.

In alternative embodiments, the human vascularized cardiac tissue generated from human ISL1+ primordial progenitors as disclosed herein can be administered in various ways as would be appropriate to implant in the cardiovascular system, including but not limited to parenteral, including intravenous and intraarterial administration, intrathecal administration, intraventricular administration, intraparenchymal, intracranial, intracisternal, intrastriatal, and intranigral administration. Optionally, the human vascularized cardiac tissue generated from human ISL1+ primordial progenitors are administered in conjunction with an immunosuppressive agent.

In some embodiments, the human vascularized cardiac tissue generated from human ISL1+ primordial progenitors as disclosed herein can be administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement, including but not limited to improved survival rate or more rapid recovery, or improvement or elimination of symptoms and other indicators as are selected as appropriate measures by those skilled in the art. Implantation of the human vascularized cardiac tissue generated from human ISL1+ primordial progenitors as disclosed herein into a recipient subject can take place but is not limited to the following locations: clinic, clinical office, emergency department, hospital ward, intensive care unit, operating room, catheterization suites, and radiologic suites.

In other embodiments, at least a portion of the human vascularized cardiac tissue generated from human ISL1+ primordial progenitors, and/or a population of human ISL1+ primordial progenitors as disclosed herein can be stored for later implantation/infusion. In some embodiments, the human vascularized cardiac tissue, and/or human ISL1+ primordial progenitors as disclosed herein can be divided into more than one aliquot or unit such that part of the human vascularized cardiac tissue is retained for later application while part is applied immediately to the subject. Moderate to long-term storage of all or part of the human vascularized cardiac tissue, and/or human ISL1+ primordial progenitors as disclosed can be stored in a cell bank, and is also within the scope of this invention, as disclosed in U.S. Patent Application Serial No. 20030054331 and Patent Application No. WO03024215, and is incorporated by reference in their entireties. At the end of processing, the human vascularized cardiac tissue as disclosed herein may be loaded into a delivery device, such as a syringe, for placement into the recipient subject by any means known to one of ordinary skill in the art.

Pharmaceutical Composition:

In some embodiments, the present invention relates to a composition comprising the human vascularized cardiac tissue generated from human ISL1+ primordial progenitors as disclosed herein. In some embodiments, the present invention relates to a composition comprising a population of human ISL1+ primordial progenitors as disclosed herein. In some embodiments, all compositions can further comprise a ISL1+ primordial progenitors differentiation agent. ISL1+ primordial progenitor differentiation agents for use in the present invention are well known to those of ordinary skill in the art. Examples of such agents include, but are not limited to, cardiotrophic agents, creatine, carnitine, taurine, cardiotropic factors as disclosed in U.S. Patent Application Serial No. 2003/0022367 which is incorporated herein by reference, TGF-beta ligands, such as activin A, activin B, insulin-like growth factors, bone morphogenic proteins, fibroblast growth factors, platelet-derived growth factor natriuretic factors, insulin, leukemia inhibitory factor (LIF), epidermal growth factor (EGF), TGFalpha, and products of the BMP or cripto pathway. The pharmaceutical compositions may further comprise a pharmaceutically acceptable carrier.

The human vascularized cardiac tissue composition or human ISL1+ primordial progenitor composition can be administered to a subject alone or in combination with other cells, tissue, tissue fragments, growth factors such as VEGF, or VEGF homologues, e.g., $VEGF_{165}$ or $TGF\beta$ inhibitors such as ALK5i as disclosed herein. In some embodiments, the Isl1+ primordial progenitors are administered to a subject in an admixture with VEGF and/or a $TGF\beta$ inhibitor, e.g., ALK5i as disclosed herein, at the concentrations disclosed herein. In alternative embodiments, other known angiogenic or arteriogenic growth factors can be administered in combination with the Isl1 primordial progenitors, e.g., biologically active or inert compounds, resorbable plastic scaffolds, or other additive intended to enhance the delivery, efficacy, tolerability, vascularization, or function of the implanted Isl1+ progenitor cell population.

In some embodiments, the human vascularized cardiac tissue composition or human ISL1+ primordial progenitor composition can also be modified by insertion of DNA or by placement in cell culture in such a way as to change, enhance, or supplement the function of the cells for derivation of a structural or therapeutic purpose. For example, gene transfer techniques for stem cells are known by persons of ordinary skill in the art, as disclosed in (Morizono et al., 2003; Mosca et al., 2000), and may include viral transfection techniques, and more specifically, adeno-associated virus gene transfer techniques, as disclosed in (Walther and Stein, 2000) and (Athanasopoulos et al., 2000). Non-viral based techniques may also be performed as disclosed in (Murarnatsu et al., 1998).

In another aspect, the human vascularized cardiac tissue composition or human ISL1+ primordial progenitor composition can be combined with a gene encoding pro-angiogenic and/or cardiomyogenic growth factor(s) which would allow the human vascularized cardiac tissue composition or human ISL1+ primordial progenitor composition to act as their own source of growth factor during cardiac repair or regeneration. Genes encoding anti-apoptotic factors or agents could also be applied. Addition of the gene (or combination of genes) could be by any technology known in the art including but not limited to adenoviral transduction, "gene guns," liposome-mediated transduction, and retrovirus or lentivirus-mediated transduction, plasmid' adeno-associated virus.

In some embodiments, human vascularized cardiac tissue composition or human ISL1+ primordial progenitor composition can be implanted into a subject along with a carrier material bearing gene delivery vehicle capable of releasing and/or presenting genes to the cells over time such that transduction can continue or be initiated.

In some embodiments, particularly when the human vascularized cardiac tissue or human ISL1+ primordial progenitors are administered to a subject other than the subject from whom the ISL1+ primordial progenitors were obtained, one or more immunosuppressive agents may be administered to the subject receiving the human vascularized cardiac tissue composition or human ISL1+ primordial progenitor composition to reduce, and preferably prevent, rejection of the transplant. As used herein, the term "immunosuppressive drug or agent" is intended to include pharmaceutical agents which inhibit or interfere with normal immune function. Examples of immunosuppressive agents suitable with the methods disclosed herein include agents that inhibit T-cell/B-cell costimulation pathways, such as agents that interfere with the coupling of T-cells and B-cells via the CTLA4 and B7 pathways, as disclosed in U.S. Patent Pub. No 2002/0182211. In one embodiment, a immunosuppressive agent is cyclosporine A. Other examples include myophenylate mofetil, rapamicin, and anti-thymocyte globulin. In one embodiment, the immunosuppressive drug is administered with at least one other therapeutic agent. The immunosuppressive drug is administered in a formulation which is compatible with the route of administration and is administered to a subject at a dosage sufficient to achieve the desired therapeutic effect. In another embodiment, the immunosuppressive drug is administered transiently for a sufficient time to induce tolerance to the cardiovascular stem cells of the invention.

In certain embodiments of the invention, the human vascularized cardiac tissue or human ISL1+ primordial progenitors can be administered to a patient with one or more cellular differentiation agents, such as cytokines and growth factors, as disclosed herein. In some embodiments, the human vascularized cardiac tissue or human ISL1+ primordial progenitors can be administered to a patient with one or more of VEGF or a homologue thereof, or a TGFβ inhibitor, e.g., a ALK5 inhibitor, e.g., SB-431542 as disclosed herein. These differentiation factors, as well as other differentiation agents can also be administered concurrently or sequentially (prior to or post) administration of the Isl1+ primordial progenitors to the subject. Examples of the various other cell differentiation agents are disclosed in U.S. Patent Application Serial No. 2003/0022367 which is incorporated herein by reference, or Gimble et al., 1995; Lennon et al., 1995; Majumdar et al., 1998; Caplan and Goldberg, 1999; Ohgushi and Caplan, 1999; Pittenger et al., 1999; Caplan and Bruder, 2001; Fukuda, 2001; Worster et al., 2001; Zuk et al., 2001. Other examples of cellular differentiation agents, cytokines and growth factors which can be administered in combination, concurrent with, or sequentially with administration of the Isl1+ primordial progenitors include, but are not limited to, cardiotrophic agents, creatine, carnitine, taurine, TGF-beta ligands, such as activin A, activin B, insulin-like growth factors, bone morphogenic proteins, fibroblast growth factors, platelet-derived growth factor natriuretic factors, insulin, leukemia inhibitory factor (LIF), epidermal growth factor (EGF), TGFalpha, and products of the BMP or cripto pathway.

In some embodiments, a human vascularized cardiac tissue composition or human ISL1+ primordial progenitor composition can comprise an effective number of cells, optionally, in combination with a pharmaceutically acceptable carrier, additive or excipient. In certain aspects of the present invention, a human vascularized cardiac tissue composition or human ISL1+ primordial progenitor composition can be are administered to the subject in need of a transplant in sterile saline. In other aspects of the present invention, the human vascularized cardiac tissue composition or human ISL1+ primordial progenitor composition can be administered in Hanks Balanced Salt Solution (HBSS) or Isolyte S, pH 7.4. Other approaches may also be used, including the use of serum free cellular media. In one embodiment, a human vascularized cardiac tissue composition or human ISL1+ primordial progenitor composition can be administered in plasma or fetal bovine serum, and DMSO. Systemic administration of the human vascularized cardiac tissue composition or human ISL1+ primordial progenitor composition to the subject may be preferred in certain indications, whereas direct administration at the site of or in proximity to the diseased and/or damaged tissue may be preferred in other indications.

In some embodiments, a human vascularized cardiac tissue composition generated from human ISL1+ primordial progenitors, and/or a population of human ISL1+ primordial progenitors can optionally be packaged in a suitable container, in the presence of a suitable media. In some embodiments, the kit can optionally further comprise a volume of conditioned media comprising VEGF, and/or a TGFβ inhibitor, e.g, ALK5 inhibitor as disclosed herein, for culturing the Isl1+ primordial progenitors to induce their differentiation along vasculargenic lineages to Isl1+/CD31+ cells. In some embodiments, the VEGF, and/or a TGFβ inhibitor, e.g, ALK5 inhibitor are not present in the culture media, but are packaged separately in the kit to be added to the culture media and/or contacted with to the Isl1+ primordial progenitors as desired by the kit user. In some embodiments, the package further comprises written instructions for a desired purpose, such as methods of implantation into a subject (and optionally methods of storage and/or methods of thawing if cryopreserved) of the human vascularized cardiac tissue composition or human ISL1+ primordial progenitor composition can for the improvement of an abnormality of cardiac function or the treatment of cardiovascular disease. In some embodiments, treatment can refer to a reduction of a cardiovascular disorder. In alternative embodiments, treatment is prophylactic treatment to prevent the development of a cardiac disorder where the subject is at risk of developing a cardiovascular disorder as disclosed herein.

In one embodiment, the human vascularized cardiac tissue composition or human ISL1+ primordial progenitor composition can be administered with a differentiation agent. In one embodiment, the human vascularized cardiac tissue composition or human ISL1+ primordial progenitor composition can be combined with the differentiation agent and administered (e.g. implanted) concurrently to the subject. In another embodiment, the human vascularized cardiac tissue composition or human ISL1+ primordial progenitor composition are administered separately to the subject from the differentiation agent. Optionally, if the human vascularized cardiac tissue composition or human ISL1+ primordial progenitor composition are administered separately from the differentiation agent, there is a temporal separation in the administration of the human vascularized cardiac tissue composition or human ISL1+ primordial progenitor composition and the differentiation agent. The temporal separation may range from about less than a minute in time, to about hours or days in time. The determination of the optimal timing and order of administration is readily and routinely determined by one of ordinary skill in the art.

Uses of Human ISL1+ Primordial Progenitors as Assays.

In one embodiment of the invention, the human ISL1+ primordial progenitors as disclosed herein can be used as an assay for the study and understanding of signaling pathways of human ISL1+ primordial progenitors growth, proliferation and differentiation. The use of the human ISL1+ primordial progenitors as disclosed herein is useful to aid the development of therapeutic applications for congenital and adult heart failure. The use of such human ISL1+ primordial progenitors as disclosed herein enable the study of specific cardiac lineages, in particular cardiac structures without the need and complexity of time consuming animal models. In another embodiment, the human ISL1+ primordial progenitors as disclosed herein can be genetically modified to carry specific disease and/or pathological traits and phenotypes of cardiac disease and adult heart failure.

In one embodiment, the assay comprises a plurality of ISL1+ primordial progenitors as disclosed herein, or their differentiated progeny. In one embodiment, the assay comprises cells derived from the ISL1+ primordial progenitors of the invention. In one embodiment, the assay can be used for the study of differentiation pathways of human ISL1+ primordial progenitors as disclosed herein, for example but not limited to the differentiation along the cardiomyocyte lineage, smooth muscle lineage, endothelial lineage, and subpopulations of these lineages. In one embodiment, the study of subpopulations can be, for example, study of subpopulations of cardiomyocytes, for example artial cardiomyocytes, ventricular cardiomyocytes, outflow tract cardiomyocytes, conduction system cardiomyocytes.

In another embodiment, the assay can be used to study the ISL1+ primordial progenitors which comprise a pathological characteristic, for example, a disease and/or genetic characteristic associated with a disease or disorder. In some embodiments, the disease of disorder is a cardiovascular disorder or disease. In some embodiments, the ISL1+ primordial progenitor has been genetically engineered to comprise the characteristic associated with a disease or disorder. Such methods to genetically engineer the ISL1+ primordial progenitor are well known by those in the art, and include introducing nucleic acids into the cell by means of transfection, for example but not limited to use of viral vectors or by other means known in the art.

In some embodiments, the ISL1+ primordial progenitor of the present invention can be easily manipulated in experimental systems that offer the advantages of targeted lineage differentiation as well as clonal homogeneity and the ability to manipulate external environments. Furthermore, due to ethical unacceptability of experimentally altering a human germ line, the ES cell transgenic route is not available for experiments that involve the manipulation of human genes. Gene targeting in human cardiovascular stem cells of the present invention allows important applications in areas where rodent model systems do not adequately recapitulate human biology or disease processes.

In another embodiment, the ISL1+ primordial progenitor of this invention can be used to prepare a cDNA library relatively uncontaminated with cDNA that is preferentially expressed in cells from other lineages. For example, cardiovascular stem cells are collected and then mRNA is prepared from the pellet by standard techniques (Sambrook et al., supra). After reverse transcribing into cDNA, the preparation can be subtracted with cDNA from other undifferentiated ES cells, other progenitor cells, or end-stage cells from the cardiomyocyte or any other developmental pathway, for example, in a subtraction cDNA library procedure.

The ISL1+ primordial progenitors of this invention can also be used to prepare antibodies that are specific for markers of ISL1+ primordial progenitors. Polyclonal antibodies can be prepared by injecting a vertebrate animal with cells of this invention in an immunogenic form. Production of monoclonal antibodies is described in such standard references as U.S. Pat. Nos. 4,491,632, 4,472,500 and 4,444,887, and Methods in Enzymology 73B:3 (1981). Specific antibody molecules can also be produced by contacting a library of immunocompetent cells or viral particles with the target antigen, and growing out positively selected clones. See Marks et al., New Eng. J. Med. 335:730, 1996, and McGuiness et al., Nature Biotechnol. 14:1449, 1996. A further alternative is reassembly of random DNA fragments into antibody encoding regions, as described in EP patent application 1,094,108 A.

The antibodies in turn can be used to identify or rescue (for example restore the phenotype) cells of a desired phenotype from a mixed cell population, for purposes such as costaining during immunodiagnosis using tissue samples, and isolating precursor cells from terminally differentiated cardiomyocytes and cells of other lineages. Of particular interest is the examination of the gene expression profile during and following differentiation of the cardiovascular stem cells of the invention. The expressed set of genes may be compared against other subsets of cells, against ES cells, against adult heart tissue, and the like, as known in the art. Any suitable qualitative or quantitative methods known in the art for detecting specific mRNAs can be used. mRNA can be detected by, for example, hybridization to a microarray, in situ hybridization in tissue sections, by reverse transcriptase-PCR, or in Northern blots containing poly A+ mRNA. One of skill in the art can readily use these methods to determine differences in the molecular size or amount of mRNA transcripts between two samples.

Any suitable method for detecting and comparing mRNA expression levels in a sample can be used in connection with the methods of the invention. For example, mRNA expression levels in a sample can be determined by generation of a library of expressed sequence tags (ESTs) from a sample. Enumeration of the relative representation of ESTs within the library can be used to approximate the relative representation of a gene transcript within the starting sample. The results of EST analysis of a test sample can then be compared to EST analysis of a reference sample to determine the relative expression levels of a selected polynucleotide, particularly a polynucleotide corresponding to one or more of the differentially expressed genes described herein.

Alternatively, gene expression in a test sample can be performed using serial analysis of gene expression (SAGE) methodology (Velculescu et al., Science (1995) 270:484). In short, SAGE involves the isolation of short unique sequence tags from a specific location within each transcript. The sequence tags are concatenated, cloned, and sequenced. The frequency of particular transcripts within the starting sample is reflected by the number of times the associated sequence tag is encountered with the sequence population.

Gene expression in a test sample can also be analyzed using differential display (DD) methodology. In DD, fragments defined by specific sequence delimiters (e.g., restriction enzyme sites) are used as unique identifiers of genes, coupled with information about fragment length or fragment location within the expressed gene. The relative representation of an expressed gene with a sample can then be estimated based on the relative representation of the fragment associated with that gene within the pool of all possible fragments. Methods and compositions for carrying out DD are well known in the art, see, e.g., U.S. Pat. No. 5,776,683; and U.S. Pat. No. 5,807,680. Alternatively, gene expression in a sample using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry). One exemplary use of arrays in the diagnostic methods of the invention is described below in more detail.

Hybridization to arrays may be performed, where the arrays can be produced according to any suitable methods known in the art. For example, methods of producing large arrays of oligonucleotides are described in U.S. Pat. No. 5,134,854, and U.S. Pat. No. 5,445,934 using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in PCT published application no. WO 95/35505. Methods for collection of data from hybridization of samples with an array are also well known in the art. For example, the polynucleotides of the cell samples can be generated using a detectable fluorescent label, and hybridization of the polynucleotides in the samples detected by scanning the microarrays for the presence of the detectable label. Methods and devices for detecting fluorescently marked targets on devices are known in the art. Generally, such detection devices include a microscope and light source for directing light at a substrate. A photon counter detects fluorescence from the substrate, while an x-y translation stage varies the location of the substrate. A confocal detection device that can be used in the subject methods is described in U.S. Pat. No. 5,631,734. A scanning laser microscope is described in Shalon et al., Genome Res. (1996) 6:639. A scan, using the appropriate excitation line, is performed for each fluorophore used. The digital images generated from the scan are then combined for subsequent analysis. For any particular array element, the ratio of the fluorescent signal from one sample is compared to the fluorescent signal from another sample, and the relative signal intensity determined. Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e. data deviating from a predetermined statistical distribution, and calculating the relative binding affinity of the targets from the remaining data. The resulting data can be displayed as an image with the intensity in each region varying according to the binding affinity between targets and probes. Pattern matching can be performed manually, or can be performed using a computer program. Methods for preparation of substrate matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800,992. General methods in molecular and cellular biochemistry can also be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The following written description provides exemplary methodology and guidance for carrying out many of the varying aspects of the present invention.

Molecular Biology Techniques: Standard molecular biology techniques known in the art and not specifically described are generally followed as in Sambrook et al., Molecular Cloning: A Laboratory Manual, Cold Springs Harbor Laboratory, N.Y. (1989, 1992), and in Ausubel et al., Current Protocols in Molecular Biology, John Wiley and Sons, Baltimore, Md. (1989). Polymerase chain reaction (PCR) is carried out generally as in PCR Protocols: A Guide to Methods and Applications, Academic Press, San Diego, Calif. (1990). Reactions and manipulations involving other nucleic acid techniques, unless stated otherwise, are performed as generally described in Sambrook et al., Molecular Cloning: A Laboratory Manual, Cold Springs Harbor Laboratory Press, and methodology as set forth in U.S. Pat. Nos. 4,666,828; 4,683,202; 4,801,531; 5,192,659; and 5,272,057 and incorporated herein by reference. In situ PCR in combination with Flow Cytometry can be used for detection of cells containing specific DNA and mRNA sequences (see, for example, Testoni et al., Blood, 1996, 87:3822).

Immunoassays: Standard methods in immunology known in the art and not specifically described are generally followed as in Stites et al. (Eds.), Basic And Clinical Immunology, 8th Ed., Appleton & Lange, Norwalk, Conn. (1994); and Mishell and Shigi (Eds.), Selected Methods in Cellular Immunology, W. H. Freeman and Co., New York (1980).

In general, immunoassays are employed to assess a specimen such as for cell surface markers or the like. Immunocytochemical assays are well known to those skilled in the art. Both polyclonal and monoclonal antibodies can be used in the assays. Where appropriate other immunoassays, such as enzyme-linked immunosorbent assays (ELISAs) and radioimmunoassays (RIA), can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771; and 5,281,521 as well as Sambrook et al., Molecular Cloning: A Laboratory Manual, Cold Springs Harbor, N.Y., 1989. Numerous other references also may be relied on for these teachings.

Further elaboration of various methods that can be utilized for quantifying the presence of the desired marker include measuring the amount of a molecule that is present. A convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein (GFP) chimeras inside cells (for a review see Jones et al. (1999) Trends Biotechnol. 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999)

Biotechniques 26(1):112-225; Kawamoto et al. (1999) Genome Res 9(12):1305-12; and Chen et al. (1998) Genomics 51(3):313-24, for examples.

Antibody Production: Antibodies may be monoclonal, polyclonal, or recombinant. Conveniently, the antibodies may be prepared against the immunogen or immunogenic portion thereof, for example, a synthetic peptide based on the sequence, or prepared recombinantly by cloning techniques or the natural gene product and/or portions thereof may be isolated and used as the immunogen Immunogens can be used to produce antibodies by standard antibody production technology well known to those skilled in the art as described generally in Harlow and Lane, Antibodies: A Laboratory Manual, Cold Spring Harbor Laboratory, Cold Springs Harbor, N.Y. (1988) and Borrebaeck, Antibody Engineering-A Practical Guide by W. H. Freeman and Co. (1992). Antibody fragments may also be prepared from the antibodies and include Fab and F(ab')2 by methods known to those skilled in the art. For producing polyclonal antibodies a host, such as a rabbit or goat, is immunized with the immunogen or immunogenic fragment, generally with an adjuvant and, if necessary, coupled to a carrier; antibodies to the immunogen are collected from the serum. Further, the polyclonal antibody can be absorbed such that it is monospecific. That is, the serum can be exposed to related immunogens so that cross-reactive antibodies are removed from the serum rendering it monospecific.

For producing monoclonal antibodies, an appropriate donor is hyperimmunized with the immunogen, generally a mouse, and splenic antibody-producing cells are isolated. These cells are fused to immortal cells, such as myeloma cells, to provide a fused cell hybrid that is immortal and secretes the required antibody. The cells are then cultured, and the monoclonal antibodies harvested from the culture media.

For producing recombinant antibodies, messenger RNA from antibody-producing B-lymphocytes of animals or hybridoma is reverse-transcribed to obtain complementary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system. Antibody cDNA can also be obtained by screening pertinent expression libraries. The antibody can be bound to a solid support substrate or conjugated with a detectable moiety or be both bound and conjugated as is well known in the art. (For a general discussion of conjugation of fluorescent or enzymatic moieties see Johnstone & Thorpe, Immunochemistry in Practice, Blackwell Scientific Publications, Oxford, 1982). The binding of antibodies to a solid support substrate is also well known in the art. (see for a general discussion Harlow & Lane, Antibodies: A Laboratory Manual, Cold Spring Harbor Laboratory Publications, New York, 1988 and Borrebaeck, Antibody Engineering—A Practical Guide, W. H. Freeman and Co., 1992). The detectable moieties contemplated with the present invention can include, but are not limited to, fluorescent, metallic, enzymatic and radioactive markers. Examples include biotin, gold, ferritin, alkaline phosphates, galactosidase, peroxidase, urease, fluorescein, rhodamine, tritium, 14C, iodination and green fluorescent protein.

Gene therapy and genetic engineering of cardiovascular stem cells and/or mesenchymal cells: Gene therapy as used herein refers to the transfer of genetic material (e.g., DNA or RNA) of interest into a host to treat or prevent a genetic or acquired disease or condition. The genetic material of interest encodes a product (e.g., a protein, polypeptide, and peptide, functional RNA, antisense, RNA, microRNA, siRNA, shRNA, PNA, pcPNA) whose in vivo production is desired. For example, the genetic material of interest encodes a hormone, receptor, enzyme polypeptide or peptide of therapeutic value. Alternatively, the genetic material of interest encodes a suicide gene. For a review see "Gene Therapy" in Advances in Pharmacology, Academic Press, San Diego, Calif., 1997.

With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998). With respect to the culture of heart cells, standard references include The Heart Cell in Culture (A. Pinson ed., CRC Press 1987), Isolated Adult Cardiomyocytes (Vols. I & II, *Piper* & Isenberg eds, CRC Press 1989), Heart Development (Harvey & Rosenthal, Academic Press 1998).

The present invention is further illustrated by the following examples which in no way should be construed as being further limiting, The contents of all cited references, including literature references, issued patents, published patent applications, and co-pending patent applications, cited throughout this application are hereby expressly incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

In some embodiments of the present invention may be defined in any of the following numbered paragraphs:

1. A method for enhancing the differentiation of a Isl1+ primordial progenitor cells into Isl1+/CD31+ vasculargenic cells comprising contacting a population of Isl1+ primordial progenitors with at least one of VEGF or TGFβ inhibitor.

2. The method of paragraph 1, wherein the Isl1+ primordial progenitor is a human Isl1+ primordial progenitor.

3. The method of paragraph 2, wherein the human ISL1+ progenitors are negative for the expression of Nkx2.5 and/or KDR.

4. The method of paragraph 2, wherein the population of human ISL1+ progenitors are derived from human ES cells.

5. The method of paragraph 2, wherein the population of human ISL1+ progenitors are derived from human ES cell lines or from iPS cells.

6. The method of paragraph 2, wherein the population of human ISL1+ progenitors are genetically modified human ISL1+ progenitors.

7. The method of paragraph 1, wherein the VEGF is VEGF165.

8. The method of paragraph 1, wherein the VEGF is selected from the group consisting of: VEGF165, VEGF A, VEGF B, VEGF C, VEGF D, VEGF E, and VEGF F.

9. The method of paragraph 1, wherein the TGFβ inhibitor is an ALK5 inhibitor.

10. The method of paragraph 9, wherein the ALK5 inhibitor is SB431542 or A-83-01.

11. The method of any of paragraphs 1 to 10, wherein the population Isl1+ primordial progenitors are contacted with at least one additional growth factor, selected from any of the group consisting of: FGF, PDGFβ, ECGF, angiopoientin like proteins, IGF-1, HGF, PLDF, Interleukins and variants thereof.

12. The method of any of paragraphs 1 to 11, wherein the population Isl1+ primordial progenitors are contacted with VEGF or a TGFβ inhibitor or both for least 2 days.

13. The method of any of paragraphs 1 to 11, wherein the population Isl1+ primordial progenitors are contacted with VEGF or a TGFβ inhibitor or both for least 5 days.

14. The method of any of paragraphs 1 to 13, wherein the VEGF is used at a concentration of between 25-50 ng/ml.

15. The method of any of paragraphs 1 to 13, wherein the VEGF is used at a concentration of between 2-25 ng/ml.

16. The method of any of paragraphs 1 to 13, wherein the ALK5 inhibitor is used at a concentration of between 25-50 ng/ml.

17. The method of any of paragraphs 1 to 13, wherein the ALK5 inhibitor is used at a concentration of between 2-25 ng/ml.

18. A method for generating human three-dimensional vascular cardiac tissue, the method comprising implanting a population of human ISL1+ primordial cardiovascular progenitors into a subject, wherein the human ISL1+ primordial cardiovascular progenitors undergo coordinated differentiation into cardiomyocytes, endothelial cells, and smooth muscle cells to generate human three-dimensional vascularized cardiac tissue.

19. The method of paragraph 18, wherein the human ISL1+ progenitors are negative for the expression of Nkx2.5 and/or KDR.

20. The method of paragraph 18, wherein the population of human ISL1+ progenitors are derived from human ES cells.

21. The method of paragraph 18, wherein the population of human ISL1+ progenitors are derived from human ES cell lines or from iPS cells.

22. The method of paragraph 18, wherein the population of human ISL1+ progenitors have been contacted with VEGF or a TGFβ inhibitor or both prior to implanting into the subject.

23. The method of paragraph 22, wherein the population of human ISL1+ progenitors comprise a proportion of Isl1+/CD31+ cells.

24. The method of paragraph 23, wherein at least about 0.02% the population of human ISL1+ progenitors comprise proportion of Isl1+/CD31+ cells.

25. The method of paragraph 24, wherein at least about 0.05% or more of the population of human ISL1+ progenitors comprise proportion of Isl1+/CD31+ cells.

26. The method of paragraph 18, wherein the population of human ISL1+ progenitors are genetically modified human ISL1+ progenitors.

27. The method of paragraph 18, wherein the population of human ISL1+ progenitors are implanted into the kidney capsule of the subject.

28. The method of paragraph 18, wherein the population of human ISL1+ progenitors are implanted into the subject in one or more of the following locations in the subject; kidney capsule, peritoneal cavity, liver, ascites, pericardium, epicardium, pericardial space, heart, on the surface of the heart, subcutaneous space.

29. The method of paragraph 18, wherein the population of human Isl1+ progenitors is implanted in a bioreactor or capsule.

30. The method of paragraph 18, wherein the population of human ISl1+ progenitors comprises at least one additional cell type.

31. The method of paragraph 30, wherein the additional cell type is committed ventricular progenitors (CVPs), wherein the CVP express at least two of the following markers; Mef2c, Nkx2.5, Tbx20, Isl1, GATA4, GATA6, Tropinin T, Tropinin C 32. The method of paragraph 30, wherein the additional cell type is a committed vasculargenic Isl1+/CD31+ progenitor (CVPs).

33. The method of any of paragraphs 18 to 32, wherein the human ISl1+ progenitors are seeded onto a three-dimensional matrix prior to implanting into the subject.

34. The method of any of paragraphs 18-33, wherein the matrix is coated in VEGF or a TGF□ inhibitor.

35. The method of paragraph 34 or 22, wherein the TGF□ inhibitor is an ALK5 inhibitor.

36. The method of paragraph 18, wherein the subject is a mammalian subject.

37. The method of paragraph 36, wherein the mammalian subject is a human subject.

38. The method of paragraph 36, wherein the mammalian subject is an animal.

39. The method of paragraph 38, wherein the animal is selected from the group comprising a rodent, monkey or pig.

40. A composition comprising a substantially pure population of human ISL1+ primordial cardiovascular progenitor cells.

41. The composition of paragraph 40, wherein the human ISL1+ progenitors are negative for the expression of Nkx2.5 and/or KDR.

42. The composition of paragraph 40, wherein the population of human ISL1+ progenitors are derived from human ES cells.

43. The composition of paragraph 40, wherein the population of human ISL1+ progenitors are derived from human ES cell lines or from iPS cells.

44. The composition of paragraph 40, wherein the population of human ISL1+ progenitors are genetically modified human ISL1+ progenitors.

45. The composition of any of paragraphs 40 to 44, further comprising VEGF.

46. The composition of any of paragraphs 40 to 45, wherein the VEGF is VEGF165.

47. The composition of any of paragraphs 40 to 45, wherein the VEGF is selected from the group consisting of: VEGF165, VEGF A, VEGF B, VEGF C, VEGF D, VEGF E, and VEGF F.

48. The composition of any of paragraphs 40 to 44, further comprising a TGFβ inhibitor.

49. The composition of paragraph 48, wherein the TGFβ inhibitor is a ALK5 inhibitor.

50. The composition of any of paragraphs 48 to 49, wherein the TGFβ inhibitor is an ALK5 inhibitor.

51. The composition of paragraph 50, wherein the ALK5 inhibitor is SB431542 or A-83-01.

52. The composition of any of paragraphs 40 to 44, further comprising at least one additional growth factor, selected from any of the group consisting of: FGF, PDGFβ, ECGF, angiopoientin like proteins, IGF-1, HGF, PLDF, Interleukins and variants thereof.

53. The composition of any of paragraphs 40 to 44, wherein the VEGF is at a concentration of between 25-50 ng/ml.

54. The composition of any of paragraphs 40 to 44, wherein the VEGF is at a concentration of between 2-10 ng/ml.

55. The composition of paragraph 49, wherein the ALK5 inhibitor is at a concentration of between 25-50 ng/ml.

56. The composition of paragraph 49, wherein the ALK5 inhibitor is at a concentration of between 2-25 ng/ml.

57. A composition comprising a substantially pure population of human ISL1+/CD31+ progenitors derived from human Isl1+ primordial cells.

58. The composition of paragraph 57 produced by the methods of paragraph 1 to 17.

59. A container comprising the composition of any of paragraphs 40 to 46 and a suitable stem cell media.

60. A composition comprising human three-dimensional vascularized cardiac tissue produced by the method of paragraph 18 to 39.

61. The use of the composition of any of paragraphs 40 to 58, for the treatment of cardiovascular disease or disorder in a subject, wherein the composition is administered to the subject in need of treatment.

62. A container comprising the composition of paragraph 60 and a suitable media.

63. A method for treatment of cardiovascular disease in a subject, the method comprising administering to a subject a composition comprising human three-dimensional vascularized cardiac tissue.

64. The method of paragraph 63, wherein the human three-dimensional vascularized cardiac tissue is produced by the method of paragraphs 18 to 39.

65. The method of paragraph 63, wherein the human three-dimensional vascularized cardiac tissue is administered in a pharmaceutical acceptable carrier.

66. The method of paragraph 65, wherein the pharmaceutical acceptable carrier is a gel.

67. The method of paragraph 63, wherein the human three-dimensional vascularized cardiac tissue further comprises a scaffold or matrices.

68. The method of paragraph 63, wherein the scaffold or matrices further comprises VEGF or a TGFβ inhibitor or both.

69. The method of paragraph 68, wherein the VEGF or a TGFβ inhibitor coat the surface of the scaffold or matrices.

70. The method of any of paragraphs 68 or 69, further comprising VEGF.

71. The method of any of paragraphs 68 or 69, wherein the VEGF is VEGF165.

72. The method of any of paragraphs 68 or 69, wherein the VEGF is selected from the group consisting of: VEGF165, VEGF A, VEGF B, VEGF C, VEGF D, VEGF E, and VEGF F.

73. The method of any of paragraphs 68 or 69, wherein the TGFβ inhibitor is a ALK5 inhibitor.

74. The method of paragraphs 73, wherein the TGFβ inhibitor is an ALK5 inhibitor.

75. The method of paragraphs 74, wherein the ALK5 inhibitor is SB431542 or A-83-01.

76. The method of any of paragraphs 63 to 75, wherein the scaffold or matrices further comprises at least one additional growth factor, selected from any of the group consisting of: FGF, PDGFβ, ECGF, angiopoientin like proteins, IGF-1, HGF, PLDF, Interleukins and variants thereof.

77. The method of paragraph 63, wherein the human three-dimensional vascularized cardiac tissue is administered to the heart of the subject.

78. The method of paragraph 63, wherein the human three-dimensional vascularized cardiac tissue is attached on or within the surface of the heart of the subject.

79. The method of paragraph 63, wherein the human three-dimensional vascularized cardiac tissue is placed as a patch on the subjects heart at the location of injury, damage or malfunction of the heart.

80. An in vivo assay of human cardiovascular disease, comprising an animal subject comprising a population of human ISL1+ primordial progenitors, wherein the human ISL1+ primordial cardiovascular progenitors have undergone coordinated differentiation into cardiomyocytes, endothelial cells, and smooth muscle cells to generate human three-dimensional vascularized cardiac tissue in the animal subject.

81. The in vivo assay of paragraph 80, wherein the animal subject is selected from the group of subjects; rodent, mice, monkey, pig.

82. The in vivo assay of paragraph 81, wherein the animal subject is a knock out or transgenic rodent.

83. The in vivo assay of paragraph 80, wherein the knock out rodent is LDR knockout mouse (LDR −/−).

84. The in vivo assay of paragraph 83, wherein the LDR knockout mouse (LDR −/−) is fed a high fat diet.

85. The in vivo assay of paragraph 83, wherein the population of human ISL1+ progenitors have been contacted with VEGF or a TGFβ inhibitor or both prior to implanting into the subject.

86. The in vivo assay of paragraph 83, wherein a proportion of the population of human ISL1+ progenitors have differentiated into Isl1+/CD31+ cells.

87. The in vivo assay of paragraph 86, wherein at least about 0.02% the population of human ISL1+ progenitors have differentiated into Isl1+/CD31+ cells.

88. The in vivo assay of paragraph 86, wherein at least about 0.05% or more of the population of human ISL1+ progenitors have differentiated into Isl1+/CD31+ cells.

89. The in vivo assay of paragraph 86, wherein the wherein the human ISL1+ progenitors are implanted on a human three-dimensional scaffold or matrices.

90. The in vivo assay of paragraph 89, wherein the scaffold or matrices further comprises VEGF or a TGF☐ inhibitor or both.

91. The in vivo assay of paragraph 89, wherein the VEGF or a TGFβ inhibitor coat the surface of the scaffold or matrices.

92. The in vivo assay of any of paragraphs 85, 90 or 91, wherein the VEGF is VEGF165.

93. The in vivo assay of any of paragraphs 85, 90 or 91, wherein the VEGF is selected from the group consisting of: VEGF165, VEGF A, VEGF B, VEGF C, VEGF D, VEGF E, and VEGF F.

94. The in vivo assay of any of paragraphs 85, 90 or 91, wherein the TGFβ inhibitor is a ALK5 inhibitor.

95. The in vivo assay of paragraph 94, wherein the TGFβ inhibitor is an ALK5 inhibitor.

96. The in vivo assay of paragraph 95, wherein the ALK5 inhibitor is SB431542 or A-83-01.

97. The in vivo assay of paragraph 89, wherein the scaffold or matrices further comprises at least one additional growth factor, selected from any of the group consisting of: FGF, PDGFβ, ECGF, angiopoientin like proteins, IGF-1, HGF, PLDF, Interleukins and variants thereof.

98. Use of the in vivo assay of any of paragraphs 80 to 97 to identify agents which increase or decrease the function of human three-dimensional vascularized cardiac tissue in the animal subject.

99. The use of the in vivo assay of paragraph 98, wherein an agent which increases or decreases by a statically significant amount at least one of the following properties selected from; contractile force, contractibility, cardiomyocyte atrophy, altered contraction, frequency of contraction, contraction duration, contraction stamina, vascularization of the human three-dimensional vascularized cardiac tissue as compared to the absence of the agent identified the agent which increases or decreases the function of human three-dimensional vascularized cardiac tissue.

100. The use of the in vivo assay of paragraph 98 for identifying an agent which is a cardiotoxic agent.

101. The use of the in vivo assay of paragraph 98 for identifying an agent which increases or decreases blood flow in the human three-dimensional vascularized cardiac tissue.

102. A method of screening agents which affect human cardiovascular function, the method comprising;
a. administering to an animal subject comprising human ISL1+ primordial progenitors at least one agent, wherein the human ISL1+ primordial cardiovascular progenitors have undergone coordinated differentiation into cardiomyocytes, endothelial cells, and smooth muscle cells to generate human three-dimensional vascularized cardiac tissue;
b. monitoring the function of the human three-dimensional vascularized cardiac tissue in the presence of the agent as compared to in the absence of the agent;
wherein an agent which has a statistically significant effect on the function of the human three-dimensional vascularized cardiac tissue as compared to in the absence of the agent identifies the agent as having an affect on human cardiovascular function.

103. The method of paragraph 102, wherein the population of human ISL1+ progenitors have been contacted with VEGF or a TGFβ inhibitor or both prior to implanting into the subject.

104. The method of paragraph 103, wherein the population of human ISL1+ progenitors comprise a proportion of Isl1+/CD31+ cells.

105. The method of paragraph 103, wherein at least about 0.02% the population of human ISL1+ progenitors comprise proportion of Isl1+/CD31+ cells.

106. The method of paragraph 103, wherein at least about 0.05% or more of the population of human ISL1+ progenitors comprise proportion of Isl1+/CD31+ cells.

107. The method of paragraph 102, wherein the function of the human three-dimensional vascularized cardiac tissue is selected from at least one of; contractile force, contractibility, cardiomyocyte atrophy, altered contraction, frequency of contraction, contraction duration, contraction stamina, vascularization of the human three-dimensional vascularized cardiac tissue.

108. The method of paragraph 107, wherein the function of the human three-dimensional vascularized cardiac tissue is selected from at least one of; differentiation, survival and regeneration of the human three-dimensional vascularized cardiac tissue.

109. The method of paragraph 102, wherein administration of the agent is selected from the group of systemic administration, intravenous, transdermal, intrasynovial, intramuscular, oral administration, parenteral administration, intraarterial administration, intrathecal administration, intraventricular administration, intraparenchymal, intracranial, intracisternal, intrastriatal, and intranigral administration, and intracoronary administration.

110. The method of any of paragraphs 102 to 109, wherein the population of human ISL1+ progenitors is present on a scaffold or matrices.

111. The method of any of paragraphs 102 to 110, wherein the scaffold or matrices further comprises VEGF or a TGFβ inhibitor or both.

112. The method of any of paragraphs 102 to 111, wherein the VEGF or a TGFβ inhibitor coat the surface of the scaffold or matrices.

113. The method of any of paragraphs 103, 111 or 112, wherein the VEGF is VEGF165.

114. The method of paragraph 113, wherein the VEGF is selected from the group consisting of: VEGF165, VEGF A, VEGF B, VEGF C, VEGF D, VEGF E, and VEGF F.

115. The method of any of paragraphs 103, 111 or 112, wherein the TGFβ inhibitor is a ALK5 inhibitor.

116. The method of paragraphs 115, wherein the TGFβ inhibitor is an ALK5 inhibitor.

117. The method of paragraphs 116, wherein the ALK5 inhibitor is SB431542 or A-83-01.

118. The method of any of paragraphs 110 to 117 wherein the scaffold or matrices further comprises at least one additional growth factor, selected from any of the group consisting of: FGF, PDGFβ, ECGF, angiopoientin like proteins, IGF-1, HGF, PLDF, Interleukins and variants thereof.

119. A non-human animal comprising the three-dimensional human vascularized cardiac tissue of paragraph 18.

120. A clonal cell line comprising substantially pure population of human ISL1+ progenitors.

121. A clonal cell line comprising substantially pure population of Isl1+/CD31+ cells differentiated from human ISL1+ progenitors.

EXAMPLES

Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Methods

Human Fetal Heart Immunohistochemistry.

Human fetal hearts were obtained from authorized resources and embedded in OCT. Sections were stained with different antibody combinations as previously described[6,18]. Hematoxylin and eosin (Sigma-Aldrich) staining was applied to adjacent slides to reveal tissue structures.

hES cell culture and differentiation. hES cells were maintained in standard hES culture as described[10,22]. To generate embryoid bodies for in vitro differentiation, hES cells were treated with 0.5 mg/ml Dispase (Gibco), then suspended in hES cell differentiation medium, transferred to 6-well ultra low cluster plates (Costar) and cultured at 37° C. with 5% $CO_2$. Embryoid bodies were dissociated into single cells using 0.25% trypsin-EDTA and stained with DAPI. The sorted cells were plated on 24-well plates with irradiated MEF feeders and cultured in human B27 medium. After 10-14 days of culture, colonies were picked for differentiation and RNA isolation.

BAC Recombineering and hES Cell Genetic Modification.

Recombineering was performed as described[23,24]. The βgeo cassette is integrated into the ISL1 endogenous locus through homologous recombination. A new targeting BAC was constructed by replacing the βgeo reporter with a cre-IRES-puro cassette. An additional retrieving vector was made for retrieving the final knock-in construct from the recombineered ISL1-cre BAC. Electroporation was performed as previously described[10,25,26] with modifications. The hES cells were subjected to a single pulse at room temperature and plated on irradiated DR4 MEF feeders. Antibiotics selection was applied after three days.

Human Fetal Heart Immunohistochemistry.

Human fetal hearts were obtained from authorized sources. The pericardium was removed and the tissue was freshly fixed in 4% PFA at 4° C. overnight. The heart was washed four times with 1×PBS at 4° C. and embedded in OCT after going through a sucrose gradient. 8 μm sections were stained with different antibody combinations as previously described[6,18] Primary antibodies used for staining are: anti-ISL1 mouse monoclonal antibody (Developmental Studies Hybridoma Bank), anti-cTNT rabbit polyclonal antibody (Abcam), anti-SMMHC rabbit polyclonal antibody (Biomedical Technologies Inc.), anti-NKX2-5 rabbit polyclonal antibody (Santa Cruz), and anti-KDR/Flk1 rabbit polyclonal antibody (Upstate). Alexa Fluor 488- or Alexa Fluor 594-conjugated secondary antibodies were purchased from Molecular Probes. Hematoxylin and eosin (Sigma-Aldrich) staining was applied to adjacent slides to reveal tissue structures.

hES Cell Culture.

hES cells H9 (WiCell Research Institute, NIH code WA09) and HUES3 (Harvard University) were maintained in standard hES culture as described10, 22. To generate embryoid bodies for in vitro differentiation, hES cells were treated with 0.5 mg/ml Dispase (Gibco) at 37° C. for 20 minutes. Cells were then suspended in hES cell differentiation medium (DMEM/F12 (Gibco) containing 18% FBS (BenchMark), 0.1 mM NEAA (Gibco), 2 mM L-Glutamine (Gibco) 5.5 mM 2-Mercaptoethanol (Sigma) and 50 ng/ml Ascorbic Acid (Sigma)), transferred to 6-well ultra low cluster plates (Costar) and cultured at 37° C. with 5% $CO_2$.

BAC recombineering. Recombineering was performed as described[23,24]. Briefly, human BAC clone CTD-2314G24, which contains all exons of ISL1 gene and extends from 100.7 kb upstream to 26.1 kb downstream of the translation start site was introduced into *E. coli* strain SW102. A targeting vector was constructed with two 350 bp homologous arms and a βgeo reporter followed by an antibiotics cassette providing resistance in both eukaryotes and prokaryotes. The targeting vector was linearized and electroporated into SW102 containing BAC CTD-2314G24 and activated recombinases. The transformed bacteria were plated on LB plates with appropriate antibiotics and incubated at 37° C. for 18-24 hours. Selected clones were picked and subjected to PCR to confirm successful recombination.

Construction of Knock-in Vector.

A new targeting vector was constructed by replacing the βgeo reporter of above targeting vector with a cre-IRES-puro cassette. Recombineering was performed by introducing the new vector into SW102 containing BAC CTD-2314G24 and activated recombinases described above. An additional retrieving vector containing a 500 bp fragment at 5' of the 9.2 kb 5' arm and a 500 bp fragment at 3' of the 5.5 kb 3'arm homologous to ISL1 exon 1 was made for retrieving the final knock-in construct from the recombineered ISL1-cre BAC.

Electroporation Transfection.

Electroporation was performed as previously described[10,25,26] with modifications. Human ISL1-βgeo BAC and ISL1-cre knock-in vector were linearized by Lambda terminase (Epicentre Biotechnologies) and restriction enzymes respectively, and sterilized by ether extraction. hES cells were trypsinized and filtered through 100 μm cell strainers. Cells were then centrifuged and resuspended in hES cell culture medium with 1×PBS. 15-30 μg linearized DNAs were added into resuspended hES cells. The cells were subjected to a single 320 V, 200 μF pulse (BioRad GenePulser Xcell CE module) at room temperature and plated on irradiated DR4 MEF feeders. Antibiotics selection was applied three days post electroporation. Southern blotting and long range PCR confirmed the homologous integration of the human ISL1-cre knock-in construct. Genomic DNA was digested with BamHI restriction enzyme and a 500 bp fragment upstream of 5' homologous arm was used as 5' probe. The human ISL1-cre knock-in lines have a 26 kb wild type band and a 11 kb mutant band.

Flow Cytometry.

Embryoid bodies were dissociated into single cells using 0.25% trypsin-EDTA and stained with DAPI. Forward scatter (FSC) versus side scatter (SSC), and forward scatter height (FSC) versus width (FSC—W) were used to exclude debris and doublet. DAPI positive population, representing dead cells, was excluded during FACS (BD FACSAria). DsRed+ cells were isolated from day 8 EBs. Sorting data were analyzed using the FlowJo software (Treestart). Anti-KDR antibody was purchased from R&D Systems.

Clonal Assay.

The sorted cells were plated on 24-well plates with irradiated MEF feeders and cultured in human B27 medium (DMEM/F12 (Gibco) containing 5% KOSR (Invitogen), 1× human B27 supplements (Gibco, supplied as 50× stock), 5 ng/ml of human recombinant basic FGF (Millipore) and 10 ng/ml of human EGF (Sigma). After 10-14 days of culture, colonies were picked, dissociated and seeded on fibronectin-coated chamber slides for differentiation.

RT-PCR.

Total RNA was isolated using Absolutely RNA Nanoprep Kit (Stratagene) and was reverse transcribed using iScript cDNA Synthesis Kit (BioRad). Primer sequences and PCR conditions are available upon request. qPCR was performed on MasterCycler EP RealPlex (Eppendorf) using iQ SYBR Green SuperMix (BioRad). Standard deviations (s.d.) of the means in qPCR experiments were obtained from three independent experiments.

Example 1

Figure 1B:
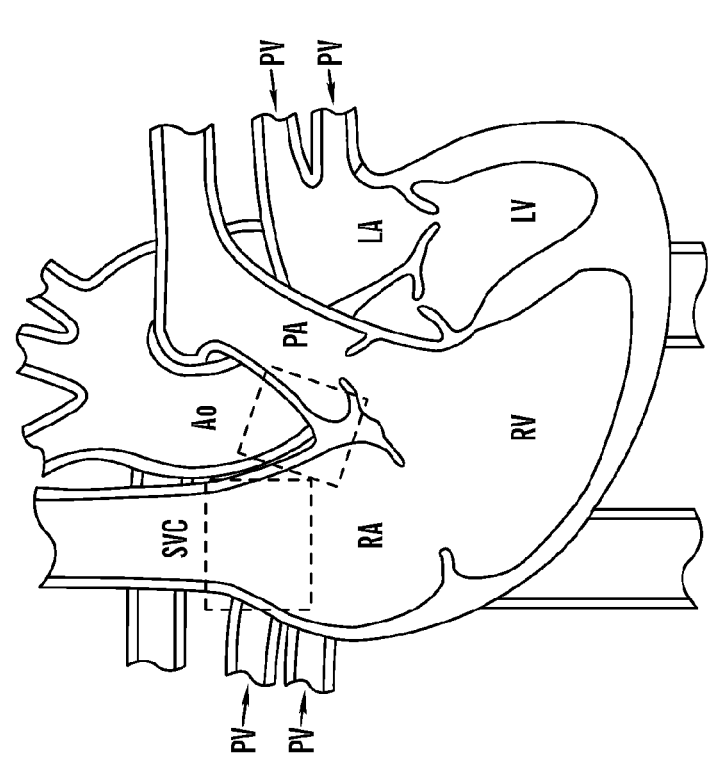

To localize ISL1+ heart cells during human cardiogenesis, the inventors employed immunofluorescence microscopy in serial sections of human fetal hearts at 11 and 18 weeks of gestation. ISL1+ cells were found in the right atrium (RA) and outflow tract (OFT), both second heard field (SHF)-derived structures (FIG. 1), as well as in the left atrial wall and appendage. In particular, the inventors demonstrated that in vivo expression of ISL1 in the human fetal heart using hematoxylin eosin staining of left atrium and left atrium appendage of a human fetal heart at 11 weeks of gestation (data not shown). The inventors also performed double immunostaining of sections of the human heart from RA region with antibodies directed to ISL1 and antibodies directed to one or more of cTNT, SMMHC, PECAM1, NKX2.5 and detected double immunostained cells positive for ISL1 and PECAM1 (data not shown).

Figure 1B:
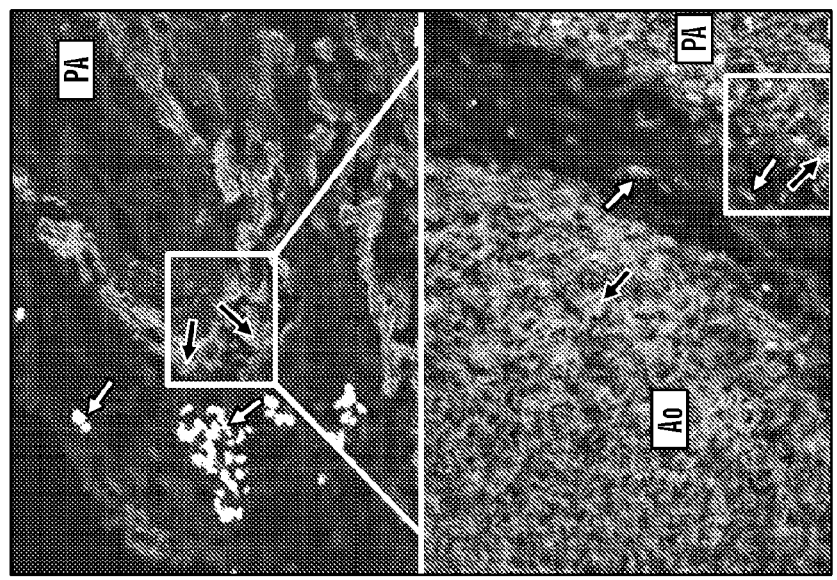

Thus, the inventors demonstrated that ISL1+ cells in the human fetal heart are found in pattern that matches the known contribution of Isl1+ precursors to SHF derivatives in the murine fetal heart[6,8,9] Furthermore, the inventors performed co-staining of ISL1 and the lineage specific differentiation markers, cardiac troponin T (cTNT, cardiamyocyte), smooth muscle myosin heavy chain (SMMHC, smooth muscle cell) (FIG. 1), and the platelet/endothelial cell adhesion molecule (PECAM1, endothelial cell) (data not shown). Double positive cells, expressing ISL1 as well as a lineage-specific differentiation marker, were identified as intermediates for the cardiomyocyte, smooth muscle and endothelial lineages. Surprisingly, the inventors identified a unique subset of cells which express ISL1, but not NKX2-5 or differentiated cardiac lineage markers in the right atrial wall and proximal OFT (FIG. 1, and data not shown). The inventors also performed similar double immunostaining of adjacent sections from human fetal hearts at 11 weeks and at 18 weeks of gestation with antibodies directed to ISL1 and antibodies directed to one or more of cTNT, SMMHC, PECAM1, NKX2.5 and detected double immunostained cells positive for ISL1 and PECAM1 at 11 and 18 weeks of gestation (data not shown). Thus, in later-stage fetal hearts (18 weeks of gestation), the relative and total numbers of ISL1+ cells were significantly reduced. Collectively, these findings demonstrate that ISL1 is expressed over a long period of human cardiogenesis and further demonstrate a unique subset of primordial ISL1+ progenitors which give rise to downstream multipotent heart progenitors that contribute to the SHF (second heart field) derived structures through differentiation into multiple lineage-restricted ISL1+ intermediates.

Figure 2A:
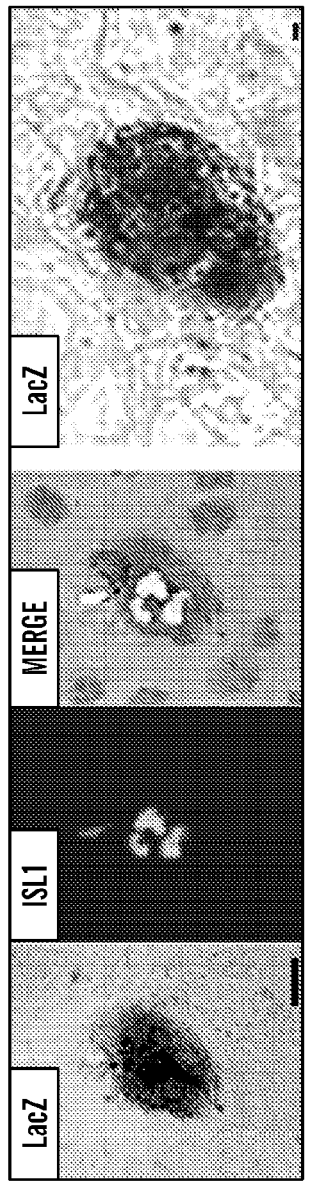
FIGS. 2A-2E show ISL1 expression marks hES cell-derived cardiac progenitors.
Figure 6A:
FIGS. 6A-6B show the generation of transgenic and knock-in hES cell lines.

To study the early cell fate decisions taken by ISL1+ human cardiovascular progenitors, and to characterize ES cell derived human cardiac ISL1+ progenitors, the inventors generated an ISL1-βgeo BAC transgenic hES cell line in order to genetically tag ISL1+ progenitors (FIG. 6A). After 5-6 days of embryoid body (EB) formation, βgeo+ cells were detected by X-gal staining. Co-staining of X-gal and ISL1 (FIG. 2A, left panel) confirmed that βgeo expression driven by regulatory sequences present in the ISL1 BAC recapitulated the expression pattern of the endogenous ISL1 protein. Single cell derived clones from EBs of human ISL1-βgeo BAC transgenic cells were observed on mouse cardiac mesenchymal cells (CMC) after five days of in vitro expansion. Of these clones, 10±5% had focal βgeo activity (FIG. 2A, right panel).

Figure 2B:
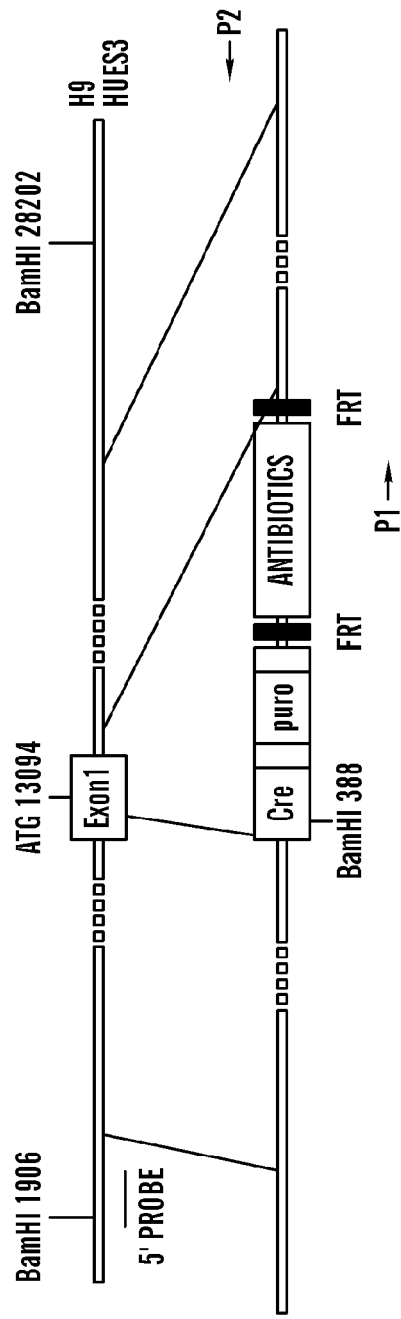
Figure 2D:
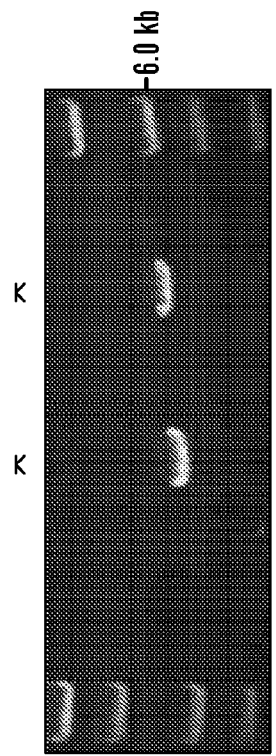
Figure 2C:
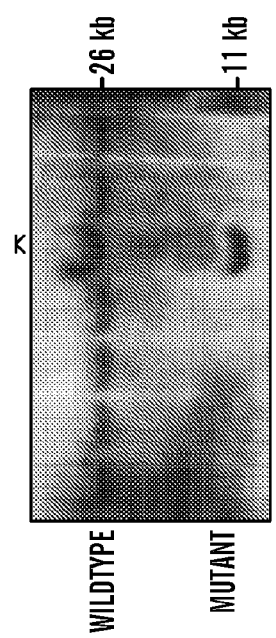
Figure 2E:
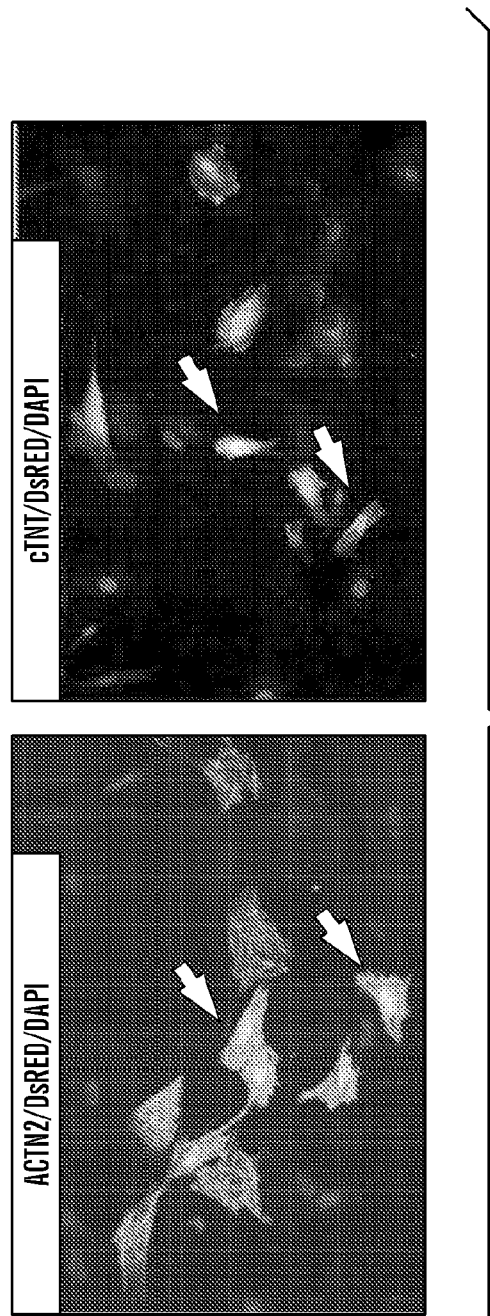
Figure 6B:
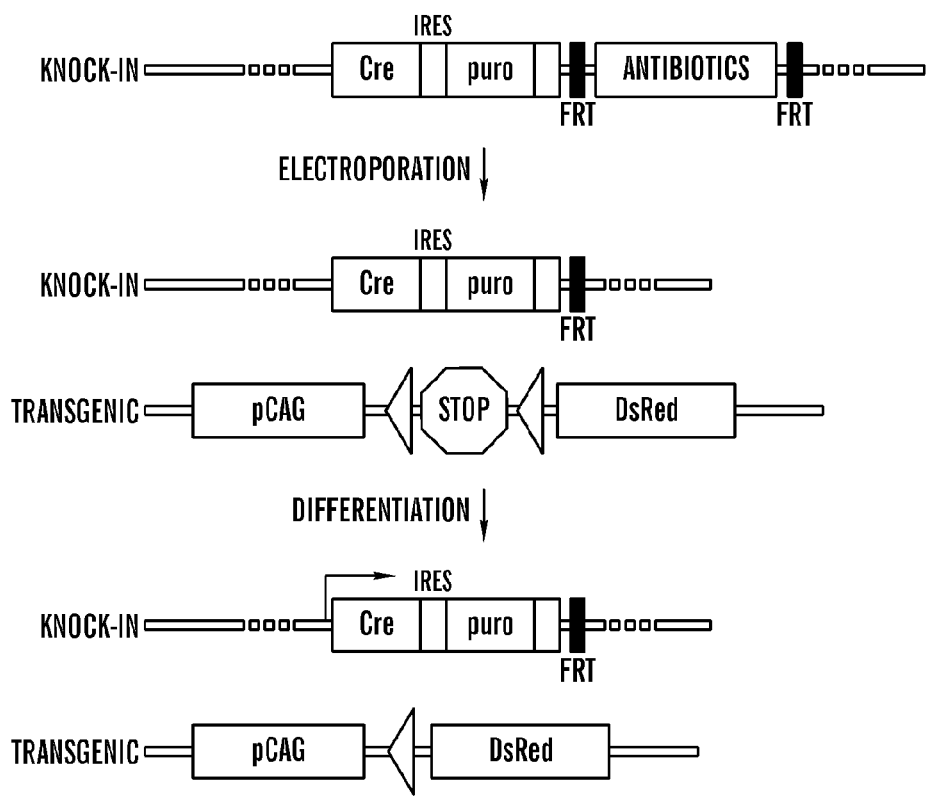

To identify, purify and track the fate of hES cell-derived ISL1+ progenitors, the inventors employed lineage tracing with a Cre-LoxP system to irreversibly mark ISL1 expressing cells and their differentiated progeny in the context of in vitro human cardiac differentiation. The ISL1-cre knock-in hES cell lines (using WA09 and HUES3 as parental hES cell lines[10]) were identified by Southern blotting using a 5' probe and by 3' long range PCR (FIG. 2B-2C). Immunostaining assay documented that Cre expression recapitulated endogenous ISL1 expression (Data not shown). The inventors performed immunostating with antibodies which recognize Cre and Isl1 and demonstrated that cells dissociated from day 6 EBs of the human ISL1-cre knock-in line stained positive for both cre recombinase and ISL1 after a two-day co-culture with feeders (data not shown). The ISL1-cre cells were then co-transfected with a pCAG-flox-DsRed reporter plasmid and a pCAG-Flpase plasmid (FIG. 6B). Cre expression from the ISL1 locus mediates the excision of the floxed stop sequence on the pCAG-flox-DsRed plasmid resulting in the irreversible expression of the DsRed-MST11 gene in ISL1+ progenitors and their differentiated progeny (FIG. 6B). Approximately 20-30% of beating EBs in the ISL1-cre DsRed cells on EB day 16 expressed DsRed (FIG. 7D, and data not shown). Immunostaining displayed co-expression of ISL1 and DsRed in the cells dissociated from day 8 EBs demonstrating co-expression of ISL1 and DsRed in the human ISL1-cre DsRed cells dissociated from day 8 EBs (data not shown). The ISL1-cre DsRed cell derived population also co-expressed DsRed and sarcomeric α-actinin (ACTN2) or cTNT (FIG. 2E), demonstrating that a portion of human cardiomyocytes were derived from ISL1+ cardiac progenitors.

RT-PCR analysis on human ISL1-cre DsRed EBs revealed a dynamic pattern of DsRed and cardiac marker expression (FIG. 3A). DsRed expression was undetectable in undifferentiated hES cells, but increased along with the expression of ISL1 during differentiation. The SHF specific marker TBX112 and the cardiac transcription factor NKX2-5 were not expressed until EB day 6 and 8 respectively. The late cardiac marker, myosin heavy chain 6 (MYH6) was first detected on EB day 10 (FIG. 3A). Taken together, these results demonstrate that the human EB differentiation program in vitro correlates with the normal human embryonic cardiac developmental program.

Example 2

Figure 3C:
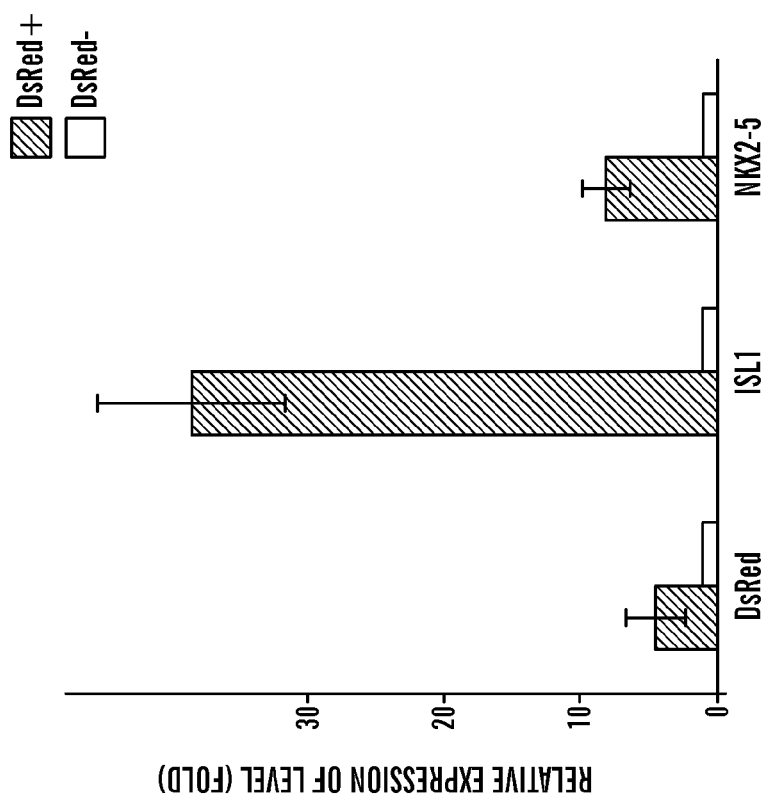
Figure 7B:
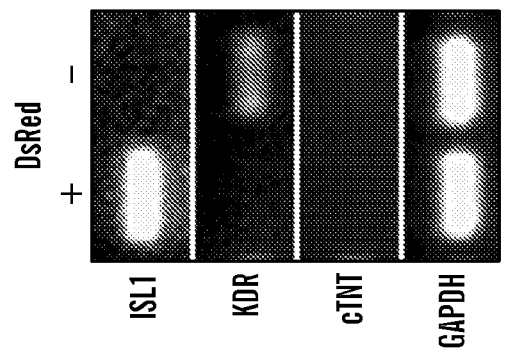
FIG. 7B shows a scheme of the human ISL1-cre DsRed lineage tracing strategy in hES cell model system. In order to reduce potential effects on the regulatory sequences of the ISL1 locus, the FRT-flanked antibiotics cassette in knock-in locus was excised by transient transfection of an Flpase expressing plasmid.
Figure 7A:
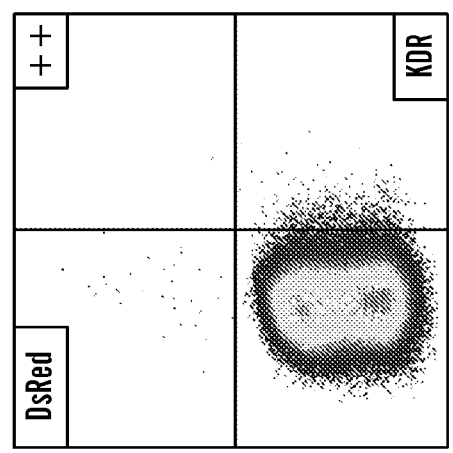

To obtain purified populations of ISL1+ cardiac progenitors, the inventors isolated DsRed+ cells by FACS on EB day 8 (FIG. 3B). RT-PCR analysis revealed that the expression of cardiac markers ISL1 and NKX2-5 is 30- and 8-fold higher in DsRed+ cells than that in DsRed− population, respectively (FIG. 3C). Interestingly, both FACS and RT-PCR analyses demonstrated that DsRed+ cells did not express KDR when isolated on EB day 8 (FIG. 7A-7B).

Figure 3D:
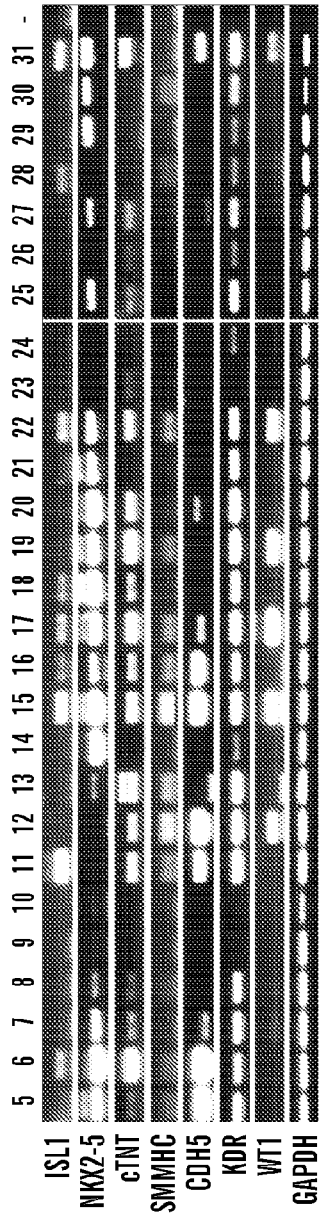

To assess the differentiation potential of human ISL1+ progenitors, the inventors performed clonal assays on single DsRed+ cells. The inventors them isolated DsRed+ cells from day 8 EBs and plated them at low density on mouse embryonic fibroblast (MEF) feeders. Colonies of DsRed+ cells were observed within seven days at a cloning efficiency of 0.2-0.5%. The inventors demonstrated that FACS isolated DsRed+ cells from day 8 human ISL1-cre DsRed EBs formed colonies on MEF feeders after 7-day and 14-days (data not shown). The inventors performed RT-PCR analysis on 95 single DsRed+ cell derived clones (FIG. 3D, Table 2). Many of these clones, expressing NKX2-5 alone or ISL1 and NKX2-5, also expressed late cardiac markers e.g. cTNT, SMMHC, demonstrating they are cardiac progenitors at intermediate stages of differentiation, consistent with the inventor in vivo observations in the human fetal heart (see FIGS. 1A and 1B).

The inventors demonstrated that clones expressing ISL1 and NKX2-5 are more effective (55%, 22/40) at differentiating into the three major cardiovascular lineages and generating cardiomyocytes, as 90% of them (35/40) co-express cTNT (FIG. 3D, Table 2).

TABLE 2

Molecular markers of single DsRed+ cell-derived progenitor clones. The total 95 tested clones are categorized into four groups based on their expression pattern of ISL1 and NKX2-5. The percentage of each group is listed under the group definition. Typical clones of each group are presented with gene expression pattern as well as their total numbers. (% refers to the proportion of cells, numbers in brackets represents the actual number of clones from a total of 95 analyzed).

|  | Isl1+/Nkx2.5+ [42% (40/94)] | Isl1+/Nkx2.5− [22% (21/95)] | Isl1−/Nkx2.5+ [24% (23/95)] | Isl1+/Nkx2.5− [12% (11/95)] |
|---|---|---|---|---|
| 3 lineages |  |  |  |  |
| CTNT+/SMMHC+/CDH5+ [37% (35/95)] | 22 | 5 | 4 | 5 |
| 2 lineages |  |  |  |  |
| CTNT+/SMMHC+ [9% (9/95)] | 6 | 1 | 1 | 1 |
| CTNT+/CDH5+ [12% (11/95)] | 4 | 3 | 4 | — |
| SMMHC+/CDH5+ [1% (1/95)] | 1 | — | — | — |
| 1 lineage |  |  |  |  |
| cTNT [13% (12/95)] | 3 | 1 | 6 | 2 |
| SMMHC [4% (4/95)] | 1 | 1 | 1 | 1 |
| CDH5+ [2% (2/95)] | 1 | 1 | — | — |
| CTNT−/SMMHC−/CDH5− [22% (21/95)] | 2 | 9 | 7 | 3 |

Figure 3E:
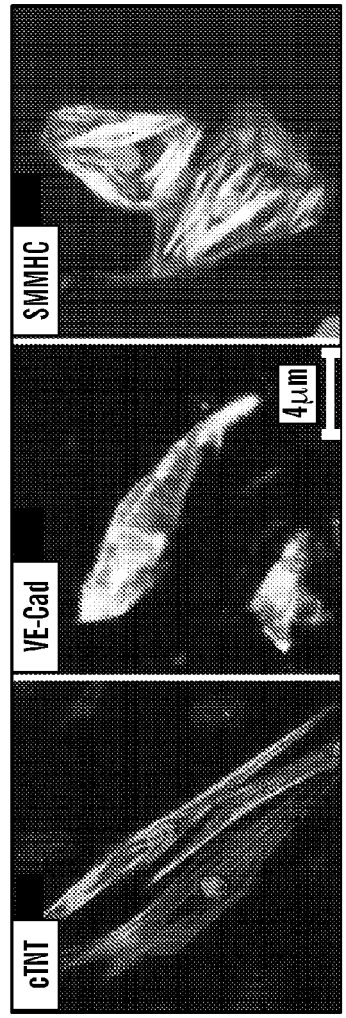
Figures 8A, 8B:
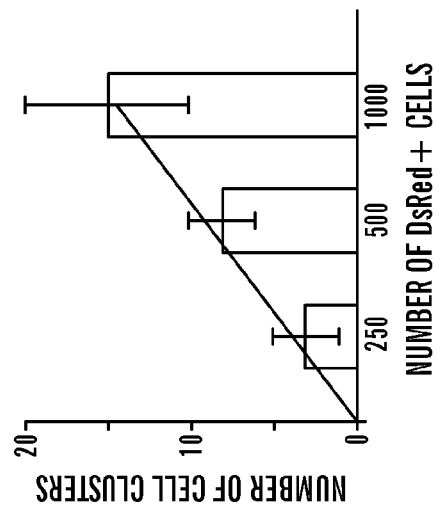
FIGS. 8A-8B show single cell derived clones developed on MEF feeders. To confirm that the DsRed+ colonies studied in the clonal assays are derived from single cells, the inventors generated an additional transgenic pCAG-flox-eGFPESline in the human ISL1-cre knock-in background. DsRed+ and eGFP+ cells were purified from day 8 EBs. Equal numbers of red and green cells were mixed and plated at up to a 4-fold density used in the clonal assay.

Recent studies suggest that KDR and its mouse ortholog, Flk1 can label an enriched pool of early cardiac progenitors'[6,13-15]. The inventors demonstrate that the results are consistent with these findings and further imply that the ISL1+/NKX2-5+/KDR+ cardiac progenitors derived from hES cells may originally arise from an ISL1+/KDR− population (FIG. 7A-7B). However surprisingly, in this study KDR was not an effective single marker for isolating stage-specific cell populations, as it was expressed at multiple stages during cardiac differentiation. In particular, the inventors, using double immunostaining for Isl1+ and KDR of 18 weeks, and 11 weeks of gestation human fetal heart demonstrated co-staining for ISL1 and KDR in the RA areas and demonstrated that some ISL1− (negative) cells are KDR+, and some ISL1+ cells stained negative for KDR (data not shown). Notably, WT1, the human ortholog of a recently identified mouse epicardium precursor marker Wt1[16,17], was detectable in ISL1+/NKX2-5+ and NKX2-5+ clones (FIG. 3E). Thus, the inventors demonstrate that human WT1+ progenitors share a developmental origin with multipotent NKX2-5+ and/or ISL1+ cells. The inventors confirmed this by a two-color system, DsRed+ colonies in the clonal assays were developed from single ISL1+ progenitors (FIGS. 8A, 8B).

To evaluate the developmental potential of ISL1+ lineage cells, the inventors used DsRed+ derived clones which were dissociated for differentiation assays, to identify clones which resulted in contracting DsRed+ clusters on gelatin-coated plates (data not shown). Flow cytometry and immunochemistry analyses demonstrated that DsRed+ cells could give rise to the three major cardiac lineages: cardiomyocytes (4.2±0.3% cTNT+), endothelial cells (3.1±0.9% PECAM1+/VE-Cadherin+) and smooth muscle cells (44.1±15.7% SMTN+/SMMHC+) (FIG. 3f).

Figure 4A:
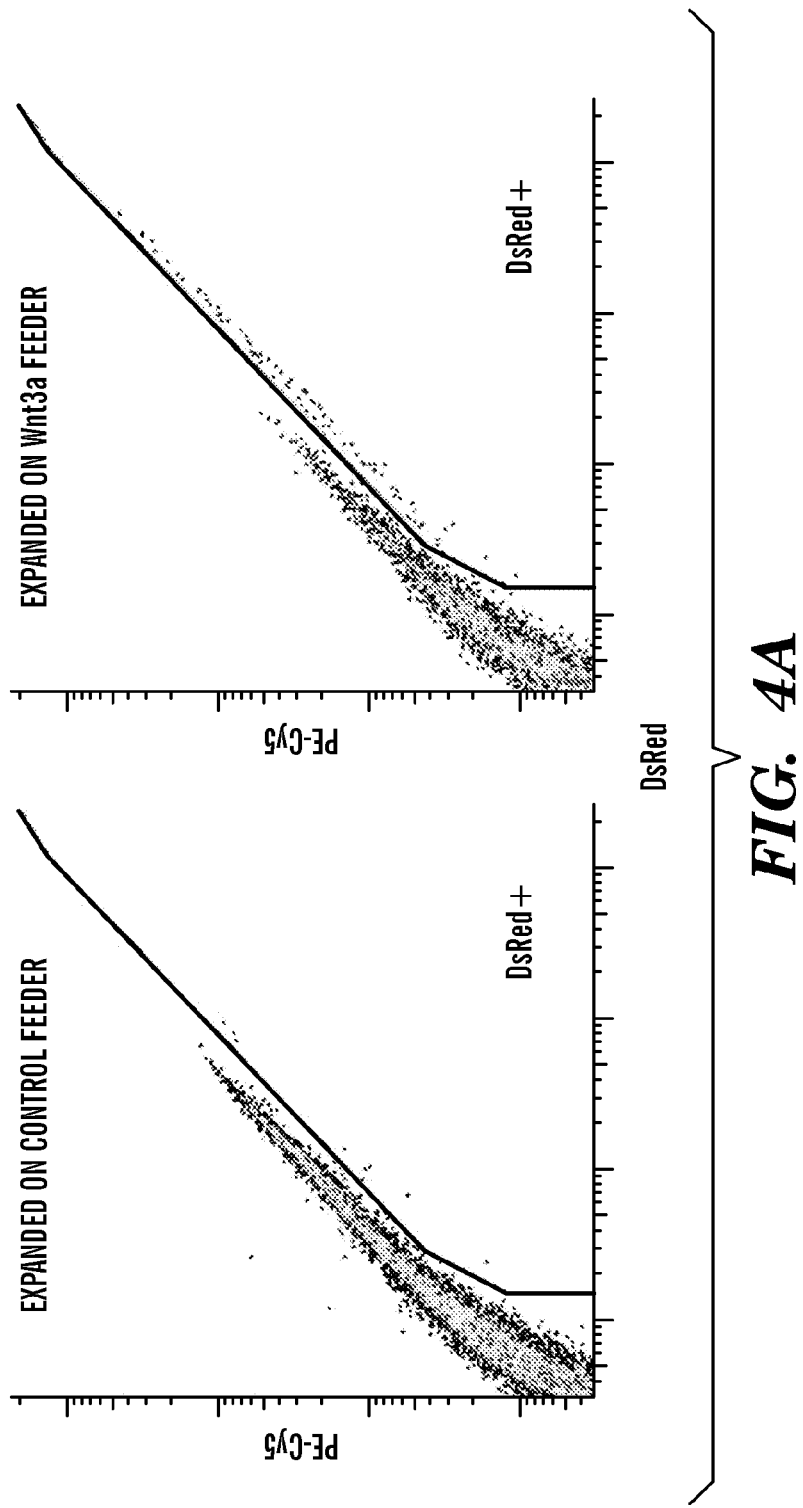
FIGS. 4A-4C shows the expansion of hES cell-derived ISL1+ cardiac progenitors on Wnt3a feeders.
Figure 9B:
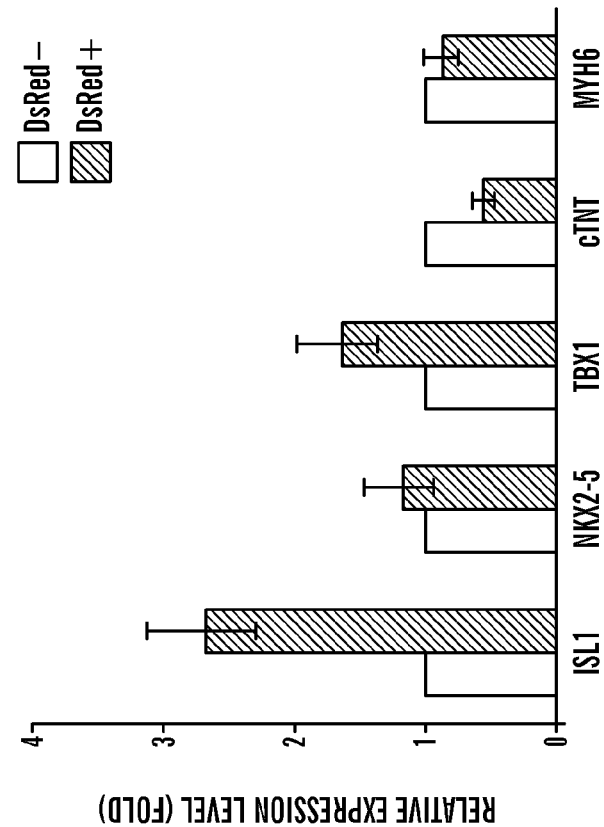
FIGS. 9A-9B show the expansion and characterization of hES cell-derived ISL1+ cardiac progenitors.
Figure 9A:
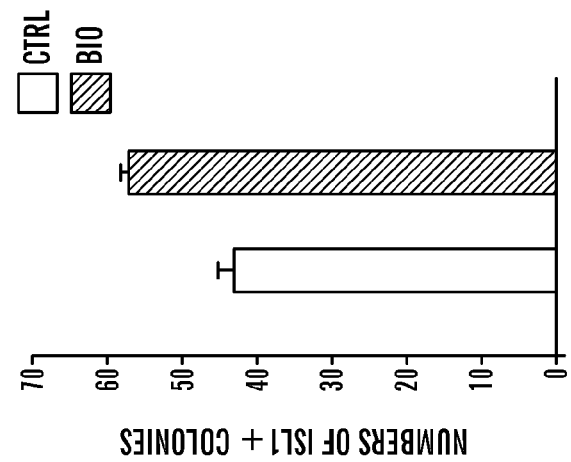
Figure 10A:
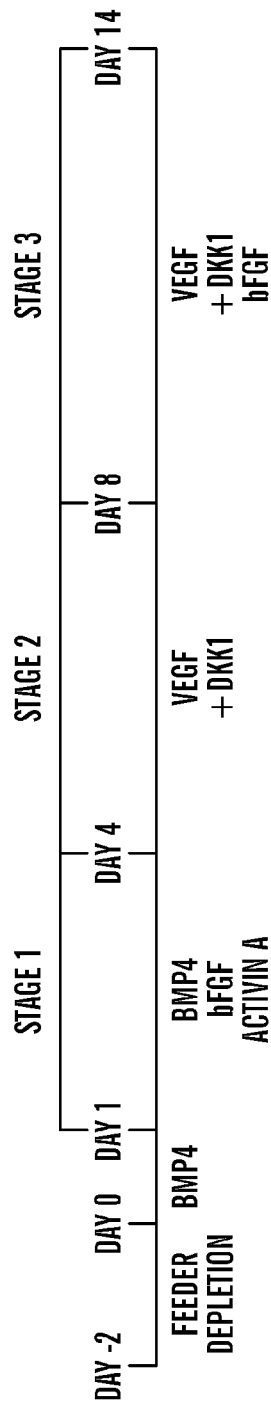
FIGS. 10A-10C show human cardiovascular progenitor cells develop from a KDR$^+$ embryonic stem-cell-derived population and shows the specification of the cardiac linage from human ESCs.
Figure 10C:
Figure 10B:
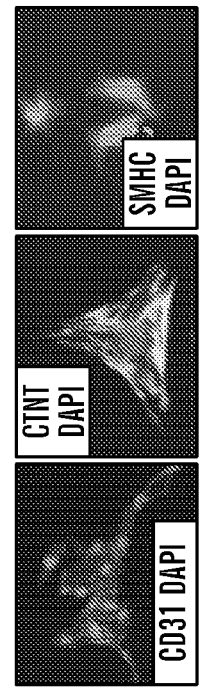

Canonical Wnt pathways can promote the expansion of Isl1+ cardiac progenitors in the mouse[18-20]. In a similar manner, 6-bromoindirubin-3'-oxime (BIO)[21] treatment has been reported to resulted in an over 30% increase of human ISL1+ clones compared to CMC control (FIG. 9A-9B). The inventors then isolated human ISL1-cre DsRed cells from day 7 EBs, which were dissociated and plated on a plastic surface, MEF, Wnt3a-secreting, or L cell feeders. The clonal capacity of DsRed+ cells on different culture surfaces of plastic, MEF, Wnt3a-secreting feeder cells was different, for example the inventors demonstrated that cells dissociated from day 7 EBs of human ISL1-cre DsRed cells were plated on gelatin-coated tissue culture plates, MEF feeders or Wnt3a-secreting feeders respectively and cultured for five days, the DsRed+ cells formed colonies on the Wnt3a feeder layer to a greater extent to that cultured on MEF and few to no colonies were detected on plastic surface (data not shown). No red clusters were formed on plastic surface or L feeders after five days of culture, while co-culturing with Wnt3a-secreting feeders resulted in approximately six-fold increase in DsRed+ cell number and five-fold increase in DsRed+ clusters compared to those cultured on MEF feeders (data not shown). Thus, the inventors demonstrate that DsRed+ cells expanded on Wnt3a feeders exhibited a higher expression of ISL1 (FIG. 4A and FIG. 9B).

Figure 4B:
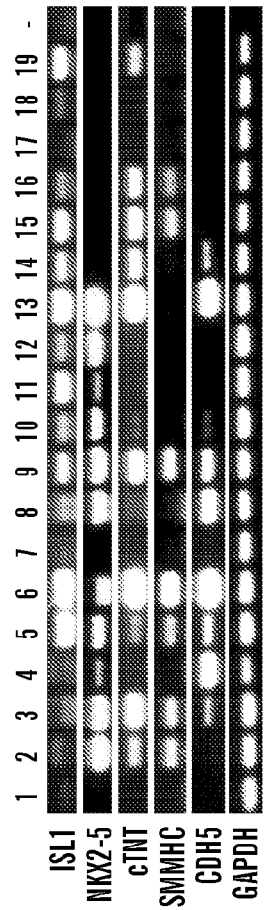
Figure 4C:
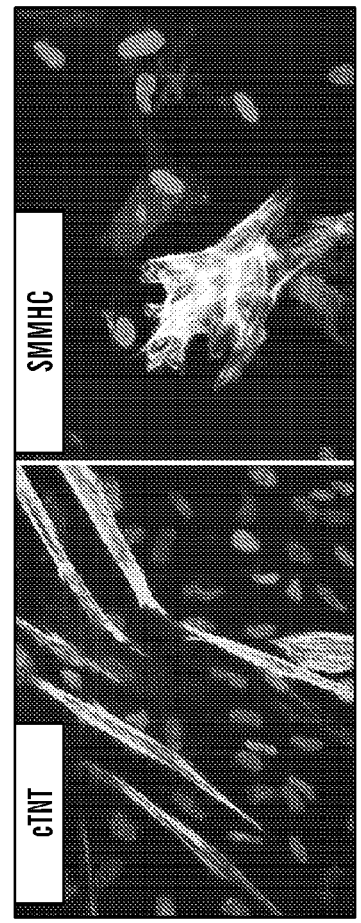

The inventors then performed a similar clonal assay on FACS-purified DsRed+ cells cultured on MEF feeders with Wnt3a-conditioned medium. 12-14 days after plating, nearly 90% (28/32) clones maintained ISL1 expression and around 20% (6/32) clones co-expressed the three cardiac lineage markers (FIG. 4B). After ten days of differentiation, cTNT and SMMHC were detected in Wnt3a-expanded DsRed+ cells (FIG. 4C). Taken together, these results demonstrated that the inventors have discovered that canonical Wnt ligands can promote the expansion and maintain the multipotency of human ES cell-derived ISL1+ progenitors.

Collectively, the inventors have demonstrated that in humans, a primordial human ISL1+ cardiac progenitor is negative for KDR and NKX2.5 (e.g. human primordial ISL1+ cardiac progenitors are Isl1+/KDR−/Nkx2.5), and gives rise to a family of intermediate progenitors of multiple cardiac lineages, including the WT1+ epicardial lineage (see FIG. 3D and FIG. 5). Furthermore, while KDR has been used as a marker to obtain populations of hES cell derived progenitors that are enriched for ISL1 expression[13], as noted herein, KDR is widely expressed outside the heart, thus use of KDR as a marker to isolate and clonally study purified populations of ISL1+ progenitors is limited.

In this study, via lineage tracing in hES cells, the inventors have demonstrated a method to isolate primordial human ISL1+ cardiac progenitor which are negative for KDR and NKX2.5 (e.g. Isl1$^{-1}$/KDR$^-$/Nkx2.5$^-$ primordial cardiac progenitors) by directly labeling the ISL1+ cells, and have also identified a method to purify these Isl1+ cardiac progenitors to relative homogeneity, as well as tracked their downstream progeny. The inventors have demonstrated that ISL1 is expressed at early stages of human cardiogenesis in a multipotent primordial progenitor, and subsequently in a family of partially committed intermediate progenitors, which is down-regulated in the fully differentiated progeny (FIG. 3D).

These human ISL1+ progenitors give rise to both the right ventricle, and inflow/outflow tracts, that are affected in several common forms of human cardiovascular malformations (e.g., transposition of the great vessels, tricuspid atresia, Tetralogy of Fallot), demonstrating their role in diverse forms of human congenital heart disease. Additionally, the inventors have surprisingly discovered, in contrast to murine cardiogenesis, large numbers of multipotent ISL1+ progenitors persist during later stages of human fetal cardiogenesis, demonstrating a stem cell paradigm for the exponential growth of the human fetal heart and outflow tract over many weeks, which may arise from expansion of the family of ISL1+ progenitors. Taken together, the inventors have demonstrated that hES cell-derived ISL1+ progenitors may provide new insights into human congenital heart disease, as well as novel model systems for human cardiovascular disease and new therapeutic approaches for adult cardiovascular defects.

Example 3

Cardiovascular disease is the leading cause of death in the U.S., and will be the primary cause of mortality in developing countries by 2010, as estimated by the WHO. Nevertheless, the demand for transplantation exceeds the availability of donor hearts. In this regard, cardiac regeneration has recently become an active area of research. Over the past few years, numerous reports demonstrate cardiac progenitors from diverse fetal and adult tissues outside the cardiovascular system, including adipose tissues, amniotic fluid, bone marrow, placenta, skeletal muscle, and testes (Franco et al., 2007). However, their low frequency of cardiac differentiation (Murry et al., 2004) and lack of long-term benefits fail to achieve cardiac cell regeneration (Fazel et al., 2006, 2008). Bone marrow cells, for instance, may improve the function of the infarcted heart mainly by promoting angiogenesis or cell survival without cardiac muscle regeneration (Fazel et al., 2006, 2007). A recently discovered cardiac progenitor population marked by the expression of the LIM homeodomain transcription factor is 11 (Laugwitz et al., 2005; Moretti et al., 2006; Qyang et al., 2007) is an attractive target to study cardiac regeneration. A multipotent islet 1 (isl1+) progenitor is able to give rise to the major three cell types of the heart: cardiomyocytes, smooth muscles and endothelial cells, and has clonogenic and self-renewing ability (Laugwitz et al., 2005; Moretti et al., 2006). In Isl1 knockout mice, histological analysis of mutant hearts between embryonic day (ED) 9.0 and ED9.5 showed a misshapen single heart ventricle as the cause of death (Cai et al., 2003). Lineage tracing studies document that isl1+ progenitors give rise to over two thirds of the cells in the heart, mostly on the right side, including most of the conduction system: the sinoatrial (SA) node, the atrioventricular (AV) node, His-bundle, and Purkinje fiber complex (Cai et al, 2003; Laugwitz et al., 2005; Moretti et al., 2006; Sun et al., 2007). Disruption of development, differentiation or maturation of any of these components can lead to arrhythmias such as sinus arrest, AV block, ventricular tachycardia and sudden death (Bruneau et al., 2001).

The inventors herein demonstrate isolation of human ISL1+ primordial progenitors and differentiating them into specified cardiac cells, to generate functional cardiac cells in the heart.

Thus, the inventors demonstrate the potential of differentiating human embryonic stem (ES) cells into human ISL1+ primordial progenitors and further differentiating the human ISL1+ primordial progenitors, in vivo, into cardiac, smooth, and endothelial lineages, leading to the development of functional myocardium.

Moreover, the inventors also demonstrate that to improve viability of the implanted ISL1+ primordial progenitors and to prolong graft survival, the inventors have genetically modified the human ISL1+ primordial progenitors by inhibiting apoptosis, promoting survival pathways, and minimizing immune rejection of the isl1+ progenitors and their differentiated cardiac cells, for example by expressing trunkated form of Creb312.

ES cells can self-renew and have the best-proven cardiac potential. The inventors have previously demonstrated that mouse isl1+ cardiac progenitors can be derived from mouse ES cells (Moretti et al., 2006). Moreover, the murine ES cell-derived isl1+ progenitors, which are multiptent Isl1+ cardiovascular progenitor cells (MICPs) which are Isl1+/Nkx2.5+/Flk+ can be further differentiated into cardiomyocytes, smooth muscle cells, and endothelial cells (Moretti et al., 2006; Qyang et al., 2007). More recently, the inventors have also previously demonstrated that isolated committed cardiomyogenic progenitors (CMP), also known as committed ventricular progenitors (CVPs) are an isl1+ lineage derived from ES cells, which give rise to ventricular cardiomyocytes. Therefore, the ability to develop the multipotent isl1+ progenitors from human ES cells demonstrates a strategy for cardiovascular tissue regeneration via their isolation, renewal and directed differentiation into specified cell types.

While human ES cells have been suggested as a renewable source for cardiac cell regeneration, this has been challenging given that ES cell-derived grafts are rejected across barriers of multiple minor histocompatibility (mH) and major histocompatibility complex (MHC) (Robertson et al., 2007). Although iPS cells could be a syngeneic source of cells for transplantation, the methods of generating iPS cells by retrovirally transfecting the four pluripotency-inducing transcription factors may induce insertional mutagenesis (Kim et al., 2008). Moreover, there are hundreds of differences between the transcriptional profiles of iPS cells and authentic ES cells; it is unclear whether the differentiated progeny of iPS cells have the same physiological phenotype as the fully differentiated human cell types of interest (Chien et al., 2008). Therefore, both human ES cell research and human iPS cell research should be advanced in parallel.

For these reasons, the inventors isolated a new population of cells, the human ISL1+ primordial progenitor from human ES cells, which has the capacity to differentiate into the multipotent isl1+ progenitors (MICPs) and CMP from human ES cells, and can differentiate into all three major cell types of the heart: cardiomyocytes, smooth muscle cells and endothelial cells.

At the same time, the inventors also demonstrate the ability of ES cell-derived human ISL1+ primordial progenitors to integrating into the functional myocardium. This study is different from the recent article which allegedly reports human ES cell-derived cardiomyocytes are found to integrate into the heart of non-obese diabetic/severe combined immunodeficient (NOD/SCID) mice two weeks after transplantation (Yang et al., 2008), as here, the inventors use a human ISL1+ primordial progenitor population to be implanted. Further, as discussed before, several groups also find that murine ES cell-derived grafts do not survive longer than 3 months in vivo even in syngeneic recipients. To address this issue, the inventors prolong graft survival of ES cell-derived human ISL1+ primordial progenitor and their cardiac progenies in vivo by expressing creb 312, which is involved in protecting cardiac cells from stress-induced apoptotic death during embryonic heart development.

In Vitro Differentiation of Marine ES Cells into Isl1+ Progenitors and Cardiac Cells.

Murine Isl1-nlacZ knockin ES cells were generated by insertion of a loxP-flanked nuclear lacZ SV40 pA casstte, followed by hrGFP and a neoselectable marker flanked by ferrotransferrin sites into Exon 1 of the genomic isl1 locus (Sun et al., 2007). ES cells can differentiate into cardiac cells using protocol described by Moretti and colleagues (Moretti et al., 2006). Briefly, ES cells are differentiated for 5 days as embryoid bodies (EB) formed in hanging drops of ES cell medium. After that, expression of the isl1 gene can be monitored with lacZ staining. Before transplantation, we will check whether those progenitors can differentiate in vitro by dissociating the five-day EB into single cells. Growing clones from single cells plated on feeders, cardiac mesenchymal cells (CMC), are picked after 6-7 days. The cells are replated for differentiation. Differentiation into cardiomyocytes is triggered with DMEM/M199 medium containing 10% horse serum and 5% FBS on fibronectin; whereas differentiation into smooth muscle cells is triggered with DMEM/F12 complete medium on fibronection. Moreover, differentiation into endothelial cells is triggered with DMEM supplemented with 10% FBS and 50 ng/ml mouse VEGF on collagen. Lineage tracing is confirmed with immunostaining for markers: cardiac troponin T (cTnT), smooth muscle-myosin heavy chain, and platelet-endothelial cell adhesion molecule of endothelial cells.

The inventors have previously isolated distinct heart progenitors using a two-colored reporter system based on the expression of a red reporter exclusively in secondary heart field and a green reporter expressed in both the primary and secondary heart fields. Using this system, the inventors herein demonstrate the ability to purify mouse isl1+ primordial progenitors (red positive, green negative), primary heart field progenitors (green positive, red negative), and CMP (red positive, green positive) from ES cells of the double transgenic Nkx2.5–eGFP/AHF-DsRed mice. By plating the 6-day ES cells onto engineered thin films composed of polydimethylsiloxane elastomer with alternating fibronectin/pluronic coating, these cells differentiate into striated rod shaped, beating cardiomyocytes after 7 days in culture.

Figure 11:
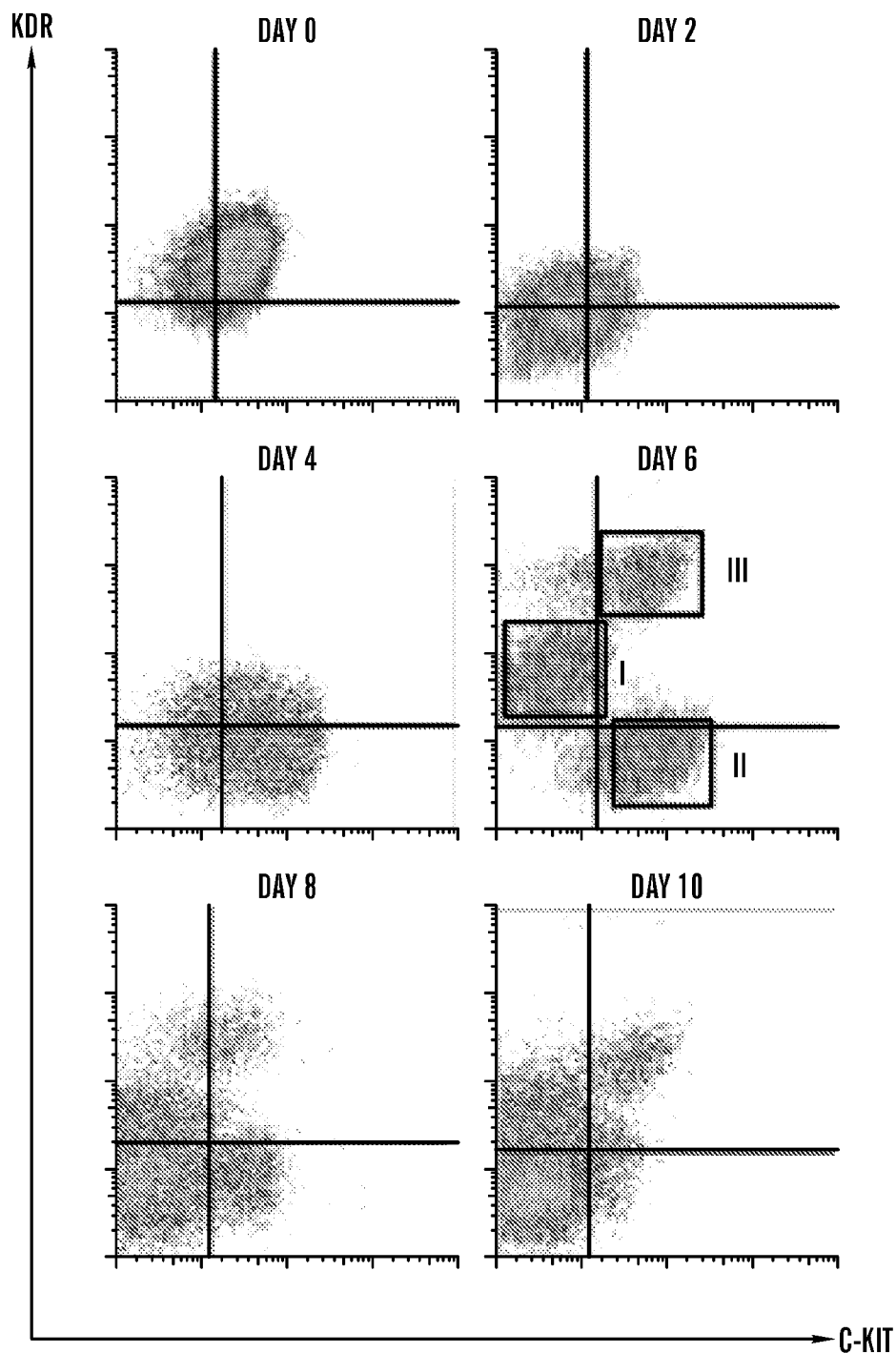
FIG. 11 shows identification and characterization of the cardiovascular KDR$^{Low}$/c-kit$^{neg}$ derived from human EBs.

The inventors demonstrate isolation of such mouse ES-derived ISL1+ primordial progenitors (see FIG. 11)

Example 4

Maximizing Survival of Isl1+ Progenitors by Over-Expressing the Novel Prosurvival Gene, Creb 312

It has been previously reported that multiple, parallel processes contribute to death of cardiac grafts in vivo (Laflamme et al., 2007). Human ES cell-derived cardiomyocytes were transplanted with a prosurvival cocktail which included caspase inhibitors z-VAD.fmk that attenuate caspase-dependent apoptosis, cell-permeate peptide from Bch XL that blocks mitochondria-dependent apoptosis, small molecules such as cyclosporin A which that inhibits cyclophilin D-dependent mitochondrial pathways, and growth factors such as IGF-1 that activates Akt pathways (Laflamme et al., 2007). Indeed, the recipient heart showed both cell engraftment and functional improvement at four weeks after transplantation (Laflamme et al., 2007). However, at 12 weeks after transplantation, the observed functional benefit no longer evident (Van Laake et al., 2007). Therefore, new approaches are needed to prolong cardiac survival after transplantation. In fact, the ES cell-derived isl1+ progenitors might have enhanced capability of long-term survival as they are authentic endogenous heart progenitors.

In order to optimize survival of grafted human ISL1+ primordial progenitors and their derivatives in vivo after transplantation, the inventors demonstrate the use of adenovirus to transduce a Creb312 in ES cells and active it with small molecules such as phenylephrine.

The inventors have previosuly demonstrated creb 312 is a crucial prosurvival factor for cardiac cells. Creb 312 is a transcription factor of the basic region/leucine zipper family that is expressed predominantly in cardiac progenitors during early mouse development. Detailed analyses have shown that Creb 312 is expressed in progenitors of both the primary and secondary heart fields. Later in mouse development, it is expressed in all three lineage derivatives of isl1+ progenitors: cardiomyocytes, smooth muscle and endothelial cells.

The inventors demonstrate that Creb 312 is activated through post-translational modifications in response to physiological, mechanical and hypoxic stress. The activated form undergoes translocation to the nucleus, where it induces the expression of known cardiac stress-induced target genes such as BNP and ANF. Lack of Creb 312 through targeted inactivation in mouse leads to partial embryonic lethality due to an increased apoptosis of right ventricular cardiomyocytes and atrioventricular valves.

Accordingly, the inventors demonstrate that ES-derived ISL1+ progenitors can be genetically manipulated to express (in an inducible or cell-type specific expression pattern) Creb 312, which serves to act as a survival factor protecting the ISL1+ primordial progenitors against stress during embryonic heart development.

Example 5

To Determine the Potential of Isl1+ Progenitors in Cell Replacement Therapy by Inhibiting their Rejection in Vivo Across the Whole MHC Barrier The progressive cell loss after transplantation of cardiac cells could be due to inadequate vascular supply and/or chronic immune rejection. The vascular insufficient problem may be prevented by transplantation of ES-derived human ISL1+ primordial progenitors that are capable of vascularization and differentiate into multiple cardiac cell types. Accordingly, the inventors demonstrate that implantation of a population of ES-derived human ISL1+ primordial progenitor is better than implantation of a population of purified cardiomyocytes at generating functional, vascularized cardiac tissue.

In order to overcome the immune rejection of allogeneic ES cells, the inventors also administer the host animal a monoclonal antibody (mAb) against T-cell co-receptors, CD4 and CD8.

Figure 12A:
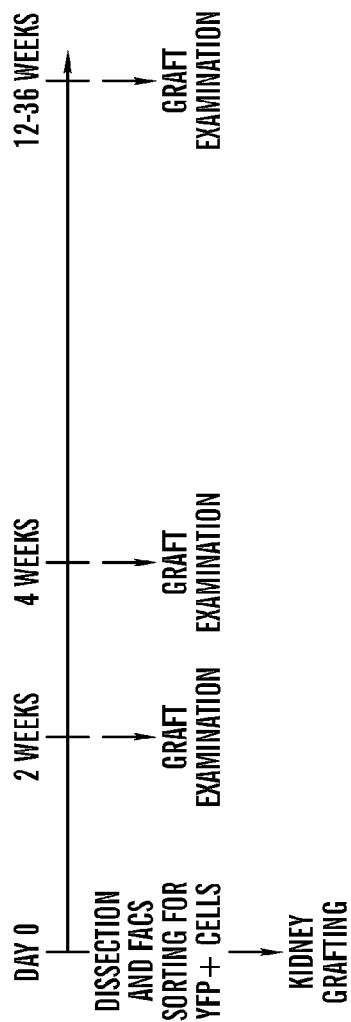
FIGS. 12A-12B shows transplantation of mouse ISL1+ primordial progenitors under the kidney capsule.
Figure 12B:
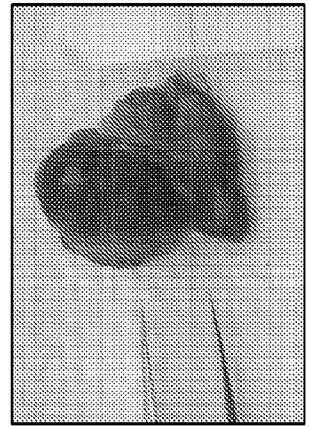

The inventors demonstrate that ES-derived human ISL1+ primordial progenitors transduced with the prosurvival factor, Creb 312, which have the potential or capacity to differentiate into isl1+ multipotent cardiovascular progenitors (MICPs) and CMP, and then transplanted under the kidney capsule of recipient mice (See FIG. 12B). The subcapsular region of the kidney serves as a good site for transplantation because of its good vascularization and it is easier to monitor survival without contamination with the host heart cells.

Figure 13A:
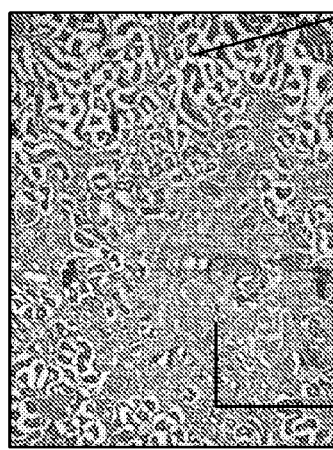
FIGS. 13A-13C show mouse YFP+ sorted cells (E10.5) are successfully engrafted 2 weeks after implantation into the mouse kidney capsule.
Figure 13C:
Figure 13B:
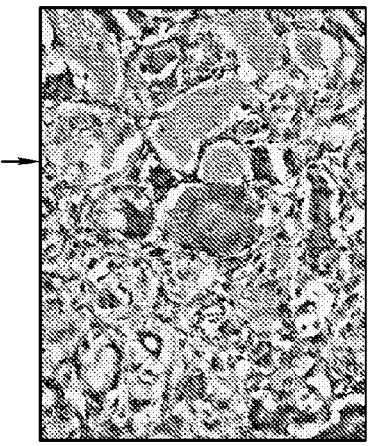

The inventors are able to monitor the grafted ES-derived human ISL1+ primordial progenitors for survival over a period of time (1-6 months). Alternatively, the inventors can transplant the ES-derived human ISL1+ primordial progenitors which have the capacity to differentiate into MICPs and CMP into the heart and investigate whether the grafts integrate into the heart. The inventors demonstrate that the implanted ES-derived human ISL1+ primordial progenitor do not form teratomas (FIGS. 13 and 15).

The inventors demonstrate transplanting murine CBA/Ca (H-$2^k$) embryoid bodies (see FIGS. 12B and 13A-13C) and ES-derived human ISL1+ primordial progenitor (FIG. 15A-15D) implanted under the kidney capsule of C57B1/6 (H-$2^b$) recipients which are administered 1 mg anti-CD4 and 1 mg anti-CD8 monoclonal antibodies (mAb), accepted the grafts even across the whole MHC mismatch.

The inventors demonstrate transplantation of approximately 2,000 mouse ISL1+ primordial progenitors under the kidney capsule, where mouse ISL1+ primordial progenitors are derived from embryonic progenitors (E9.5-10.5) derived from isl-1-cre×rasa-YFP mouse into the kidney capsule of mice (FIG. 12A). These mouse ISL1+ primordial progenitors successfully engrafted 2 weeks after implantation into the mouse kidney capsule (FIGS. 13A-13C), and differentiated along epithelial lineages to express the endothelial cell marker CD31 and CD146 two weeks after grafting into the kidney capsule. The inventors demonstrated expression of cardiovascular lineage markers in the implanted mouse ISL1+ primordial progenitors, by demonstrating the mouse ISL1+ primordial progenitors express YFP after grafting (but no Isl1 expression), and then differentiate along epithelial lineages to express the endothelial cell marker CD31 at least 2 weeks after grafting into the kidney capsule (data not shown). The inventors also demonstrated that the implanted mouse ISL1+ primordial progenitors differentiated along epithelial lineages to express the endothelial cell marker CD146 two weeks post transplantation (data not shown). The implanted mouse ISL1+ primordial progenitors differentiated along cardiomyocyte lineages to express the cardiomyocyte cell markers cTnT two weeks post transplantation (data not shown) and along smooth muscle lineages to express the smooth muscle markers SM-A and α-actinin and two weeks post transplantation (data not shown).

Figure 14A:
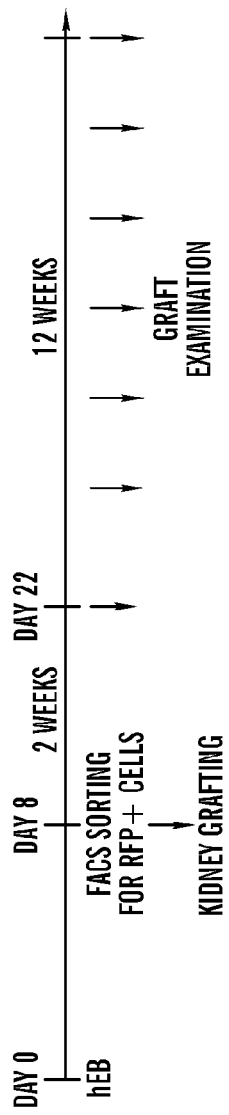
FIG. 14A-14B show implantation of human ISL1+ primordial progenitors derived from human ES cells under the kidney capsule in mice.
Figure 14B:
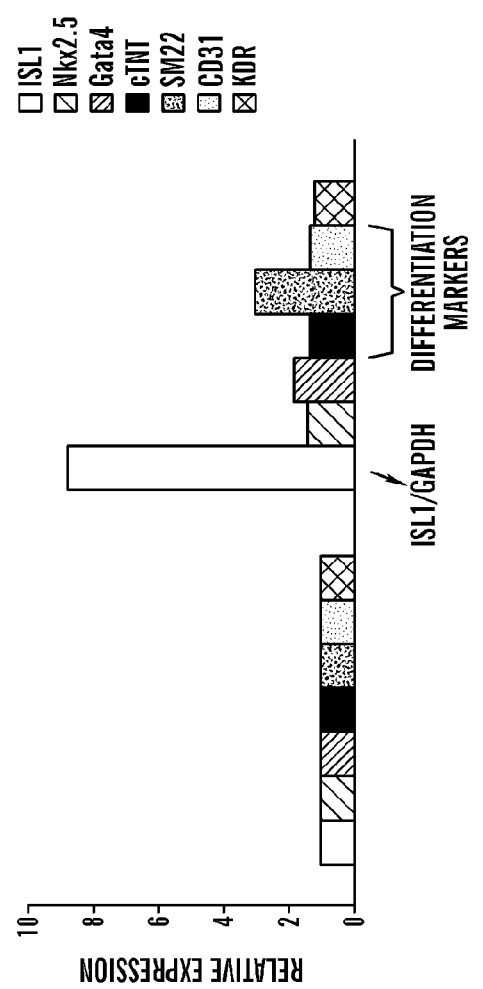
Figure 15A:
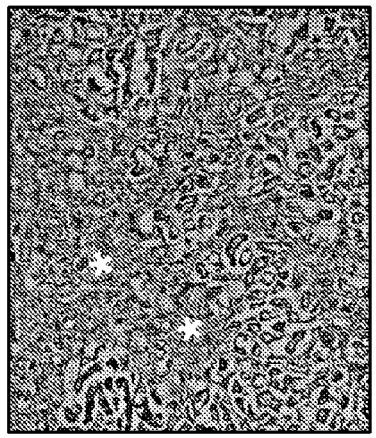
FIGS. 15A-15D shows the grafting of human ISL1+ primordial progenitors in the mouse kidney capsule.
Figure 15B:
Figure 15C:
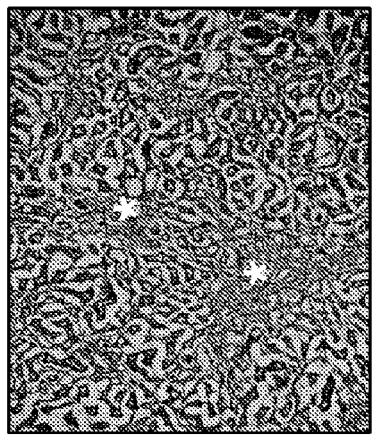
Figure 15D:
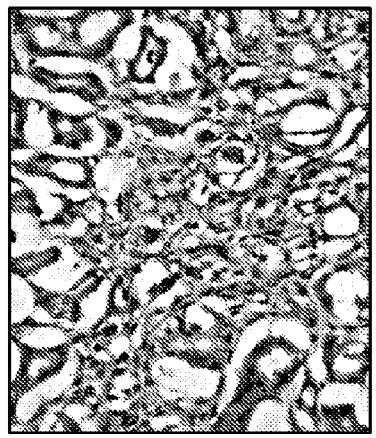

The inventors demonstrate transplantation of approximately 2,000 human ISL1+ primordial progenitors under the kidney capsule, where human ISL1+ primordial progenitors are derived from human EB (D8) derived from the H9 Isl1-Cre-RFP ES cell line, and directly implanted into the kidney capsule of mice. These cells are not differentiated prior to implantation (FIG. 14B), but have the capacity to spontaneous differentiation into all three cardiovascular lineages in vitro (e.g. cardiomyocytes, endothelial cells and smooth muscle cells) (FIG. 14C). These human ISL1+ primordial progenitors successfully graft into the kidney capsule (FIGS. 15A-15D), and differentiate along epithelial lineages to express the endothelial cell marker CD31 and smooth muscle lineages to express the smooth muscle markers SM-A and α-SM-MHC at two weeks after grafting into the kidney capsule (data not shown). After one month, the implanted human ISL1+ primordial progenitors have differentiated into the three different lineages; smooth muscle lineages, endothelial cell lineages and cardiomyocyte lineages (data not shown).

Example 6

Surprisingly, the inventors demonstrate that after one month the implanted human ISL1+ primordial progenitors have undergone coordinated differentiation into different cardiac cell types to form distinct vascular type structures, with the lumen surface positive for CD31 (endothelial marker) expression surrounded by a layer of cells positive for the smooth muscle marker SM-A and peripheral to the layer of cells positive for SM-A are cells which express α-actinin, a marker for cardiomyocytes (data not shown). Thus, the inventors have demonstrated the generation of human vascularized cardiac tissue in vivo from a population of ES-derived human ISL1+ primordial progenitors. Stated a different way, the ISL1+ primordial progenitors differentiate to form an organized human cardiac tissue having a three-dimensional cellular organization of the cardiac tissue that is vascularized.

Similarly, the inventors demonstrate maximal survival of murine ES cell-derived cardiac cells and ES-derived human ISL1+ primordial progenitor grafts in allogeneic recipients by inhibiting graft rejection with co-receptor blockade-induced tolerance (using anti-CD4 and anti-CD8 mAb from Dr Herman Waldmann laboratory, Oxford, UK). Therefore, with the help of anti-CD4 and anti-CD8 mAb, the inventors demonstrate ES-derived human ISL1+ primordial progenitor implanted under the kidney capsule fully integrate into the kidney capsule of fully allogeneic recipients.

Figure 16B:
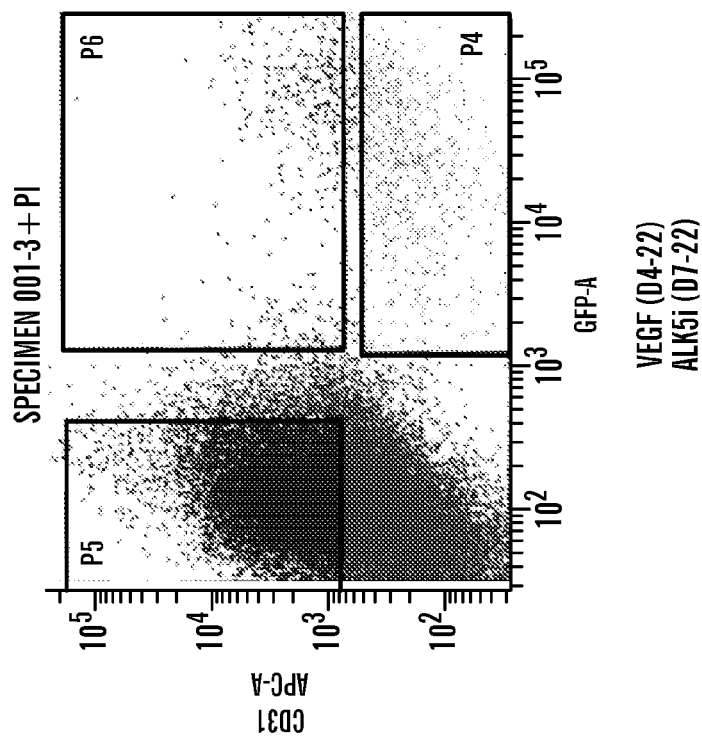
Figure 16A:
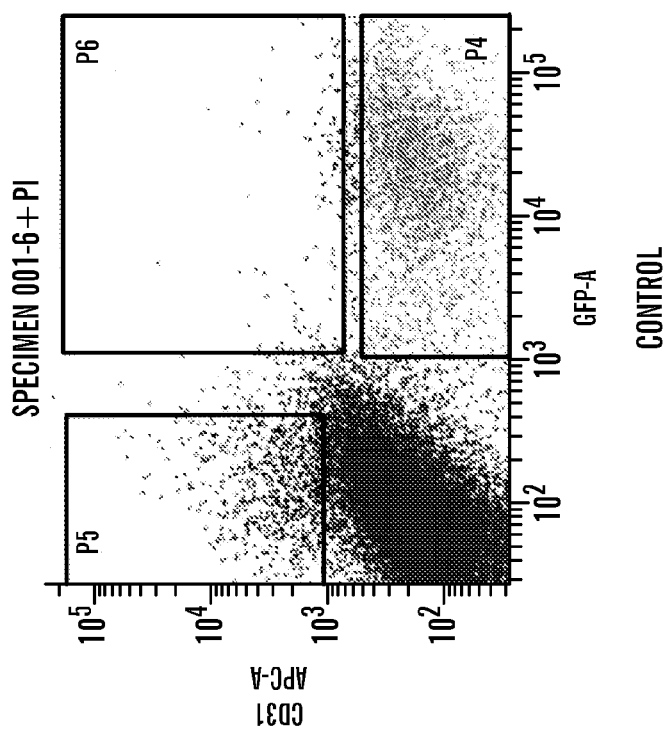

As demonstrated herein in FIGS. 16A-16C, human Isl1+ primordial progenitors can be differentiated along vasculargenic lineages into Isl1+/CD31+ cells by contacting the human Isl1+ primordial progenitors with VEGF, between about Day 4 and about Day 22 (D4-D22) or ALK5 inhibitor between day 7 and day 22 (D7-D22). When Isl1+ primordial progenitors are contacted with VEGF the express CD31, as shown in FIGS. 16B and 16C, and as demonstrated by detection of GFP expression by immunostaining at D20 (data now shown). The inventors also demonstrated that VEGF treatment also produced vessel-like structures in vitro (data not shown), and that while the spontaneous differentiation to Isl1+/CD31+ cells in the absence of VEGF is low, this can be increased by about 2-fold with VEGF treatment. The inventors also demonstrated that while prolonged treatment of the Isl1+ primordial progenitors with ALK5i, e.g., SB431542, reduced the overall human Isl1+ (GFP+) population, it increased the proportion of human Isl1+/CD31+ (GFP+/CD31+) cells by about 4-5-fold (see FIG. 16C).

The inventors also similarly demonstrated that VEGF and ALK5i promotes the vasculargenic commitment of mouse ES cells into human Isl1+/CD31+ cells, and also increases the proportion of Isl1−/CD31+ cells by contacting the Isl1+ primordial progenitors with VEGF for about 2 weeks beginning at about D4.

Figure 17A:
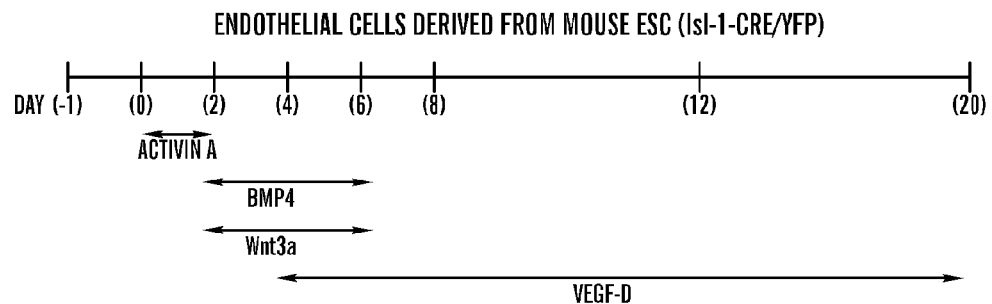
FIGS. 17A-17B show endothelial cells can be derived from mouse ES cells derived from Isl-1/cre/YFP transgenic mouse.
Figure 17B:
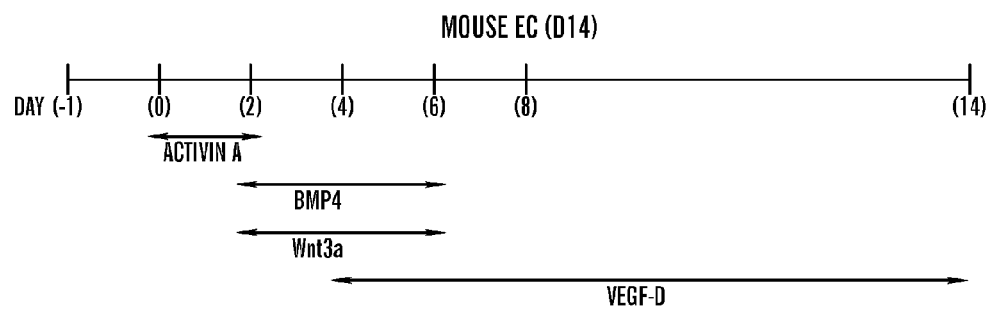
Figure 17C:
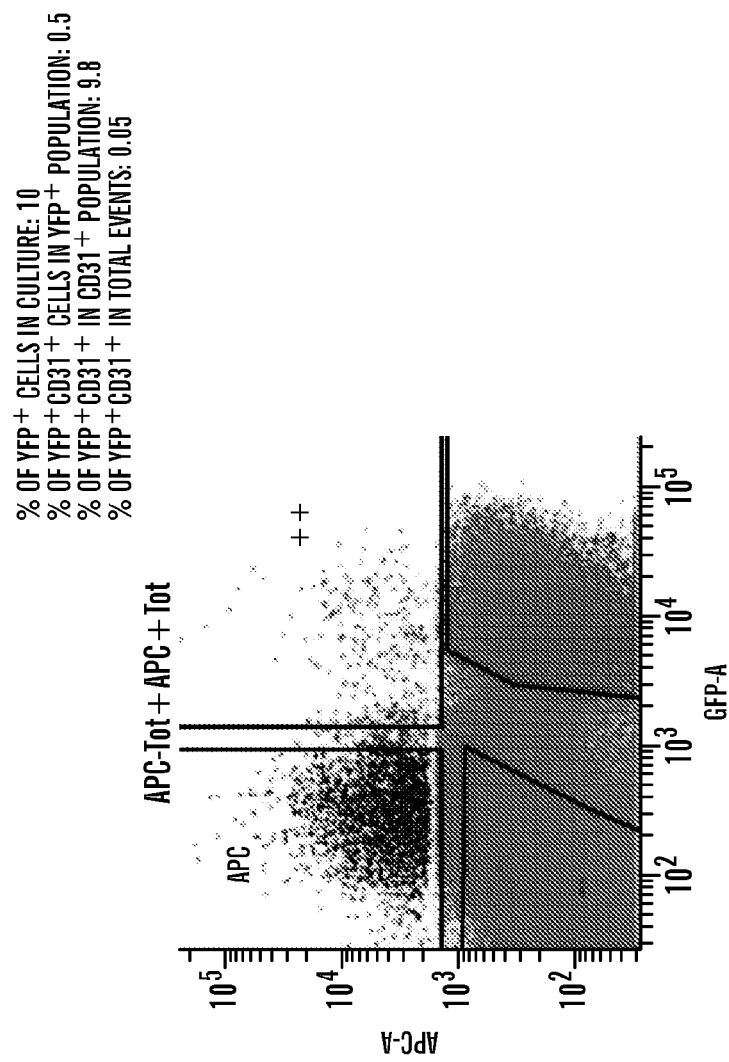
FIG. 17C shows results of FACs with anti-CD31 of mouse ES cells contacted with VEGF, demonstrating that pre-treatment of Isl1+ cells increases efficiency of differentiation into Isl1+/CD31+ cells.

FIG. 17B shows another embodiments of a protocol to promote the vasculargenic commitment of mouse ES cells into mouse Isl1+/CD31+ cells by contacting with VEGF for about 2 weeks beginning by about D4 and continuing to D20, and as demonstrated by detection of YFP expression by immunostaining at D20 (data now shown). The inventors also sorted the Isl1+(YFP+) cells at D8 (which had been treated with VEGF from D4-D8) and continued culturing the sorted cells in the presence of VEGF in vitro until D20, and immunostaining demonstrated vessel-like structures (data not shown). The treatment of mouse Isl1+ cells with VEGF increases efficiency of differentiation into Isl1+/CD31+ cells by about at least 2-fold.

Therefore, the inventors have demonstrated methods to produce human vascularized cardiac tissue in a mouse in vivo and to increase efficiency of differentiation of Isl1+ primordial progenitors along vasculargenic lineages. The inventors can use these human Isl1+ primordial progenitors, and their differentiated Isl1+/CD31+ cells that have differentiated along vasculargenic lineages to study the survival, engraftment and regenerative potential of the ES-derived human ISL1+ primordial progenitors, as well as a model to test agents to identify those which affect the function of the human vascularized cardiac tissue in the mouse. Also, the inventors discovery enables the generation of vascularized human cardiac tissue for potential regenerative therapy for cardiovascular disease or injury.

The inventors also demonstrate the graft of the ES-derived human ISL1+ primordial progenitors by immunostaining for the distinct MHC molecules and assess for expression of adherens junctions such as N-cadherin (Laflamme et al., 2007). Moreover, the inventors demonstrate minimal proliferation, if any, of the ES-derived human ISL1+ primordial progenitor graft by immunostaining for the thymidine analog 5-bromodeoxyuridine (BrdU) (Laflamme et al., 2007) or the marker Ki67 (data not shown).

REFERENCES

All references, patents and patent applications cited herein and throughout the specification are herewith incorporated by reference in their entirety.

1. Chien, K. R., Domian, I. J. & Parker, K. K. Cardiogenesis and the complex biology of regenerative cardiovascular medicine. Science 322, 1494-7 (2008).
2. Wu, S. M., Chien, K. R. & Mummery, C. Origins and fates of cardiovascular progenitor cells. Cell 132, 537-43 (2008).
3. Martin-Puig, S., Wang, Z. & Chien, K. R. Lives of a heart cell: tracing the origins of cardiac progenitors. Cell Stem Cell 2, 320-31 (2008).
4. Laugwitz, K. L., Moretti, A., Caron, L., Nakano, A. & Chien, K. R. Islet1 cardiovascular progenitors: a single source for heart lineages? Development 135, 193-205 (2008).
5. Kattman, S. J., Huber, T. L. & Keller, G. M. Multipotent flk-1+ cardiovascular progenitor cells give rise to the cardiomyocyte, endothelial, and vascular smooth muscle lineages. Dev Cell 11, 723-32 (2006).
6. Moretti, A. et al. Multipotent embryonic isl1+ progenitor cells lead to cardiac, smooth muscle, and endothelial cell diversification. Cell 127, 1151-65 (2006).
7. Laugwitz, K. L. et al. Postnatal isl1+ cardioblasts enter fully differentiated cardiomyocyte lineages. Nature 433, 647-53 (2005).
8. Cai, C. L. et al. Isl1 identifies a cardiac progenitor population that proliferates prior to differentiation and contributes a majority of cells to the heart. Dev Cell 5, 877-89 (2003).
9. Sun, Y. et al. Islet 1 is expressed in distinct cardiovascular lineages, including pacemaker and coronary vascular cells. Dev Biol 304, 286-96 (2007).
10. Cowan, C. A. et al. Derivation of embryonic stem-cell lines from human blastocysts. N Engl J Med 350, 1353-6 (2004).
11. Vintersten, K. et al. Mouse in red: red fluorescent protein expression in mouse ES cells, embryos, and adult animals. Genesis 40, 241-6 (2004).
12. Xu, H. et al. Tbx1 has a dual role in the morphogenesis of the cardiac outflow tract. Development 131, 3217-27 (2004).
13. Yang, L. et al. Human cardiovascular progenitor cells develop from a KDR+ embryonic-stem-cell-derived population. Nature 453, 524-8 (2008).
14. Ema, M. et al. Primitive erythropoiesis from mesodermal precursors expressing VE-cadherin, PECAM-1, Tie2, endoglin, and CD34 in the mouse embryo. Blood 108, 4018-24 (2006).
15. Motoike, T., Markham, D. W., Rossant, J. & Sato, T. N. Evidence for novel fate of Flk1+ progenitor: contribution to muscle lineage. Genesis 35, 153-9 (2003).
16. Zhou, B. et al. Epicardial progenitors contribute to the cardiomyocyte lineage in the developing heart. Nature 454, 109-13 (2008).
17. Zhou, B., Gise, A., Ma, Q., Rivera-Feliciano, J. & Pu, W. T. Nkx2-5- and Isl1-expressing cardiac progenitors contribute to proepicardium. Biochem Biophys Res Commun 375, 450-3 (2008).
18. Qyang, Y. et al. The renewal and differentiation of Isl1+ cardiovascular progenitors are controlled by a Wnt/beta-catenin pathway. Cell Stem Cell 1, 165-79 (2007).
19. Tzahor, E. Wnt/beta-catenin signaling and cardiogenesis: timing does matter. Dev Cell 13, 10-3 (2007).
20. Kwon, C. et al. Canonical Wnt signaling is a positive regulator of mammalian cardiac progenitors. Proc Natl Acad Sci USA 104, 10894-9 (2007).
21. Meijer, L. et al. GSK-3-selective inhibitors derived from Tyrian purple indirubins. Chem Biol 10, 1255-66 (2003).
22. Xu, C. et al. Feeder-free growth of undifferentiated human embryonic stem cells. Nat Biotechnol 19, 971-4 (2001).
23. world-wide web address at: //recombineering.ncifcrf.gov/.
24. Lee, E. C. et al. A highly efficient *Escherichia coli*-based chromosome engineering system adapted for recombinogenic targeting and subcloning of BAC DNA. Genomics 73, 56-65 (2001).
25. Zwaka, T. P. & Thomson, J. A. Homologous recombination in human embryonic stem cells. Nat Biotechnol 21, 319-21 (2003).
26. Davis, R. P. et al. Targeting a GFP reporter gene to the MIXL1 locus of human embryonic stem cells identifies human primitive streak-like cells and enables isolation of primitive hematopoietic precursors. Blood 111, 1876-84 (2008).
27. Bruneau, B. G. et al. (2001). Cell. 106, 709-21
28. Cai, C. L. et al. (2003). Dev Cell. 5, 877-89
29. Chien, K. R. (2008). Nature. 453, 302-5.
30. Fazel, S. et al. (2006). J Clin Invest. 116, 1865-77
31. Fazel, S. S. et al. (2008). FASEB J. 22, 930-40
32. Franco, D. et al. (2007). Cell Mol Life Sci. 64, 683-91
33. Kim J B et al. (2008). Nature. 454, 646-50
34. Laflamme M A et al. (2007). Nat. Biotechnol. 25, 1015-24
35. Laugwitz, K. L. et al. (2005). Nature. 433, 647-53
36. Moretti, A. et al. (2006). Cell. 127, 1151-65
37. Murry, C. E. et al. (2004). Nature. 428, 664-68
38. Qyang, Y. et al. (2007). Cell Stem Cell. 1, 165-179
39. Robertson, N. J. et al. (2007). Proc Natl Acad Sci USA. 104, 20920-25
40. Sun Y et al. (2007). Dev Biol. 304, 286-96
41. Van Laake, L. W. et al. (2007). Stem Cell Research. 1, 9-24
42. Yang, L. et al. (2008). Nature. 453, 524-280

The invention claimed is:
1. A method for enhancing the differentiation of a Isl1+ primordial progenitor cells into a vasculargenic lineage cell which express Isl1+ and CD31+, the method comprising:
   (a) selecting a population of cultured Isl1+ primordial progenitor cells, wherein the Isl1+ primordial progenitor cells express Isl1 but do not express Nkx2.5 or Kdr, and wherein the Isl1+ primordial progenitor cells are obtained from pluripotent stem cells, and

(b) contacting the population of Isl1+ primordial progenitor cells from step (a) with at least one of VEGF or TGFβ inhibitor.

2. The method of claim 1, wherein the Isl1+ primordial progenitor is a human Isl1+ primordial progenitor.

3. The method of claim 1, wherein the VEGF is selected from the group consisting of: $VEGF_{165}$, VEGF A, VEGF B, VEGF C, VEGF D, VEGF E, and VEGF F.

4. The method of claim 1, wherein the TGFβ inhibitor is an ALK5 inhibitor.

5. The method of claim 4, wherein the ALK5 inhibitor is SB431542 or A-83-01.

6. The method of claim 1, wherein the population Isl1+ primordial progenitors are contacted with VEGF or a TGFβ inhibitor or both for least 2 days.

7. The method of claim 1, wherein the VEGF is used at a concentration of between 25-50 ng/ml or a concentration of between 2-10 ng/ml.

8. The method of claim 4, wherein the ALK5 inhibitor is used at a concentration of between 25-50 ng/ml or a concentration of between 25-50 ng/ml.

9. The method of claim 1, wherein the pluripotent stem cells are induced pluripotent stem (iPS) cells.

10. The method of claim 1, wherein the plurpotent stem cells are embryonic stem cells.

* * * * *